(12) United States Patent
Yamanaka et al.

(10) Patent No.: US 8,030,042 B2
(45) Date of Patent: Oct. 4, 2011

(54) POLYAMINO ACID SYNTHETASE AND GENE ENCODING THE SAME

(75) Inventors: Kazuya Yamanaka, Kanagawa (JP); Yoshimitu Hamano, Fukui (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 12/450,891

(22) PCT Filed: Apr. 18, 2008

(86) PCT No.: PCT/JP2008/057618
§ 371 (c)(1),
(2), (4) Date: Oct. 16, 2009

(87) PCT Pub. No.: WO2008/130034
PCT Pub. Date: Oct. 30, 2008

(65) Prior Publication Data
US 2010/0248305 A1    Sep. 30, 2010

(30) Foreign Application Priority Data

Apr. 20, 2007 (JP) ................................. 2007-112078
Sep. 21, 2007 (JP) ................................. 2007-244997
Feb. 1, 2008 (JP) ................................. 2008-022841

(51) Int. Cl.
*C12N 9/00* (2006.01)
*C12N 1/20* (2006.01)
*C12N 1/00* (2006.01)
*C12N 15/00* (2006.01)
*C07H 21/04* (2006.01)

(52) U.S. Cl. ................. 435/183; 435/252.3; 435/252.33; 435/254.1; 435/320.1; 536/23.2

(58) Field of Classification Search ........................ None
See application file for complete search history.

(56) References Cited

U.S. PATENT DOCUMENTS
2003/0119018 A1* 6/2003 Omura et al. ..................... 435/6

FOREIGN PATENT DOCUMENTS
JP           2005-52010         3/2005

OTHER PUBLICATIONS

Kawai, T. et al., *Biosynthesis of ϵ-poly-L-lysine in a cell-free system of Streptomyces albulus*, Biochemical and Biophysical Research Communications, vol. 311 (2003), pp. 635-640.
Saimura, M. et al., *Purification and Characterization of poly(ϵ-L-lysine) biosynthetic enzyme*, Polymer Reprints, Japan, vol. 52, No. 5 (2003), p. 992 (with English translation).
Omura, S. et al., *Genome sequence of an industrial microorganism Streptomyces avermitilis: deducing the ability of producing secondary metabolites*. Genbank, Oct. 11, 2001, Acc. No. AB070954, CDS: 6659-10534. *NCBI Sequence Viewer v2.0.* Web. May 7, 2008. <http://www.ncbi.nlm.nih.gov/entrez/viewer.fcgi?15824207:DDBJ:5623295>.
Berg, H. et al., *Biosynthesis of the cyanobacterial reserve polymer multi-L-arginyl-poly-L-aspartic acid (cyanophycin)*, Eur. J. Biochem., vol. 267 (2000), pp. 5561-5570.
Aboulmagd, E. et al., *Purification of Synechocystis sp. Strain PCC6308 Cyanophycin Synthetase and Its Characterization with Respect to Substrate and Primer Specificity*, Applied and Environmental Microbiology, vol. 67, No. 5 (May 2001), pp. 2176-2182.
Ashiuchi, M. et al., *Enzymatic Synthesis of High-Molecular-Mass Poly-γ-Glutamate and Regulation of Its Stereochemistry*, Applied and Environmental Microbiology, vol. 70, No. 7 (Jul. 2004), pp. 4249-4255.
Shima, S. et al., *Poly-L-lysine Produced by Streptomyces. Part II. Taxonomy and Fermentation Studies*, Agric. Biol. Chem., vol. 45, No. 11 (1981), pp. 2497-2502.
Supplementary European Search Report issued Dec. 27, 2010 in corresponding European Application No. EP 08 74 0665.
Database Uniprot [Online], retrieved from EBI accession No. A1TG57, Feb. 6, 2007.
Kazuya Yamanaka et al., ϵ-Poly-L-lysine dispersity is controlled by a highly unusual nonribosomal peptide synthetase, Nature Chemical Biology, vol. 4, No. 12, 2008, pp. 766-772.
Yoshimitsu Hamano et al., Development of gene delivery systems for the ϵ-Poly-L-lysine producer, *Streptomyces albulus*, Journal of Bioscience and Bioengineering, vol. 99, No. 6, 2005, pp. 636-641.
Y. Hamano et al., Biological function of the *pld* gene product that degrades ϵ-Poly-L-lysine in *Streptomyces albulus*, Applied Microbiology and Biotechnology, vol. 72, No. 1, 2006, pp. 173-181.
Nicholas Grammel et al., A β-lysine adenylating enzyme and a β-lysine binding protein involved in poly β-lysine chain assembly in nourseothricin synthesis in *Streptomyces noursei*, European Journal of Biochemistry, vol. 269, No. 1, 2002, pp. 347-357.

\* cited by examiner

*Primary Examiner* — Nashaat Nashed
(74) *Attorney, Agent, or Firm* — Wenderoth, Lind & Ponack, L.L.P.

(57) ABSTRACT

The present invention provides an enzyme which catalyzes amino acid polymerization in the form of a non-ribosomal peptide synthetase (NRPS) and a gene encoding the same.

18 Claims, 11 Drawing Sheets

Fig. 1
(A)
General scheme of NRPS
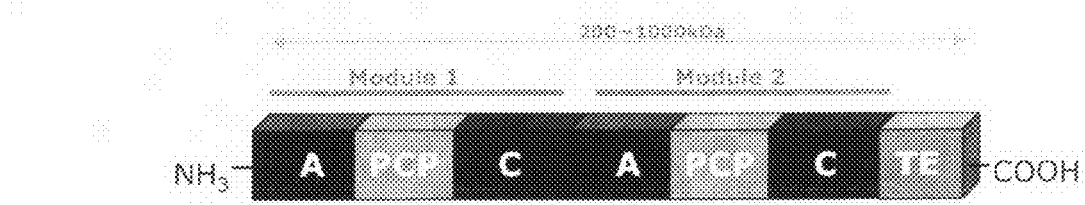
(B)
ε-PL Synthetase
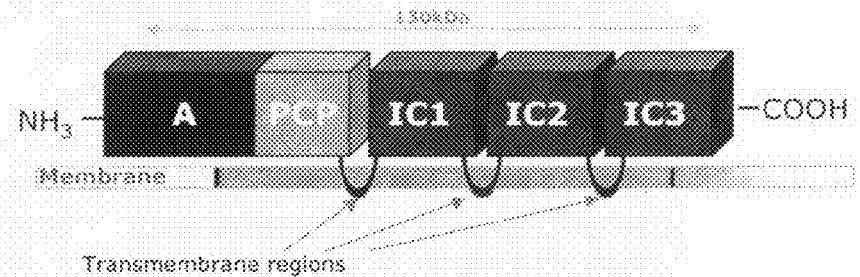

Fig. 2

(A)
IC1 AA Seq.
676 – 847
ARALAGTIKPGAYPRGGATHLRLWTAERVVAAFGVPSLLGTPWARLYARSLGCATGRNVALHTMPPVTGLAELGDGCSVE
PEADISGWWLDGDTLHIGAVRIGAGARVAHRSMLMPGAVVGQGAELASGACLDGEIPDGASWSGSPARPAGAAERMAGAA
WPAPAWQRSRRW (SEQ ID NO: 15)

(B)
IC2 AA Seq.
914 –1083
RLLGRGITPGLHPASGGVAWRAWLVTRLLDGARGSLFPLYASLGTPHWLRLLGAKVGRHAEISTVLPLPSLLHVEDGAFL
ADDTLVAPFELRGGWLRLGTVRIGRRAFVGNSGIVDPGHDVPDHSLVGVLSNAPADGEPGSSWLGRPAMPLPRVATQADP
ARTFAPPRRL (SEQ ID NO: 17)

(C)
IC3 AA Seq.
1147 – 1299
KWLLVGRFTVSEHPLWSSFVWRNELYDTFVESLAVPSMAGAFTGTPVLNWWLRTLGAKIGRGVWLESYWLPETDLITVAD
GVSVNRGCVLQTHLFHDRIMRLDTVRLAEGSSLGPHGIVLPGTEVGARASIAPSSLVMRGESVPAHTRWAGNP    (SEQ
ID NO: 19)

(D)
-tmr- IC1 – tmr – IC2 – tmr – IC3   AA Seq.
611- 1319
VQLLVQTGLYGIAGLRGLVGLALADNVLGLLAPQVWAPHTAWWLIIVGWVVLYSAPMRCALGALAARALAGTIKPGAYPR
GGATHLRLWTAERVVAAFGVPSLLGTPWARLYARSLGCATGRNVALHTMPPVTGLAELGDGCSVEPEADISGWWLDGDTL
HIGAVRIGAGARVAHRSMLMPGAVVGQGAELASGACLDGEIPDGASWSGSPARPAGAAERMAGAAWPAPAWQRSRRWSAA
YGLTLLGLPLLALLSTAPALVGAYFLLRDSGTLATAGLRLLLAVPVFTLLTTGCSLLVTAAVVRLLGRGITPGLHPASGG
VAWRAWLVTRLLDGARGSLFPLYASLGTPHWLRLLGAKVGRHAEISTVLPLPSLLHVEDGAFLADDTLVAPFELRGGWLR
LGTVRIGRRAFVGNSGIVDPGHDVPDHSLVGVLSNAPADGEPGSSWLGRPAMPLPRVATQADPARTFAPPRRLVRARAAV
ELCRVLPLMCGLALAEGVFLTEQDAFAQGGLGLAALVGAPLLLASGLVALLVTTLAKWLLVGRFTVSEHPLWSSFVWRNE
LYDTFVESLAVPSMAGAFTGTPVLNWWLRTLGAKIGRGVWLESYWLPETDLITVADGVSVNRGCVLQTHLFHDRIMRLDT
VRLAEGSSLGPHGIVLPGTEVGARASIAPSSLVMRGESVPAHTRWAGNPIAGERPARPVPARAEGGAAA    (SEQ   ID
NO: 13)

Fig. 3

(A)
IC1 DNA Seq.
2026-2541
GCCCGCGCGCTCGCCGGCACCATCAAGCCCGGCGCCTACCCGCGCGGCGGCGCCACCCACCTGCGCCTGTGGACCGCCGA
ACGCGTCGTCGCCGCCTTCGGCGTCCCCTCCCTGCTCGGCACCCCTGGGCGCGGCTCTACGCCCGGAGCCTGGGCTGCG
CCACAGGGCGGAACGTGGCGCTGCACACCATGCCGCCGGTCACCGGCCTCGCCGAACTCGGCGACGGCTGCAGCGTCGAA
CCCGAGGCCGACATCTCCGGCTGGTGGCTCGACGGCGACACCCTGCACATCGGCGCGGTCCGGATCGGCGCCGGCGCCCG
GGTCGCCCACCGCAGCATGCTGATGCCCGGCGCCGTCGTCGGCCAGGGCGCCGAACTCGCCTCCGGCGCCTGCCTGGACG
GAGAGATCCCCGACGGCGCCTCGTGGTCCGGCTCCCCGGCCCGCCCGGCCGGCGCCGCCGAGCGGATGGCCGGCGCCGCC
TGGCCCGCCCCCGCCTGGCAGCGCTCGCGCCGCTGG (SEQ ID NO: 14)

(B)
IC2 DNA Seq.
2740-3249
CGCCTCCTCGGCCGCGGCATCACGCCGGGACTGCACCCCGCGAGCGGTGGCGTCGCCTGGCGCGCCTGGCTGGTCACCCG
CCTCCTGGACGGCGCCCGCGGCAGCCTCTTCCCGCTCTACGCCAGCCTCGGCACCCCGCACTGGCTGCGGCTGCTCGGCG
CCAAGGTCGGCCGGCACGCGGAGATCTCCACCGTGCTGCCGCTGCCCTCCCTGCTGCACGTCGAGGACGGCGCGTTCCTC
GCCGACGACACCCTGGTGGCGCCCTTCGAACTCCGCGGCGGCTGGCTGCGGTTGGGGACCGTCCGGATCGGTCGCCGGGC
CTTCGTCGGCAACTCCGGCATCGTCGACCCCGGCCACGACGTGCCCGATCACAGCCTGGTCGGCGTGCTCTCCAACGCCC
CCGCCGACGGCGAGCCCGGCTCGTCCTGGCTGGGCCGGCCCGCCATGCCGCTGCCCCGGGTGGCGACCCAGGCCGACCCG
GCGCGCACCTTCGCACCGCCGCGCAGGCTG (SEQ ID NO: 16)

(C)
IC3 DNA Seq.
3439-3897
AAGTGGCTGCTGGTCGGCCGCTTCACGGTGAGCGAGCACCCCCTGTGGTCGTCGTTCGTGTGGCGCAACGAGCTCTACGA
CACCTTCGTCGAATCGCTCGCCGTGCCGTCGATGGCCGGCGCGTTCACCGGCACCCCGGTCCTGAACTGGTGGCTGCGCA
CCCTCGGCGCCAAGATCGGGCGCGGGGTCTGGTTGGAGAGCTACTGGCTGCCGGAGACCGACCTGATCACCGTCGCCGAC
GGCGTCAGCGTCAACCGCGGCTGCGTCCTGCAGACCCACCTCTTCCACGACCGGATCATGCGGCTGGACACCGTCCGCCT
CGCCGAAGGCTCCTCGCTCGGCCCGCACGGCATCGTGCTCCCCGGCACCGAGGTCGGGGCGCGCGCCTCGATCGCGCCGT
CGTCCCTGGTCATGCGCGGCGAGAGCGTCCCGGCCCACACCCGGTGGGCCGGCAACCCG (SEQ ID NO: 18)

<u>-tmr- IC1 - tmr - IC2 - tmr - IC3   DNA Seq.</u>
1831-3957
GTCCAACTCCTCGTCCAGACCGGCCTGTACGGCATCGCCGGCCTGCGCGGACTGGTCGGGCTCGCGCTCGCGGACAACGT
CCTCGGCCTGCTCGCCCCGCAGGTCTGGGCCCCGCACACCGCGTGGTGGCTGATCATCGTCGGCTGGGTGGTGCTCTACA
GCGCCCCGATGCGTTGCGCCCTCGGCGCACTGGCCGCCCGCGCGCTCGCCGGCACCATCAAGCCCGGCGCCTACCCGCGC
GGCGGCGCCACCCACCTGCGCCTGTGGACCGCCGAACGCGTCGTCGCCGCCTTCGGCGTCCCCTCCCTGCTCGGCACCCC
CTGGGCGCGGCTCTACGCCCGGAGCCTGGGCTGCGCCACAGGGCGGAACGTGGCGCTGCACACCATGCCGCCGGTCACCG
GCCTCGCCGAACTCGGCGACGGCTGCAGCGTCGAACCCGAGGCCGACATCTCCGGCTGGTGGCTCGACGGCGACACCCTG
CACATCGGCGCGGTCCGGATCGGCGCCGGCGCCCGGGTCGCCCACCGCAGCATGCTGATGCCCGGCGCCGTCGTCGGCCA
GGGCGCCGAACTCGCCTCCGGCGCCTGCCTGGACGGAGAGATCCCCGACGGCGCCTCGTGGTCCGGCTCCCCGGCCCGCC
CGGCCGGCGCCGCCGAGCGGATGGCCGGCGCCGCCTGGCCCGCCCCCGCCTGGCAGCGCTCGCGCCGCTGGAGCGCCGCC
TACGGACTGACCCTGCTGGGCCTGCCGCTGCTGGCCCTGCTGTCCACCGCGCCCGCCCTGGTCGGCGCGTACTTCCTGCT
CCGCGACAGCGGCACCCTCGCCACAGCCGGGCTTCGCCTGCTGCTGGCCGTCCCGGTCTTCACGCTCCTGACCACTGGCT
GCTCCCTCCTCGTCACCGCCGCCGTGGTGCGCCTCCTCGGCCGCGGCATCACGCCGGGACTGCACCCCGCGAGCGGTGGC
GTCGCCTGGCGCGCCTGGCTGGTCACCCGCCTCCTGGACGGCGCCCGCGGCAGCCTCTTCCCGCTCTACGCCAGCCTCGG
CACCCCGCACTGGCTGCGGCTGCTCGGCGCCAAGGTCGGCCGGCACGCGGAGATCTCCACCGTGCTGCCGCTGCCCTCCC
TGCTGCACGTCGAGGACGGCGCGTTCCTCGCCGACGACACCCTGGTGGCGCCCTTCGAACTCCGCGGCGGCTGGCTGCGG
TTGGGGACCGTCCGGATCGGTCGCCGGGCCTTCGTCGGCAACTCCGGCATCGTCGACCCCGGCCACGACGTGCCCGATCA
CAGCCTGGTCGGCGTGCTCTCCAACGCCCCGCCGACGGCGAGCCCGGCTCGTCCTGGCTGGGCCGGCCCGCCATGCCGC
TGCCCCGGGTGGCGACCCAGGCCGACCCGGCGCGCACCTTCGCACCGCCGCGCAGGCTGGTCCGGGCCCGCGCCGCCGTC
GAGCTGTGCCGGGTGCTGCCGCTGATGTGCGGCCTGGCGCTCGCCGAGGGCGTGTTCCTCACCGAGCAGGACGCCTTCGC
CCAGGGCGGCCTCGGTCTCGCCGCACTGGTCGGCGCCCCGCTGCTGCTGGCCTCGGGCCTCGTGGCGCTGCTCGTCACCA
CCCTCGCGAAGTGGCTGCTGGTCGGCCGCTTCACGGTGAGCGAGCACCCCCTGTGGTCGTCGTTCGTGTGGCGCAACGAG
CTCTACGACACCTTCGTCGAATCGCTCGCCGTGCCGTCGATGGCCGGCGCGTTCACCGGCACCCCGGTCCTGAACTGGTG
GCTGCGCACCCTCGGCGCCAAGATCGGGCGCGGGGTCTGGTTGGAGAGCTACTGGCTGCCGGAGACCGACCTGATCACCG
TCGCCGACGGCGTCAGCGTCAACCGCGGCTGCGTCCTGCAGACCCACCTCTTCCACGACCGGATCATGCGGCTGGACACC
GTCCGCCTCGCCGAAGGCTCCTCGCTCGGCCCGCACGGCATCGTGCTCCCCGGCACCGAGGTCGGGGCGCGCGCCTCGAT
CGCGCCGTCGTCCCTGGTCATGCGCGGCGAGAGCGTCCCGGCCCACACCCGGTGGGCCGGCAACCCGATCGCCGGCGAAC
GCCCCGCCCGCCCCGTCCCGGCACGCGCGGAGGGAGGTGCGGCCGCG (SEQ ID NO: 12)

Fig. 6
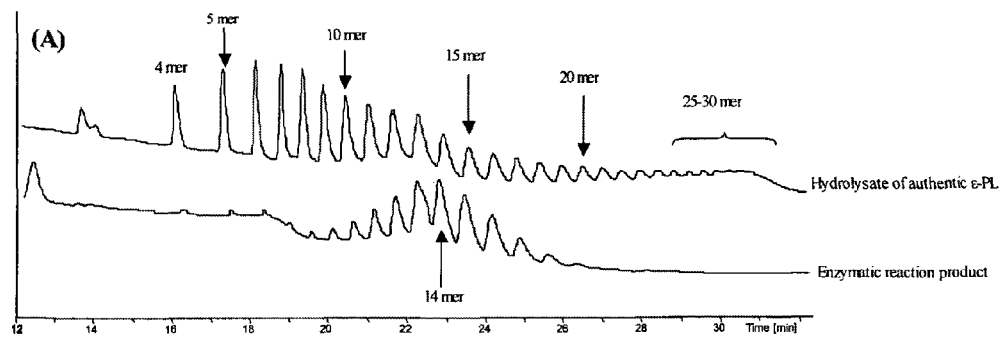
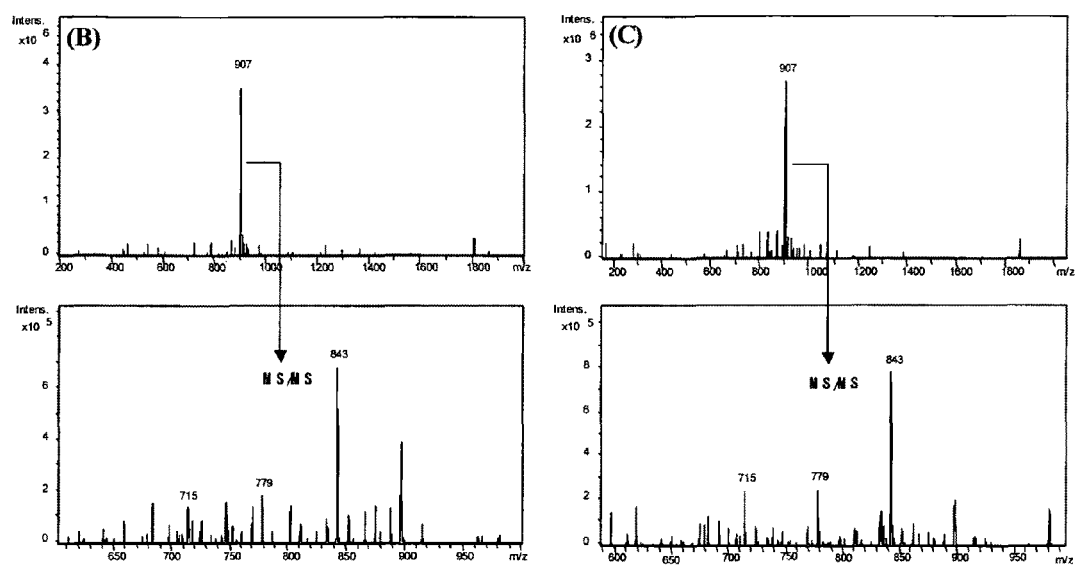
Fig. 7
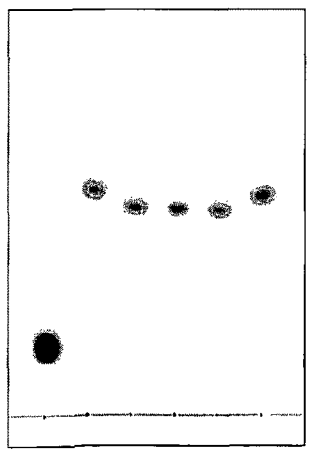

Fig. 11
A
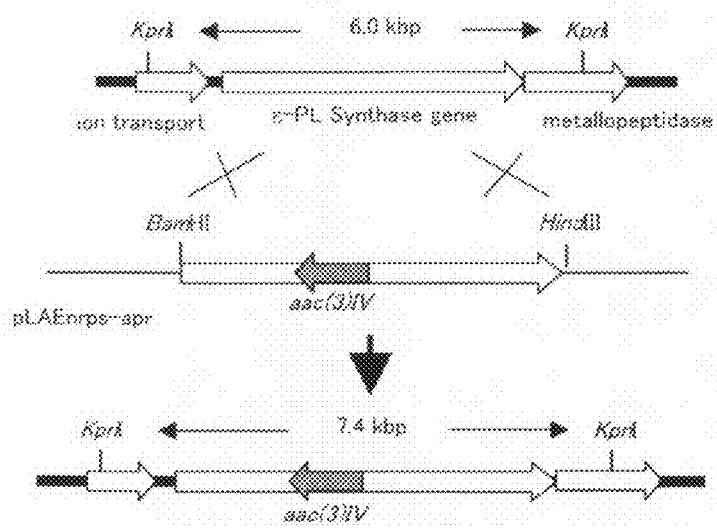
B
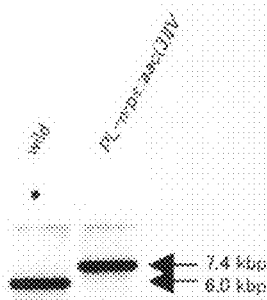
C
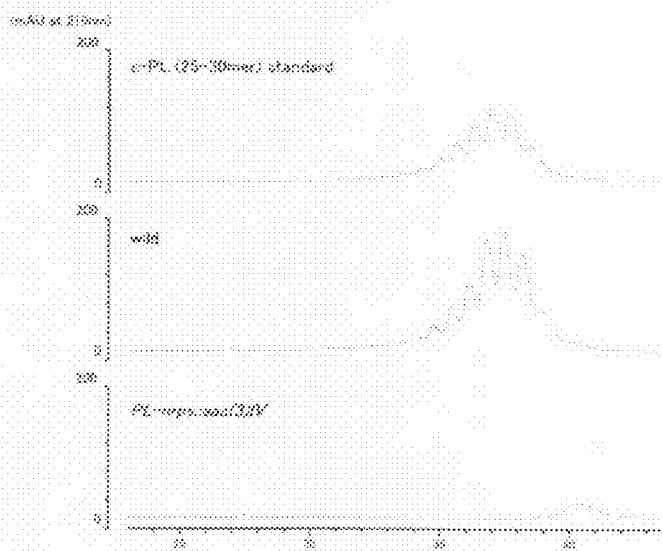

US 8,030,042 B2

POLYAMINO ACID SYNTHETASE AND GENE ENCODING THE SAME

This application is a U.S. national stage of International Application No. PCT/JP2008/057618 filed Apr. 18, 2008.

TECHNICAL FIELD

The present invention relates to a novel polyamino acid synthetase and a gene encoding the same.

BACKGROUND ART

As methods for synthesizing a polyamino acid, conventional methods using chemical synthesis, enzymatic synthesis or the like are known.

Recently, various bioactive peptides realizing high degree of social contribution have been found. Examples of methods for synthesizing such peptides include the chemical synthesis method and the enzymatic synthesis method. Using the latter method, peptides can be produced without any harmful chemicals, and problems of environmental burden, etc. can be overcome. In addition, cost reduction can also be expected.

As one of methods for enzymatically synthesizing a polyamino acid, a method for enzymatically synthesizing a nonprotein amino acid polymer consisting of an aspartic acid backbone and arginine side chains, cyanophycin (multi-L-arginyl-poly(L-aspartic acid)) is known (Non-patent documents 1 and 2). A method for enzymatically synthesizing poly-γ-glutamic acid has also been reported (Non-patent document 3).

However, since enzymatic synthesis of these polyamino acids is accomplished by the catalyst action of a multiple-enzyme system, it is difficult to control, and therefore it has not been applied to industrial production. Further, except for the cases of the enzymatic synthesis of cyanophycin and poly-γ-glutamic acid, there is no example of a peptide having a long chain (equal to or longer than a tripeptide) or amino acid homopolymer successfully synthesized enzymatically.

Regarding biosynthesis of an antibacterial polyamino acid ε-poly-L-lysine, biosynthesis using the microbial fermentation method has been reported (Non-patent document 4).

[Non-patent document 1] Eur. J. Biochem. 267, 5561-5570 (2000)
[Non-patent document 2] APPL. ENVIRON. MICROBIOL. Vol. 67, No. 5, May 2001, pp. 2176-2182
[Non-patent document 3] APPL. ENVIRON. MICROBIOL. Vol. 70, No. 7, July 2004, pp. 4249-4255
[Non-patent document 4] Agric. Biol. Chem. Vol. 45, 1981, pp. 2497-2502

DISCLOSURE OF THE INVENTION

Problems to be Solved by the Invention

Under the above-described circumstances, a method for efficiently producing any amino acid peptide with a longer chain or amino acid analog homopolymer is desired.

Means for Solving the Problems

The present inventors diligently made researches in order to meet the requirement and found a non-ribosomal peptide synthetase (NRPS) which catalyzes polymerization of L-lysine.

Accordingly, the present invention provides: a polyamino acid synthetase; a polynucleotide encoding the same; a vector comprising the polynucleotide; a method for producing the polyamino acid synthetase; a method for producing a polyamino acid using the polyamino acid synthetase; a primer comprising a partial sequence of the polynucleotide; a probe which can hybridize to the polynucleotide or a complementary sequence thereof; an antibody to the enzyme; a method for screening a polyamino acid synthetase using the primer or probe or antibody; and the like, as described below.

(1) A polynucleotide comprising any one of the following nucleotide sequences:
(i) a nucleotide sequence encoding a polyamino acid synthetase consisting of the amino acid sequence of SEQ ID NO: 2;
(ii) a nucleotide sequence encoding a polyamino acid synthetase consisting of an amino acid sequence having deletion, substitution, insertion and/or addition of at least one amino acid residue in the amino acid sequence of SEQ ID NO: 2;
(iii) a nucleotide sequence encoding a polyamino acid synthetase consisting of an amino acid sequence having at least 60% identity to the amino acid sequence of SEQ ID NO: 2;
(iv) the nucleotide sequence of SEQ ID NO: 1;
(v) a nucleotide sequence encoding a polyamino acid synthetase, which can hybridize to a nucleotide sequence complementary to the nucleotide sequence of SEQ ID NO: 1 under stringent hybridization conditions; and
(vi) a nucleotide sequence encoding a polyamino acid synthetase, which has at least 65% identity to the nucleotide sequence of SEQ ID NO: 1.

(1a) A polynucleotide comprising any one of the following nucleotide sequences:
(i) a nucleotide sequence encoding a polyamino acid synthetase consisting of an amino acid sequence having deletion, substitution, insertion and/or addition of one or several amino acid residues in the amino acid sequence of SEQ ID NO: 2;
(ii) a nucleotide sequence encoding a polyamino acid synthetase consisting of an amino acid sequence having at least 80% identity to the amino acid sequence of SEQ ID NO: 2; and
(iii) a nucleotide sequence encoding a polyamino acid synthetase, which can hybridize to a nucleotide sequence complementary to the nucleotide sequence of SEQ ID NO: 1 under highly stringent hybridization conditions.

(2) A polynucleotide comprising:
(i) a nucleotide sequence encoding a polyamino acid synthetase consisting of the amino acid sequence of SEQ ID NO: 2; or
(ii) the nucleotide sequence of SEQ ID NO: 1.

(3) The polynucleotide according to item (1) or (2), wherein the polyamino acid synthetase is a polylysine synthetase.

(4) The polynucleotide according to any one of items (1) to (3), which is a DNA or RNA.

(5) A polynucleotide comprising any one of the following nucleotide sequences:
(i) a nucleotide sequence encoding a condensation reaction catalytic domain or a subdomain thereof, which consists of the amino acid sequence of SEQ ID NO: 13, 15, 17 or 19;
(ii) a nucleotide sequence encoding a condensation reaction catalytic domain or a subdomain thereof, which consists of an amino acid sequence having deletion, substitution, insertion and/or addition of at least one amino acid residue in the amino acid sequence of SEQ ID NO: 13, 15, 17 or 19;
(iii) a nucleotide sequence encoding a condensation reaction catalytic domain or a subdomain thereof, which consists of an amino acid sequence having at least 60% identity to the amino acid sequence of SEQ ID NO: 13, 15, 17 or 19;
(iv) the nucleotide sequence of SEQ ID NO: 12, 14, 16 or 18;

(v) a nucleotide sequence encoding a condensation reaction catalytic domain or a subdomain thereof, which can hybridize to a nucleotide sequence complementary to the nucleotide sequence of SEQ ID NO: 12, 14, 16 or 18 under stringent hybridization conditions; and
(vi) a nucleotide sequence encoding a condensation reaction catalytic domain or a subdomain thereof, which has at least 65% identity to the nucleotide sequence of SEQ ID NO: 12, 14, 16 or 18.
(5a) A polynucleotide comprising any one of the following nucleotide sequences:
(i) a nucleotide sequence encoding a polyamino acid synthetase consisting of an amino acid sequence having deletion, substitution, insertion and/or addition of one or several amino acid residues in the amino acid sequence of SEQ ID NO: 13, 15, 17 or 19;
(ii) a nucleotide sequence encoding a polyamino acid synthetase consisting of an amino acid sequence having at least 80% identity to the amino acid sequence of SEQ ID NO: 13, 15, 17 or 19; and
(iii) a nucleotide sequence encoding a polyamino acid synthetase, which can hybridize to a nucleotide sequence complementary to the nucleotide sequence of SEQ ID NO: 12, 14, 16 or 18 under highly stringent hybridization conditions.
(6) A polynucleotide comprising:
(i) a nucleotide sequence encoding a condensation reaction catalytic domain or a subdomain thereof, which consists of the amino acid sequence of SEQ ID NO: 13, 15, 17 or 19; or
(ii) the nucleotide sequence of SEQ ID NO: 12, 14, 16 or 18.
(7) The polynucleotide according to item (5) or (6), which is a DNA or RNA.
(8) A polyamino acid synthetase comprising any one of the following amino acid sequences:
(i) the amino acid sequence of SEQ ID NO: 2;
(ii) an amino acid sequence having deletion, substitution, insertion and/or addition of at least one amino acid residue in the amino acid sequence of SEQ ID NO: 2; and
(iii) an amino acid sequence having at least 60% identity to the amino acid sequence of SEQ ID NO: 2.
(8a) A polyamino acid synthetase comprising:
(i) the amino acid sequence of SEQ ID NO: 2 having deletion, substitution, insertion and/or addition of one or several amino acid residues in the amino acid sequence of SEQ ID NO: 2; or
(ii) an amino acid sequence having at least 80% identity to the amino acid sequence of SEQ ID NO: 2.
(9) The polyamino acid synthetase according to item (8), which is a polylysine synthetase.
(10) A condensation reaction catalytic domain comprising any one of the following amino acid sequences:
(i) the amino acid sequence of SEQ ID NO: 13, 15, 17 or 19;
(ii) an amino acid sequence having deletion, substitution, insertion and/or addition of at least one amino acid residue in the amino acid sequence of SEQ ID NO: 13, 15, 17 or 19; and
(iii) an amino acid sequence having at least 60% identity to the amino acid sequence of SEQ ID NO: 13, 15, 17 or 19.
(10a) A condensation reaction catalytic domain comprising:
(i) an amino acid sequence having deletion, substitution, insertion and/or addition of one or several amino acid residues in the amino acid sequence of SEQ ID NO: 13, 15, 17 or 19; or
(ii) an amino acid sequence having at least 80% identity to the amino acid sequence of SEQ ID NO: 13, 15, 17 or 19.
(11) A polyamino acid synthetase comprising the condensation reaction catalytic domain according to item (10).
(12) The polyamino acid synthetase according to item (11), which is a polylysine synthetase.

(13) A recombinant vector comprising any one of the following nucleotide sequences:
(i) a nucleotide sequence encoding a polyamino acid synthetase consisting of the amino acid sequence of SEQ ID NO: 2;
(ii) a nucleotide sequence encoding a polyamino acid synthetase consisting of an amino acid sequence having deletion, substitution, insertion and/or addition of at least one amino acid residue in the amino acid sequence of SEQ ID NO: 2;
(iii) a nucleotide sequence encoding a polyamino acid synthetase consisting of an amino acid sequence having at least 60% identity to the amino acid sequence of SEQ ID NO: 2;
(iv) the nucleotide sequence of SEQ ID NO: 1;
(v) a nucleotide sequence encoding a polyamino acid synthetase, which can hybridize to a nucleotide sequence complementary to the nucleotide sequence of SEQ ID NO: 1 under stringent hybridization conditions; and
(vi) a nucleotide sequence encoding a polyamino acid synthetase, which has at least 65% identity to the nucleotide sequence of SEQ ID NO: 1.
(13a) A recombinant vector comprising any one of the following nucleotide sequences:
(i) a nucleotide sequence encoding a polyamino acid synthetase consisting of an amino acid sequence having deletion, substitution, insertion and/or addition of one or several amino acid residues in the amino acid sequence of SEQ ID NO: 2;
(ii) a nucleotide sequence encoding a polyamino acid synthetase consisting of an amino acid sequence having at least 80% identity to the amino acid sequence of SEQ ID NO: 2; and
(iii) a nucleotide sequence encoding a polyamino acid synthetase, which can hybridize to a nucleotide sequence complementary to the nucleotide sequence of SEQ ID NO: 1 under highly stringent hybridization conditions.
(14) A recombinant vector comprising:
(i) a nucleotide sequence encoding a polyamino acid synthetase consisting of the amino acid sequence of SEQ ID NO: 2; or
(ii) the nucleotide sequence of SEQ ID NO: 1.
(15) The recombinant vector according to item (13) or (14), wherein the polyamino acid synthetase is a polylysine synthetase.
(16) A recombinant vector comprising any one of the following nucleotide sequences:
(i) a nucleotide sequence encoding a condensation reaction catalytic domain or a subdomain thereof, which consists of the amino acid sequence of SEQ ID NO: 13, 15, 17 or 19;
(ii) a nucleotide sequence encoding a condensation reaction catalytic domain or a subdomain thereof, which consists of an amino acid sequence having deletion, substitution, insertion and/or addition of at least one amino acid residue in the amino acid sequence of SEQ ID NO: 13, 15, 17 or 19;
(iii) a nucleotide sequence encoding a condensation reaction catalytic domain or a subdomain thereof, which consists of an amino acid sequence having at least 60% identity to the amino acid sequence of SEQ ID NO: 13, 15, 17 or 19;
(iv) the nucleotide sequence of SEQ ID NO: 12, 14, 16 or 18;
(v) a nucleotide sequence encoding a condensation reaction catalytic domain or a subdomain thereof, which can hybridize to a nucleotide sequence complementary to the nucleotide sequence of SEQ ID NO: 12, 14, 16 or 18 under stringent hybridization conditions; and
(vi) a nucleotide sequence encoding a condensation reaction catalytic domain or a subdomain thereof, which has at least 65% identity to the nucleotide sequence of SEQ ID NO: 12, 14, 16 or 18.

(16a) A recombinant vector comprising any one of the following nucleotide sequences:
(i) a nucleotide sequence encoding a polyamino acid synthetase consisting of an amino acid sequence having deletion, substitution, insertion and/or addition of one or several amino acid residues in the amino acid sequence of SEQ ID NO: 13, 15, 17 or 19;
(ii) a nucleotide sequence encoding a polyamino acid synthetase consisting of an amino acid sequence having at least 80% identity to the amino acid sequence of SEQ ID NO: 13, 15, 17 or 19; and
(iii) a nucleotide sequence encoding a polyamino acid synthetase, which can hybridize to a nucleotide sequence complementary to the nucleotide sequence of SEQ ID NO: 12, 14, 16 or 18 under highly stringent hybridization conditions.
(17) A recombinant vector comprising:
(i) a nucleotide sequence encoding a condensation reaction catalytic domain or a subdomain thereof, which consists of the amino acid sequence of SEQ ID NO: 13, 15, 17 or 19; or
(ii) the nucleotide sequence of SEQ ID NO: 12, 14, 16 or 18.
(18) A transformant comprising the recombinant vector according to item (13), (15) or (16).
(19) A transformant comprising the recombinant vector according to item (14) or (17).
(20) A method for producing a polyamino acid synthetase using the recombinant vector according to item (13), (15) or (16) or the transformant according to item (18).
(21) A method for producing a polyamino acid synthetase using the recombinant vector according to item (14) or (17) or the transformant according to item (19).
(22) A method for producing a polyamino acid comprising the step of synthesizing the polyamino acid using a polyamino acid synthetase comprising any one of the following amino acid sequences:
(i) the amino acid sequence of SEQ ID NO: 2;
(ii) an amino acid sequence having deletion, substitution, insertion and/or addition of at least one amino acid residue in the amino acid sequence of SEQ ID NO: 2; and
(iii) an amino acid sequence having at least 60% identity to the amino acid sequence of SEQ ID NO: 2.
(22a) A method for producing a polyamino acid comprising the step of synthesizing the polyamino acid using a polyamino acid synthetase comprising:
(i) an amino acid sequence having deletion, substitution, insertion and/or addition of one or several amino acid residues in the amino acid sequence of SEQ ID NO: 2; or
(ii) an amino acid sequence having at least 80% identity to the amino acid sequence of SEQ ID NO: 2.
(23) A method for producing a polyamino acid comprising the step of synthesizing the polyamino acid using a polyamino acid synthetase comprising any one of the following amino acid sequences:
(i) the amino acid sequence of SEQ ID NO: 13, 15, 17 or 19;
(ii) an amino acid sequence having deletion, substitution, insertion and/or addition of at least one amino acid residue in the amino acid sequence of SEQ ID NO: 13, 15, 17 or 19; and
(iii) an amino acid sequence having at least 60% identity to the amino acid sequence of SEQ ID NO: 13, 15, 17 or 19.
(23a) A method for producing a polyamino acid comprising the step of synthesizing the polyamino acid using a polyamino acid synthetase comprising:
(i) an amino acid sequence having deletion, substitution, insertion and/or addition of one or several amino acid residues in the amino acid sequence of SEQ ID NO: 13, 15, 17 or 19; or
(ii) an amino acid sequence having at least 80% identity to the amino acid sequence of SEQ ID NO: 13, 15, 17 or 19.
(24) The method according to item (22) or (23), wherein the polyamino acid is polylysine.
(25) The method according to item (24), wherein the polylysine is $\epsilon$-poly-L-lysine.
(26) A primer consisting of a polynucleotide comprising at least 15 contiguous nucleotides in any one of the following nucleotide sequences or complementary sequences thereof:
(i) a nucleotide sequence encoding a polyamino acid synthetase consisting of the amino acid sequence of SEQ ID NO: 2 or a complementary sequence thereof;
(ii) a nucleotide sequence encoding a polyamino acid synthetase consisting of an amino acid sequence represented having deletion, substitution, insertion and/or addition of at least one amino acid residue in the amino acid sequence of SEQ ID NO: 2 or a complementary sequence thereof;
(iii) a nucleotide sequence encoding a polyamino acid synthetase consisting of an amino acid sequence having at least 60% identity to the amino acid sequence of SEQ ID NO: 2 or a complementary sequence thereof;
(iv) the nucleotide sequence of SEQ ID NO: 1 or a complementary sequence thereof;
(v) a nucleotide sequence encoding a polyamino acid synthetase, which can hybridize to a nucleotide sequence complementary to the nucleotide sequence of SEQ ID NO: 1 under stringent hybridization conditions, or a complementary sequence thereof; and
(vi) a nucleotide sequence encoding a polyamino acid synthetase, which has at least 65% identity to the nucleotide sequence of SEQ ID NO: 1, or a complementary sequence thereof.
(26a) A primer consisting of a polynucleotide comprising at least 15 contiguous nucleotides in any one of the following nucleotide sequences or complementary sequences thereof:
(i) a nucleotide sequence encoding a polyamino acid synthetase consisting of the amino acid sequence represented having deletion, substitution, insertion and/or addition of one or several amino acid residues in the amino acid sequence of SEQ ID NO: 2 or a complementary sequence thereof;
(ii) a nucleotide sequence encoding a polyamino acid synthetase consisting of an amino acid sequence having at least 80% identity to the amino acid sequence of SEQ ID NO: 2 or a complementary sequence thereof; and
(iii) a nucleotide sequence encoding a polyamino acid synthetase, which can hybridize to a nucleotide sequence complementary to the nucleotide sequence of SEQ ID NO: 1 under highly stringent hybridization conditions, or a complementary sequence thereof.
(27) A primer consisting of a polynucleotide comprising at least 15 contiguous nucleotides in any one of the following nucleotide sequences or complementary sequences thereof:
(i) a nucleotide sequence encoding a condensation reaction catalytic domain or a subdomain thereof, which consists of the amino acid sequence of SEQ ID NO: 13, 15, 17 or 19, or a complementary sequence thereof;
(ii) a nucleotide sequence encoding a condensation reaction catalytic domain or a subdomain thereof, which consists of an amino acid sequence having deletion, substitution, insertion and/or addition of at least one amino acid residue in the amino acid sequence of SEQ ID NO: 13, 15, 17 or 19, or a complementary sequence thereof;
(iii) a nucleotide sequence encoding a condensation reaction catalytic domain or a subdomain thereof, which consists of an amino acid sequence having at least 60% identity to the amino acid sequence of SEQ ID NO: 13, 15, 17 or 19, or a complementary sequence thereof;

(iv) the nucleotide sequence of SEQ ID NO: 12, 14, 16 or 18 or a complementary sequence thereof;
(v) a nucleotide sequence encoding a condensation reaction catalytic domain or a subdomain thereof, which can hybridize to a nucleotide sequence complementary to the nucleotide sequence of SEQ ID NO: 12, 14, 16 or 18 under stringent hybridization conditions, or a complementary sequence thereof; and
(vi) a nucleotide sequence encoding a condensation reaction catalytic domain or a subdomain thereof, which has at least 65% identity to the nucleotide sequence of SEQ ID NO: 12, 14, 16 or 18, or a complementary sequence thereof.
(27a) A primer consisting of a polynucleotide comprising at least 15 contiguous nucleotides in any one of the following nucleotide sequences or complementary sequences thereof:
(i) a nucleotide sequence encoding a polyamino acid synthetase consisting of an amino acid sequence having deletion, substitution, insertion and/or addition of one or several amino acid residues in the amino acid sequence of SEQ ID NO: 13, 15, 17 or 19 or a complementary sequence thereof;
(ii) a nucleotide sequence encoding a polyamino acid synthetase consisting of an amino acid sequence having at least 80% identity to the amino acid sequence of SEQ ID NO: 13, 15, 17 or 19 or a complementary sequence thereof; and
(iii) a nucleotide sequence encoding a polyamino acid synthetase, which can hybridize to a nucleotide sequence complementary to the nucleotide sequence of SEQ ID NO: 12, 14, 16 or 18 under highly stringent hybridization conditions, or a complementary sequence thereof.
(28) A primer consisting of a polynucleotide comprising at least 15 contiguous nucleotides in any one of the following nucleotide sequences or complementary sequences thereof:
(i) a nucleotide sequence encoding a polyamino acid synthetase consisting of the amino acid sequence of SEQ ID NO: 2 or a complementary sequence thereof;
(ii) the nucleotide sequence of SEQ ID NO: 1 or a complementary sequence thereof;
(iii) a nucleotide sequence encoding a condensation reaction catalytic domain or a subdomain thereof, which consists of the amino acid sequence of SEQ ID NO: 13, 15, 17 or 19, or a complementary sequence thereof; and
(iv) the nucleotide sequence of SEQ ID NO: 12, 14, 16 or 18 or a complementary sequence thereof.
(29) A polynucleotide probe consisting of a nucleotide sequence of at least 15 nucleotides, which can hybridize, under stringent hybridization conditions, to any one of the following nucleotide sequences:
(i) a nucleotide sequence encoding a polyamino acid synthetase consisting of the amino acid sequence of SEQ ID NO: 2 or a complementary sequence thereof;
(ii) a nucleotide sequence encoding a polyamino acid synthetase consisting of an amino acid sequence represented having deletion, substitution, insertion and/or addition of at least one amino acid residue in the amino acid sequence of SEQ ID NO: 2 or a complementary sequence thereof;
(iii) a nucleotide sequence encoding a polyamino acid synthetase consisting of an amino acid sequence having at least 60% identity to the amino acid sequence of SEQ ID NO: 2 or a complementary sequence thereof;
(iv) the nucleotide sequence of SEQ ID NO: 1 or a complementary sequence thereof;
(v) a nucleotide sequence encoding a polyamino acid synthetase, which can hybridize to a nucleotide sequence complementary to the nucleotide sequence of SEQ ID NO: 1 under stringent hybridization conditions, or a complementary sequence thereof; and
(vi) a nucleotide sequence encoding a polyamino acid synthetase, which has at least 65% identity to the nucleotide sequence of SEQ ID NO: 1, or a complementary sequence thereof.
(29a) A polynucleotide probe consisting of a nucleotide sequence of at least 15 nucleotides, which can hybridize, under highly stringent hybridization conditions, to any one of the following nucleotide sequences:
(i) a nucleotide sequence encoding a polyamino acid synthetase consisting of an amino acid sequence having deletion, substitution, insertion and/or addition of one or several amino acid residues in the amino acid sequence of SEQ ID NO: 2 or a complementary sequence thereof;
(ii) a nucleotide sequence encoding a polyamino acid synthetase consisting of an amino acid sequence having at least 80% identity to the amino acid sequence of SEQ ID NO: 2 or a complementary sequence thereof; and
(iii) a nucleotide sequence encoding a polyamino acid synthetase, which can hybridize to a nucleotide sequence complementary to the nucleotide sequence of SEQ ID NO: 1 under highly stringent hybridization conditions, or a complementary sequence thereof.
(30) A polynucleotide probe consisting of a nucleotide sequence of at least 15 nucleotides, which can hybridize, under stringent hybridization conditions, to any one of the following nucleotide sequences:
(i) a nucleotide sequence encoding a condensation reaction catalytic domain or a subdomain thereof, which consists of the amino acid sequence of SEQ ID NO: 13, 15, 17 or 19, or a complementary sequence thereof;
(ii) a nucleotide sequence encoding a condensation reaction catalytic domain or a subdomain thereof, which consists of an amino acid sequence having deletion, substitution, insertion and/or addition of at least one amino acid residue in the amino acid sequence of SEQ ID NO: 13, 15, 17 or 19, or a complementary sequence thereof;
(iii) a nucleotide sequence encoding a condensation reaction catalytic domain or a subdomain thereof, which consists of an amino acid sequence having at least 60% identity to the amino acid sequence of SEQ ID NO: 13, 15, 17 or 19, or a complementary sequence thereof;
(iv) the nucleotide sequence of SEQ ID NO: 12, 14, 16 or 18 or a complementary sequence thereof;
(v) a nucleotide sequence encoding a condensation reaction catalytic domain or a subdomain thereof, which can hybridize to a nucleotide sequence complementary to the nucleotide sequence of SEQ ID NO: 12, 14, 16 or 18 under stringent hybridization conditions, or a complementary sequence thereof; and
(vi) a nucleotide sequence encoding a condensation reaction catalytic domain or a subdomain thereof, which has at least 65% identity to the nucleotide sequence of SEQ ID NO: 12, 14, 16 or 18, or a complementary sequence thereof.
(30a) A polynucleotide probe consisting of a nucleotide sequence of at least 15 nucleotides, which can hybridize, under highly stringent hybridization conditions, to any one of the following nucleotide sequences:
(i) a nucleotide sequence encoding a polyamino acid synthetase consisting of an amino acid sequence having deletion, substitution, insertion and/or addition of one or several amino acid residues in the amino acid sequence of SEQ ID NO: 13, 15, 17 or 19 or a complementary sequence thereof;
(ii) a nucleotide sequence encoding a polyamino acid synthetase consisting of an amino acid sequence having at least 80% identity to the amino acid sequence of SEQ ID NO: 13, 15, 17 or 19 or a complementary sequence thereof; and (iii) a nucleotide sequence encoding a polyamino acid synthetase, which can hybridize to a nucleotide sequence complementary to the nucleotide sequence of SEQ ID NO: 12, 14, 16 or 18 under highly stringent hybridization conditions, or a complementary sequence thereof.

(31) A polynucleotide probe consisting of a nucleotide sequence of at least 15 nucleotides, which can hybridize, under stringent hybridization conditions, to any one of the following nucleotide sequences:
(i) a nucleotide sequence encoding a polyamino acid synthetase consisting of the amino acid sequence of SEQ ID NO: 2 or a complementary sequence thereof;
(ii) the nucleotide sequence of SEQ ID NO: 1 or a complementary sequence thereof;
(iii) a nucleotide sequence encoding a condensation reaction catalytic domain or a subdomain thereof, which consists of the amino acid sequence of SEQ ID NO: 13, 15, 17 or 19, or a complementary sequence thereof; and
(iv) the nucleotide sequence of SEQ ID NO: 12, 14, 16 or 18 or a complementary sequence thereof.

(32) An antibody which specifically binds to a polyamino acid synthetase comprising any one of the following amino acid sequences:
(i) the amino acid sequence of SEQ ID NO: 2;
(ii) an amino acid sequence having deletion, substitution, insertion and/or addition of at least one amino acid residue in the amino acid sequence of SEQ ID NO: 2; and
(iii) an amino acid sequence having at least 60% identity to the amino acid sequence of SEQ ID NO: 2.

(33) An antibody which specifically binds to: a condensation reaction catalytic domain or a subdomain thereof, which comprises any one of the following amino acid sequences:
(i) the amino acid sequence of SEQ ID NO: 13, 15, 17 or 19;
(ii) an amino acid sequence having deletion, substitution, insertion and/or addition of at least one amino acid residue in the amino acid sequence of SEQ ID NO: 13, 15, 17 or 19; and
(iii) an amino acid sequence having at least 60% identity to the amino acid sequence of SEQ ID NO: 13, 15, 17 or 19; or a polyamino acid synthetase comprising the domain.

(34) A method for screening a polynucleotide encoding a polyamino acid synthetase using the primer according to any one of items (26) to (28).

(35) The method according to item (34), further using the probe according to any one of items (29) to (31).

(36) A method for screening a polyamino acid synthetase using the antibody according to item (32) or (33).

ADVANTAGEOUS EFFECT OF THE INVENTION

According to the present invention, a polyamino acid (e.g., ε-poly-L-lysine) can be enzymatically synthesized. The enzymatic synthesis method can save more energy than the microbial fermentation method and the chemical synthesis method, and can suppress undesired side reactions. Therefore, the enzymatic synthesis method has the advantage that it is possible to produce a highly-pure polyamino acid. Since many peptides and polyamino acids produced by microorganisms including cyanophycin and poly-γ-glutamic acid are biosynthesized by the catalyst action of a multiple-enzyme system, it is difficult to carry out industrial production thereof enzymatically. However, since the polyamino acid synthetase of the present invention is a single thiotemplate type non-ribosomal peptide synthetase (NRPS), it also has the advantage that it can be easily controlled and is suitable for enzymatic industrial production.

Thus, the present invention can provide a method for producing a polyamino acid more efficiently than conventional methods. Moreover, when using the polynucleotide-containing recombinant vector and the transformant of the present invention, it is possible to apply the present invention to biosynthesis of various useful polyamino acids.

BRIEF DESCRIPTION OF THE DRAWINGS

FIG. 1A is a diagram showing the multi-module structure of the conventional NRPS. FIG. 1B is a diagram showing the single-module structure of a polyamino acid synthetase in one embodiment of the present invention.

FIG. 2 A-D show the amino acid sequences of the condensation reaction catalytic domain and subdomains thereof positioned at the C-terminal side of the polyamino acid synthetase of the present invention. In the figures, "tmr" means a transmembrane region.

FIG. 3 A-C show the DNA sequences of the subdomains of the condensation reaction catalytic domain positioned at the C-terminal side of the polyamino acid synthetase of the present invention.

FIG. 3D shows the DNA sequence of the condensation reaction catalytic domain positioned at the C-terminal side of the polyamino acid synthetase of the present invention. In the figure, "tmr" means a transmembrane region.

FIG. 6A is a graph showing separation pattern of liquid chromatography (LC). FIG. 6B is a graph showing the result of mass analysis of 14 mer of a product obtained by hydrolyzing the ε-poly-L-lysine standard product with hydrochloric acid. FIG. 6C is a graph showing the result of mass analysis of 14 mer of enzymatically-synthesized ε-poly-L-lysine.

FIG. 7 is a graph showing the analysis results of thin-layer chromatography of a product obtained by hydrolyzing a DNP-lated ε-poly-L-lysine with hydrochloric acid. Lane 1: L-lysine, Lane 2: a product produced by hydrolyzing a DNP-lated α-poly-L-lysine (Wako Pure Chemical Industries, Ltd.) with hydrochloric acid, Lane 3: a product produced by hydrolyzing a DNP-lated ε-poly-L-lysine standard product (Chisso corporation) with hydrochloric acid, Lane 4: a product produced by hydrolyzing a DNP-lated enzymatically-synthesized ε-poly-L-lysine with hydrochloric acid, Lane 5: $N^{\alpha}$-2,4-DNP-L-lysine, Lane 6: $N^{\epsilon}$-2,4-DNP-L-lysine.

FIG. 11 shows a method for disrupting the ε-poly-L-lysine biosynthetic enzyme gene and influence thereof. (A) schematically shows a procedure for preparing a gene-disrupted strain using a plasmid for disruption, pLAEnrps-apr. (B) shows that disruption of the ε-poly-L-lysine biosynthetic enzyme gene was confirmed by genomic Southern hybridization. (C) shows the results of confirmation of the productivity of ε-poly-L-lysine using HPLC after culturing a disrupted strain obtained in a production medium.

BEST MODE FOR CARRYING OUT THE INVENTION

Figure 4:
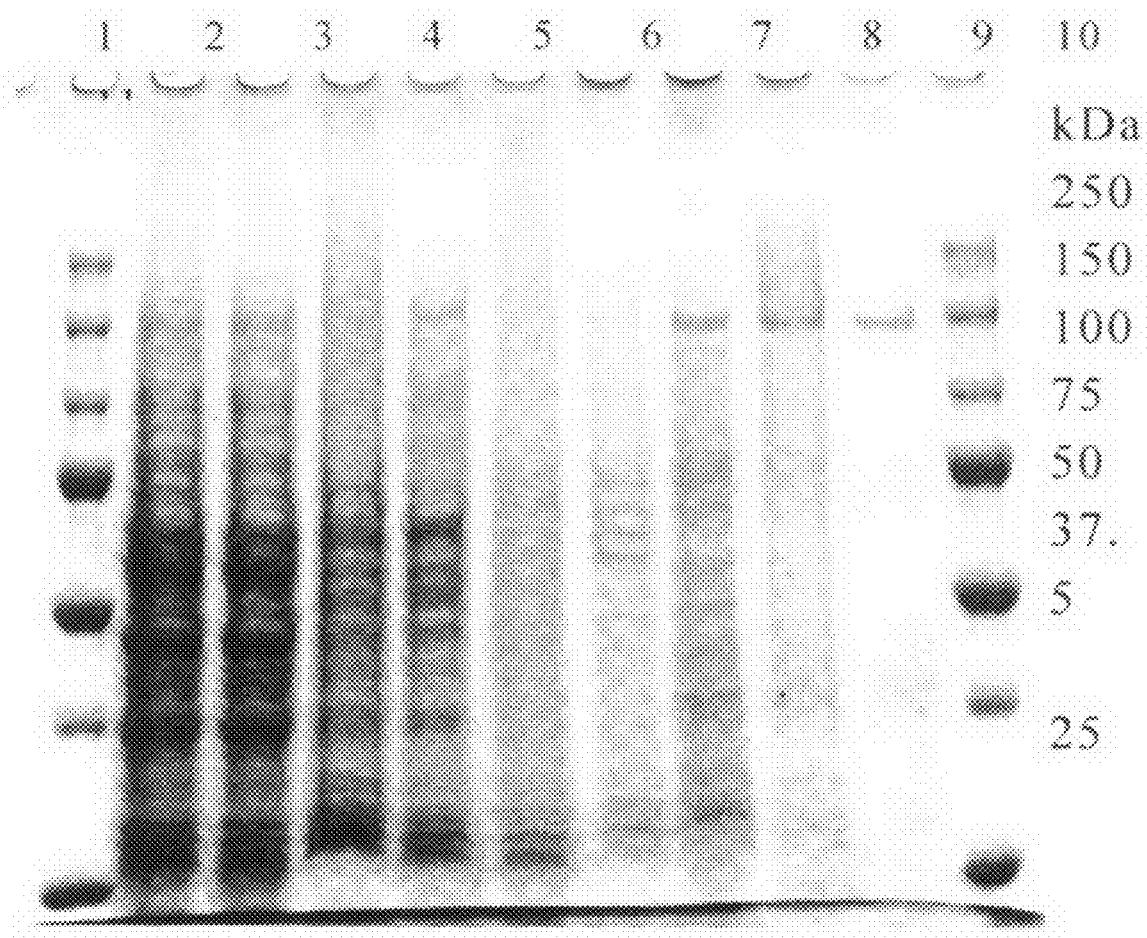
FIG. 4 is a photograph showing the results of SDS-PAGE analysis of respective fractions in the purification process of the ε-poly-L-lysine biosynthetic enzyme of the present invention. Lanes 1 and 11: molecular-weight marker (recombinant protein, Bio-Rad), Lane 2: crude enzyme solution, Lane 3: soluble fraction, Lane 4: cell membrane fraction, Lane 5: salt-soluble fraction, Lane 6: salt-washed cell membrane fraction, Lane 7: NP-40-soluble fraction, Lane 8: eluted fraction from DEAE TOYOPEARL column, Lane 9: eluted fraction from AF-Blue TOYOPEARL column, Lane 10: eluted fraction from Sephacryl S-300 column.

The present inventors isolated and purified a membrane-bound ε-poly-L-lysine biosynthetic enzyme from a ε-poly-L-lysine producing bacterium, *Streptomyces albulus* strain IFO14147, and determined the amino acid sequence thereof (SEQ ID NO: 2) and the nucleotide sequence (SEQ ID NO: 1) of the gene encoding the amino acid sequence. When the amino acid sequence and the DNA sequence of the ε-poly-L-lysine biosynthetic enzyme of the present invention were subjected to homology search using the NCBI sequence database, the following results were obtained: regarding the amino acid sequence, the highest identity was 54.1% (77.3% similarity); regarding the DNA sequence, the highest identity was 64.2%; and regarding a local region (region of important domain (positions 470 to 795)), a sequence having at least 80% identity was found.

According to one embodiment of the present invention, a polylysine biosynthetic enzyme and a gene encoding the same are provided. The enzyme of the present invention is the only membrane enzyme as NRPS which had not been known. Therefore, according to another embodiment of the present invention, a membrane-bound NRPS is provided.

Many peptides produced by microorganisms having physiological activity, which can be applied to pharmaceutical agents, have been found. Many of these peptides are biosynthesized by the catalyst action of a multi-module conjugate enzyme, which is called "non-ribosomal peptide synthetase (NRPS)".

A NRPS is constituted by a module as a base unit, which consists of: an adenylation domain (A-domain) which catalyzes activation of amino acids; a domain called peptidyl carrier domain or thiolation domain (PCP-Domain) which bonds an amino acid or peptide intermedite molecule; a condensation domain (C-Domain) which catalyzes condensation of a substrate; and a thioesterase domain (TE-Domain) which is involved in circularization of a peptide and isolation of a peptide from a NRPS that are final steps of biosynthesis (FIG. 1). To a thiolation domain, a 4'-phosphopantetheine (P-pant) arm, which is a cofactor for bonding an amino acid or intermediate, binds (not shown). There is a case where a domain which is involved in modification of peptide such as epimerization and methylation is further added to the module.

Each of the domains of NRPS has a plurality of regions which are commonly conserved in peptide synthetases. For example, a microcystin biosynthesis gene is cloned using, as a probe, a fragment obtained by PCR amplification based on the nucleotide sequence information of such regions.

When the polylysine biosynthetic enzyme of the present invention was analyzed using an analysis tool which performs function prediction based on structure comparison with a protein having a similar domain structure in a database such as the Conserved Domain Database on the NCBI website, it was confirmed that A-Domain and PCP-Domain bonding a peptide intermediate molecule were present at the N-terminus like many other NRPSs. However, it was revealed that a region of about 700 amino acid residues at the C-terminal side is a novel (unknown) domain, which does not have homology to conventional C-Domain or TE-Domain. Further, conventional NRPSs are multi-module conjugate enzymes, but it was strongly suggested that the enzyme of the present invention is a single-module single enzyme based on the domain structure analysis and the result of enzyme purification. Thus, in the case of the enzyme of the present invention, polyamino acid synthesis is accomplished only using the single module, and therefore, it is thought that the novel domain consisting of 700 amino acid residues at the C-terminal side catalyzes a "repeated condensation reaction". Accordingly, in one embodiment of the present invention, a polylysine biosynthetic enzyme comprising the above-described region of about 700 amino acid residues at the C-terminal side is provided.

Moreover, conventional NRPSs are localized in cytoplasm (soluble fraction), but the present enzyme is the only membrane enzyme which had not been known as NRPS, and it was thought that the membrane-bound (transmembrane) region is present in the novel domain at the C-terminus. Therefore, the C-terminal novel domain of the enzyme of the present invention was analyzed in further detail using an analysis tool which performs prediction of the secondary structure of a membrane protein or the like based on an amino acid sequence. According to SOSUI, available on the Nagoya University website, as predicted, 6 regions which are assumed to be transmembrane regions were confirmed in the C-terminal novel domain, and the possibility that the novel domain which is thought to catalyze the "repeated condensation reaction" is constituted by 3 subdomains, IC1, IC2 and IC3-Domains was suggested (FIG. 1B and FIG. 2). Therefore, in another embodiment of the present invention, a polylysine biosynthetic enzyme comprising any one of the above-described 3 subdomains is provided.

Hereinafter, the present invention will be described in detail.

1. Polyamino Acid Synthetase of the Present Invention and Polynucleotide Encoding the Same The present invention provides a polyamino acid synthetase and a gene encoding the same. Specifically, the present invention provides a polyamino acid synthetase comprising any one of the following amino acid sequences: (i) the amino acid sequence of SEQ ID NO: 2; (ii) an amino acid sequence having deletion, substitution, insertion and/or addition of at least one amino acid residue in the amino acid sequence of SEQ ID NO: 2; and (iii) an amino acid sequence having at least 60% identity to the amino acid sequence of SEQ ID NO: 2.

The present invention also provides a polynucleotide comprising a nucleotide sequence encoding a polyamino acid synthetase consisting of any one of the following amino acid sequences: (i) the amino acid sequence of SEQ ID NO: 2; (ii) an amino acid sequence having deletion, substitution, insertion and/or addition of at least one amino acid residue in the amino acid sequence of SEQ ID NO: 2; and (iii) an amino acid sequence having at least 60% identity to the amino acid sequence of SEQ ID NO: 2.

The present invention also provides a polynucleotide comprising any one of the following nucleotide sequences: (i) the nucleotide sequence of SEQ ID NO: 1; (ii) a nucleotide sequence encoding a polyamino acid synthetase, which can hybridize to a nucleotide sequence complementary to the nucleotide sequence of SEQ ID NO: 1 under stringent hybridization conditions; and (iii) a nucleotide sequence encoding a polyamino acid synthetase, which has at least 65% identity to the nucleotide sequence of SEQ ID NO: 1.

In a preferred embodiment of the present invention, the above-described polyamino acid synthetase is a polylysine synthetase, and more preferably a ε-poly-L-lysine synthetase. The above-described polynucleotide may be a DNA or RNA, and preferably DNA.

In the present specification, the "polyamino acid synthetase of the present invention" includes not only (i) a polyamino acid synthetase consisting of the amino acid sequence of SEQ ID NO: 2, but also a polyamino acid synthetase consisting of an amino acid sequence having high homology to the amino acid sequence of SEQ ID NO: 2, e.g., (ii) a polyamino acid synthetase consisting of an amino acid sequence having deletion, substitution, insertion and/or addition of at least one amino acid residue in the amino acid sequence of SEQ ID NO: 2, and (iii) a polyamino acid synthetase consisting of an amino acid sequence having high identity (e.g., at least about 60%) to the amino acid sequence of SEQ ID NO: 2. Further, the enzyme activity of the polyamino acid synthetase can be measured and/or confirmed using, for example, the method of Kawai et al. (Biochem Biophys Res Commun. 2003 Nov. 21; 311(3): 635-40).

Examples of the "polyamino acid synthetase consisting of an amino acid sequence having deletion, substitution, insertion and/or addition of at least one amino acid residue in the amino acid sequence of SEQ ID NO: 2" include polyamino acid synthetases consisting of an amino acid sequence having deletion, substitution, insertion and/or addition of, for example, 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6 (1 to several), 1 to 5, 1 to 4, 1 to 3, 1 to 2, or 1 amino acid residue in the amino acid sequence of SEQ ID NO: 2. In general, the number of the above-described amino acid residues to be deleted, substituted, inserted and/or added is preferably smaller.

Examples of the "polyamino acid synthetase consisting of an amino acid sequence having high identity to the amino acid sequence of SEQ ID NO: 2" include polyamino acid synthetases consisting of an amino acid sequence having at least about 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to the amino acid sequence of SEQ ID NO: 2. In general, the bigger the numerical value of the above-described identity, the more preferable it is. In the present specification, the term "identity" is distinguished from the term "homology". For example, when referring to the homology between amino acid sequences, amino acids having similar properties (e.g., glutamic acid and aspartic acid) are regarded as belonging to the same group, but when referring to the identity, such amino acids are distinguished from each other. That is, identity means consistency.

In the present specification, when describing that a nucleotide sequence "hybridizes", it means that a double strand is formed in the case in which complementation between nucleotide sequences is high. Usually, a double strand is designed so that nucleic acids thereof are complementary to each other. However, one or several (e.g., 2 to 3) nucleic acid mismatches may be included as necessary (as long as there is no problem in view of its purpose when using the nucleic acid for detection, for example). The number of mismatches which may exist may vary depending on, for example, required accuracy of detection and the length of a nucleotide sequence (or base sequence or nucleic acid (sequence) or polynucleotide). Note that those skilled in the art know well that the case where a mismatch exists can be eliminated and the number of mismatches acceptable can be adjusted by suitably changing the conditions for the hybridization of a nucleotide sequence to another nucleotide sequence to which the nucleotide sequence hybridizes.

Examples of hybridization methods which can be employed include the colony hybridization method, plaque hybridization method and Southern hybridization method (for example, see Molecular Cloning 3rd Ed., Current Protocols in Molecular Biology, John Wiley & Sons 1987-1997).

In the present specification, the "stringent hybridization conditions" may be any of low stringent conditions, moderately stringent conditions and highly stringent conditions. The "low stringent conditions" are, for example: 5×SSC; 5×Denhart solution; 0.5% (w/v) SDS; 50% (w/v) formamide; and 32° C. The "moderately stringent conditions" are, for example: 5×SSC; 5×Denhart solution; 0.5% (w/v) SDS; 50% (w/v) formamide; and 42° C. The "highly stringent conditions" are, for example: 5×SSC; 5×Denhart solution; 0.5% (w/v) SDS; 50% (w/v) formamide; and 50° C. Under these conditions, it is expected that a DNA having high identity can be efficiently obtained at a higher temperature. However, it is thought that hybridization stringency is affected by a plurality of factors such as temperature, nucleic acid concentration, nucleic acid length, ion strength, time, and salt concentration. Those skilled in the art would be able to realize similar stringency by suitably selecting these elements.

When using a commercially available kit for hybridization, for example, Alkphos Direct Labelling Reagents (manufactured by Amersham Pharmacia) can be used. In this case, according to a protocol attached to the kit, incubation with a labeled probe is performed overnight, and thereafter a membrane is washed with a primary wash buffer containing 0.1% (w/v) SDS at 55° C., thereby detecting a polynucleotide which hybridizes.

Examples of the "nucleotide sequence which can hybridize, under stringent hybridization conditions," to a desired nucleotide sequence (e.g., the nucleotide sequence of SEQ ID NO: 1) include nucleotide sequences having at least about 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to the desired nucleotide sequence when performing calculation by a homology (or identity) search software such as FASTA and BLAST using default parameters.

The identity of an amino acid sequence or nucleotide sequence can be determined using the BLAST algorithm of Karlin & Altschul (Proc. Natl. Acad. Sci. USA, 87, 2264-2268, 1990; and Proc. Natl. Acad. Sci. USA, 90, 5873, 1993). Programs called BLASTN and BLASTX based on the BLAST algorithm have been developed (Altschul S F, et al.: J Mol Biol 215: 403, 1990). When analyzing a nucleotide sequence using BLASTN, parameters are set, for example, as follows: score=100; and wordlength=12. When analyzing an amino acid sequence using BLASTX, parameters are set, for example, as follows: score=50; and wordlength=3. When using BLAST and Gapped BLAST program, default parameters of each of the programs can be used.

2. C-Terminal Domain of the Polyamino Acid Synthetase of the Present Invention and Polynucleotide Encoding the Same In the case of conventional NRPSs, peptides or polyamino acids are polymerized by the catalyst action of a multi-module conjugate enzyme, but it is strongly suggested that the polyamino acid synthetase of the present invention is a single-module single enzyme based on the domain structure analysis and the result of enzyme purification (see FIGS. 1A and B). In the case of the polyamino acid synthetase of the present invention, since the polyamino acid synthesis is accomplished only using the single module, it is thought that the novel domain of the present invention consisting of about 700 amino acid residues at the C-terminal side catalyzes a "repeated condensation reaction". Further, when analysis was carried out using an analyzing tool for protein structure such as CDD, it was inferred that 3 subdomains exist at the above-described C-terminal domain and that 6 transmembrane regions exist at boundaries between the subdomains (see FIG. 1B).

Therefore, according to another embodiment of the present invention, a C-terminal domain comprising about 700 amino acid residues at the C-terminal side of the polyamino acid synthetase of the present invention (hereinafter referred to as a "condensation reaction catalytic domain"), a polyamino acid synthetase comprising the condensation reaction catalytic domain, and a polynucleotide comprising a nucleotide sequence encoding the domain or the enzyme are provided. When just describing "condensation reaction catalytic domain" in this specification, it means a condensation reaction catalytic domain of a polyamino acid synthetase.

The condensation reaction catalytic domain of the present invention is a functional domain consisting of a polypeptide comprising an amino acid sequence corresponding to a region generally spanning over positions 611 to 1319 of the amino acid sequence of the $\epsilon$-poly-L-lysine synthetase of the present invention represented by SEQ ID NO: 2 (positions 1831 to 3957 of the nucleotide sequence), as typically shown in FIGS. 2A-2D and 3A-3D. The amino acid sequence thereof and the nucleotide sequence encoding the same are represented by SEQ ID NO: 13 and SEQ ID NO: 12, respectively. Further, 3 smaller domains (IC1, IC2 and IC3-Domains) constituting the domain typically correspond to a region of about positions 676 to 847, a region of about positions 914 to 1083, and a region of about positions 1147 to 1299 of the amino acid sequence of the $\epsilon$-poly-L-lysine synthetase of the present invention represented by SEQ ID NO: 2, respectively (positions 2026 to 2541, positions 2740 to 3249 and positions 3439 to 3897 of the nucleotide sequence, respectively). The amino acid sequences of these 3 subdomains are represented by SEQ ID NO: 15, SEQ ID NO: 17 and SEQ ID NO: 19, respectively, and the nucleotide sequences encoding these amino acid sequences are represented by SEQ ID NO: 14, SEQ ID NO: 16 and SEQ ID NO: 18, respectively.

In this specification, the "condensation reaction catalytic domain of the present invention" includes not only (i) a condensation reaction catalytic domain consisting of the amino acid sequence of SEQ ID NO: 13, but also a condensation reaction catalytic domain consisting of an amino acid sequence having high homology to the amino acid sequence of SEQ ID NO: 13, e.g., (ii) a condensation reaction catalytic domain consisting of an amino acid sequence having deletion, substitution, insertion and/or addition of at least one amino acid residue in the amino acid sequence of SEQ ID NO: 13, and (iii) a condensation reaction catalytic domain consisting of an amino acid sequence having high identity (e.g., at least about 60%) to the amino acid sequence of SEQ ID NO: 13.

In this specification, the "subdomain of the present invention (condensation reaction catalytic domain)" includes not only (i) a subdomain (of the condensation reaction catalytic domain) consisting of the amino acid sequence of SEQ ID NO: 15, 17 or 19, but also a subdomain (of the condensation reaction catalytic domain) consisting of an amino acid sequence having high homology to the amino acid sequence of SEQ ID NO: 15, 17 or 19, e.g., (ii) a subdomain (of the condensation reaction catalytic domain) consisting of an amino acid sequence having deletion, substitution, insertion and/or addition of at least one amino acid residue in the amino acid sequence of SEQ ID NO: 15, 17 or 19, and (iii) a subdomain (of the condensation reaction catalytic domain) consisting of an amino acid sequence having high identity (e.g., at least about 60%) to the amino acid sequence of SEQ ID NO: 15, 17 or 19.

Therefore, the present invention also provides: a condensation reaction catalytic domain or a subdomain thereof which comprises any one of the following amino acid sequences: (i) the amino acid sequence of SEQ ID NO: 13, 15, 17 or 19; (ii) an amino acid sequence having deletion, substitution, insertion and/or addition of at least one amino acid residue in the amino acid sequence of SEQ ID NO: 13, 15, 17 or 19; and (iii) an amino acid sequence having at least 60% identity to the amino acid sequence of SEQ ID NO: 13, 15, 17 or 19; and a polyamino acid synthetase comprising the domain. It can be confirmed whether or not a condensation reaction has occurred, for example, by detecting a polymerized product (enzymatic reaction product) utilizing LC-MS/MS or the like.

The present invention also provides a polynucleotide comprising a nucleotide sequence encoding: a condensation reaction catalytic domain or a subdomain thereof, which consists of any one of the following amino acid sequences: (i) the amino acid sequence of SEQ ID NO: 13, 15, 17 or 19; (ii) an amino acid sequence having deletion, substitution, insertion and/or addition of at least one amino acid residue in the amino acid sequence of SEQ ID NO: 13, 15, 17 or 19; and (iii) an amino acid sequence having at least 60% identity to the amino acid sequence of SEQ ID NO: 13, 15, 17 or 19; or a polyamino acid synthetase comprising the domain.

The present invention also provides a polynucleotide comprising any one of the following nucleotide sequences: (i) the nucleotide sequence of SEQ ID NO: 12, 14, 16 or 18; (ii) a nucleotide sequence encoding a condensation reaction catalytic domain or a subdomain thereof, which can hybridize to a nucleotide sequence complementary to the nucleotide sequence of SEQ ID NO: 12, 14, 16 or 18 under stringent hybridization conditions; and (iii) a nucleotide sequence encoding a condensation reaction catalytic domain or a subdomain thereof, which has at least 65% identity to the nucleotide sequence of SEQ ID NO: 12, 14, 16 or 18.

Examples of the "condensation reaction catalytic domain or a subdomain thereof, which consists of an amino acid sequence having deletion, substitution, insertion and/or addition of at least one amino acid residue in the amino acid sequence of SEQ ID NO: 13, 15, 17 or 19, or a polyamino acid synthetase comprising the domain" include a condensation reaction catalytic domain or a subdomain thereof, which consists of an amino acid sequence having deletion, substitution, insertion and/or addition of, for example, 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6 (1 to several), 1 to 5, 1 to 4, 1 to 3, 1 to 2, or 1 amino acid residue in the amino acid sequence of SEQ ID NO: 13, 15, 17 or 19, and a polyamino acid synthetase comprising the domain. In general, the smaller the number of the above-described amino acid residues to be deleted, substituted, inserted and/or added, the more preferable it is.

Examples of the "condensation reaction catalytic domain or a subdomain thereof, which consists of an amino acid sequence having high identity to the amino acid sequence of SEQ ID NO: 13, 15, 17 or 19, or a polyamino acid synthetase comprising the domain" include a condensation reaction catalytic domain or a subdomain thereof, which consists of an amino acid sequence having at least about 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to the amino acid sequence of SEQ ID NO: 13, 15, 17 or 19, and a polyamino acid synthetase comprising the domain. In general, the larger the numerical value of the above-described identity, the more preferable it is. In the present specification, the term "identity" is distinguished from the term "homology". For example, when referring to the homology between amino acid sequences, amino acids having similar properties (e.g., glutamic acid and aspartic acid) are regarded as belonging to the same group, but when referring to the identity, such amino acids are distinguished from each other. That is, identity means consistency.

Examples of the "nucleotide sequence which can hybridize to the nucleotide sequence of SEQ ID NO: 12, 14, 16 or 18 under stringent hybridization conditions" include nucleotide sequences having at least about 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to the desired nucleotide sequence when performing calculation by a homology (or identity) search software such as FASTA and BLAST using default parameters.

3. Recombinant Vector, Transformant and Method for Producing Polyamino Acid Synthetase Using the Same of the Present Invention The present invention also relates to a recombinant vector comprising a polynucleotide encoding the polyamino acid synthetase of the present invention as an insert. Specifically, the present invention provides a recombinant vector comprising a nucleotide sequence encoding a polyamino acid synthetase consisting of any one of the following amino acid sequences: (i) the amino acid sequence of SEQ ID NO: 2; (ii) an amino acid sequence having deletion, substitution, insertion and/or addition of at least one amino acid residue in the amino acid sequence of SEQ ID NO: 2; and (iii) an amino acid sequence having at least 60% identity to the amino acid sequence of SEQ ID NO: 2.

The present invention also provides a recombinant vector comprising a polynucleotide consisting of any one of the following nucleotide sequences: (i) the nucleotide sequence of SEQ ID NO: 1; (ii) a nucleotide sequence encoding a polyamino acid synthetase, which can hybridize to a nucleotide sequence complementary to the nucleotide sequence of SEQ ID NO: 1 under stringent hybridization conditions; and (iii) a nucleotide sequence encoding a polyamino acid synthetase, which has at least 65% identity to the nucleotide sequence of SEQ ID NO: 1.

The present invention also relates to a recombinant vector comprising a polynucleotide encoding the condensation reaction catalytic domain of the present invention or a subdomain thereof or a polynucleotide encoding a polyamino acid synthetase comprising the condensation reaction catalytic domain or a subdomain thereof as an insert. Specifically, the present invention provides a recombinant vector comprising a nucleotide sequence encoding: a polynucleotide encoding a condensation reaction catalytic domain or a subdomain thereof, which consists of any one of the following amino acid sequences: (i) the amino acid sequence of SEQ ID NO: 13, 15, 17 or 19; (ii) an amino acid sequence having deletion, substitution, insertion and/or addition of at least one amino acid residue in the amino acid sequence of SEQ ID NO: 13, 15, 17 or 19; and (iii) an amino acid sequence having at least 60% identity to the amino acid sequence of SEQ ID NO: 13, 15, 17 or 19; or a polyamino acid synthetase comprising the condensation reaction catalytic domain or a subdomain thereof.

The present invention further provides a recombinant vector comprising a polynucleotide consisting of any one of the following nucleotide sequences: (i) the nucleotide sequence of SEQ ID NO: 12, 14, 16 or 18; (ii) a nucleotide sequence encoding a condensation reaction catalytic domain or a subdomain thereof, which can hybridize to a nucleotide sequence complementary to the nucleotide sequence of SEQ ID NO: 12, 14, 16 or 18 under stringent hybridization conditions; and (iii) a nucleotide sequence encoding a condensation reaction catalytic domain or a subdomain thereof, which has at least 65% identity to the nucleotide sequence of SEQ ID NO: 12, 14, 16 or 18.

In a preferred embodiment of the present invention, the recombinant vector is a recombinant expression vector in which an insert thereof can be expressed. Such a recombinant vector can be prepared using any method known in the art.

In the present invention, a vector to be used for expressing the polyamino acid synthetase of the present invention may be a vector which is suitable for the cell-free expression system (in vitro transcription-translation) or the protein expression system using a host cell such as E. coli, yeast, cultured animal cell or the like. Such a vector is commercially available or can be easily prepared from a publicly-known vector. Examples of vectors to be used for in vitro translation and expression in a cultured animal cell include: a pTargetT vector, in which an immediate-early enhancer/promoter region of human cytomegalovirus is incorporated, and which has, at a downstream region thereof, a T7 promoter sequence/multicloning site; a pSI vector having SV40 enhancer and an early promoter of SV40 (Promega); pBK-CMV, CMV-Script, pCMV-Tag and pBK-RSV (STRATAGENE); and the like. Examples of vectors suitable for expression in a microbial host such as $E.\ coli$ and yeast include: an expression vector system of the pET series having T7 promoter of $E.\ coli$ (e.g., pET3a, pET27b (+) and pET28a (+) (Novagen)); and $Pichia$ expression-based vectors of the pIC series having an alcohol oxidase promoter of yeast (e.g., pPIC9K and PIC3.5K (Invitorgen)).

A peptide sequence for purification may be a peptide sequence which is used in the art. Examples thereof include: a histidine tag sequence having at least 4, and preferably at least 6 contiguous histidine residues; an epitope tag sequence having the ability to bind to a monoclonal antibody; and a sequence encoding a glutathione binding domain or protein A of glutathione S-transtransferase. A vector containing a DNA encoding such a peptide sequence as an insert is commercially available. Examples of vectors to be used for a host of microorganisms such as $E.\ coli$ and yeast include: an expression vector having a T7 promoter of $E.\ coli$, and fusion expressing 10 histidine residues at its amino terminus (e.g., pET16b; Novagen); an expression vector having 6 histidine residues at the amino terminus (e.g., pHB6; Roche Diagnostics, pTrc-His series of vectors; Invitrogen, and pHAT series of vectors; Clontech); and the like. As a vector to be used for expression in a cultured animal cell, a vector which fusion expresses 6 histidine residues at its amino terminus (e.g., pHM6 and pVM6; Roche Diagnostics) can be used. In the case of cultured insect cells, a vector which fusion expresses 6 histidine residues of baculovirus at its amino terminus (e.g., pBacPAK-His vector; Clontech), pGEX series of vectors which fusion express glutathione S-transferase (Pharmacia), and pRIT2 or pEZZ 18 vector expressing protein A (Pharmacia) can be used.

In vitro translation for producing the polyamino acid synthetase of the present invention can be performed using publicly-known methods, for example, those described in: Spirin, A. S., et. al., Science 242: 1162-1164 (1988); and Patnaik, R. & Swartz, J. M. Biotechniques 24: 862-868 (1998), and a commercially-available in vitro translation kit (e.g., TNT-in vitro transcription/translation kit, Promega) may be used.

The present invention also relates to a transformant transformed with the above-described recombinant vector (e.g., host cell (e.g., microorganisms ($E.\ coli$, yeast, etc.)) and cultured animal cell (cultured insect cell, cultured mammalian cell (e.g., CHO cell and COS7 cell))).

The present invention also relates to a method for producing a polyamino acid synthetase using the recombinant vector of the present invention or the transformant of the present invention. The method for producing the polyamino acid synthetase of the present invention consists of, for example, performing in vitro transcription/translation using the recombinant expression vector of the present invention. Alternatively, the method consists of culturing a host cell transformed with the above-described recombinant expression vector and isolating a desired protein.

In the method for producing the polyamino acid synthetase of the present invention, after culturing a host cell, a protein expressed can be isolated from a culture medium or a soluble or insoluble fraction of bacterium.

In the method for producing the polyamino acid synthetase of the present invention, a protein expressed is isolated and purified using a publicly-known method, but a purification method may be suitably selected from publicly-known methods. For example, when the polyamino acid synthetase of the present invention includes a peptide sequence for the above-described purification, the purification is preferably performed using this. Specifically, nickel chelate affinity chromatography may be used for a histidine tag sequence, affinity chromatography with glutathione binding gel may be used for a binding domain of glutathione of S-transtransferase, and antibody affinity chromatography may be used for protein A or other protein sequences.

4. Polyamino Acid Production Method of the Present Invention

The present invention also relates to a method for producing the polyamino acid of the present invention. Specifically, the present invention provides a method for producing a polyamino acid, which comprises the step of synthesizing the polyamino acid using a polyamino acid synthetase comprising any one of the following amino acid sequences:
(i) the amino acid sequence of SEQ ID NO: 2;
(ii) an amino acid sequence having deletion, substitution, insertion and/or addition of at least one amino acid residue in the amino acid sequence of SEQ ID NO: 2; and
(iii) an amino acid sequence having at least 60% identity to the amino acid sequence of SEQ ID NO: 2

The present invention also provides a method for producing a polyamino acid, which comprises the step of synthesizing the polyamino acid using a polyamino acid synthetase comprising any one of the following amino acid sequences:
(i) the amino acid sequence of SEQ ID NO: 13, 15, 17 or 19;
(ii) an amino acid sequence having deletion, substitution, insertion and/or addition of at least one amino acid residue in the amino acid sequence of SEQ ID NO: 13, 15, 17 or 19; and
(iii) an amino acid sequence having at least 60% identity to the amino acid sequence of SEQ ID NO: 13, 15, 17 or 19.

The above-described polyamino acid is preferably polylysine, and more preferably ε-poly-L-lysine.

The polyamino acid production method of the present invention is carried out by reacting amino acid in the presence of the above-described polyamino acid synthetase. Here, a typical example of amino acid to be reacted is L-lysine, but the present invention is not limited thereto. For example, L-lysine ethyl ester, L-lysine methyl ester (in both the cases, ε-poly-L-lysine is produced), etc. may also be used for polyamino acid synthesis using the amino acid synthetase of the present invention. Moreover, there is a possibility that D-lysine, DL-5-hydroxy-lysine, Nε-methyl-L-lysine, L-lysine-hydroxamic acid, S-(2-aminoethyl)-L-cysteine, O-(2-aminoethyl)-L-serine, DL-trans-2,6-diamino-4-hexanoic acid, etc. may also be used in the polyamino acid production method of the present invention.

In the polyamino acid synthesis method of the present invention, the optimum pH for the polymerization reaction of amino acid using the above-described enzyme is preferably about 7 to 9.

The blending amount of the polyamino acid synthetase of the present invention is not particularly limited. In order to obtain a polymerized product by means of reaction of 1 g of raw material amino acid for several hours (2 to 5 hours), in general, the blending amount of the polyamino acid synthetase of the present invention is usually about at least 10,000 units, preferably about 20,000 to 40,000 units, and more preferably about 30,000 units. The temperature of the above-described reaction is not particularly limited as long as it allows the action of the enzyme. For example, the reaction proceeds at a low temperature (e.g., at about 15° C.), but on the premise that the enzyme acts efficiently and stably, usually, it is desired that the temperature is about 20 to 40° C. The reaction time can be suitably determined depending on the concentration of amino acid to be used, the addition amount of enzyme, etc., but usually, the reaction time is suitably set to about 0.5 to 5 hours, and within 24 hours at the most.

The polyamino acid thus obtained typically has a polymerization degree of 3 to 100 mer and an average molecular weight of 403 to 21835. The polymerization degree is preferably 4 to 50 mer, and more preferably 4 to 20 mer. The average molecular weight is preferably 531 to 6427, and more preferably 531 to 2581.

The polyamino acid obtained by the present invention can be used as an antimicrobial agent or the like, and can be used for various applications such as toiletry products, cosmetics, feed additives, medicines, agricultural chemicals, food additives, and electronic materials.

5. Primer, Probe and Screening Method Using the Same of the Present Invention

A partial fragment of the polynucleotide (DNA) of the present invention can be used for screening a homolog of the polyamino acid synthetase of the present invention or a polynucleotide encoding the same, for example, by utilizing the fragment as a probe or PCR primer.

Therefore, the present invention also provides a primer consisting of a polynucleotide comprising at least 15 contiguous nucleotides in any one of the following nucleotide sequences or complementary sequences thereof:
(i) a nucleotide sequence encoding a polyamino acid synthetase consisting of the amino acid sequence of SEQ ID NO: 2 or a complementary sequence thereof;
(ii) a nucleotide sequence encoding a polyamino acid synthetase consisting of an amino acid sequence having deletion, substitution, insertion and/or addition of at least one amino acid residue in the amino acid sequence of SEQ ID NO: 2 or a complementary sequence thereof;
(iii) a nucleotide sequence encoding a polyamino acid synthetase consisting of an amino acid sequence having at least 60% identity to the amino acid sequence of SEQ ID NO: 2 or a complementary sequence thereof;
(iv) the nucleotide sequence of SEQ ID NO: 1 or a complementary sequence thereof;
(v) a nucleotide sequence encoding a polyamino acid synthetase, which can hybridize to a nucleotide sequence complementary to the nucleotide sequence of SEQ ID NO: 1 under stringent hybridization conditions, or a complementary sequence thereof; and
(vi) a nucleotide sequence encoding a polyamino acid synthetase, which has at least 65% identity to the nucleotide sequence of SEQ ID NO: 1, or a complementary sequence thereof.

The present invention also provides a primer consisting of a polynucleotide comprising at least 15 contiguous nucleotides in any one of the following nucleotide sequences or complementary sequences thereof:
(i) a nucleotide sequence encoding a condensation reaction catalytic domain or a subdomain thereof, which consists of the amino acid sequence of SEQ ID NO: 13, 15, 17 or 19, or a complementary sequence thereof;
(ii) a nucleotide sequence encoding a condensation reaction catalytic domain or a subdomain thereof, which consists of an amino acid sequence having deletion, substitution, insertion and/or addition of at least one amino acid residue in the amino acid sequence of SEQ ID NO: 13, 15, 17 or 19, or a complementary sequence thereof;
(iii) a nucleotide sequence encoding a condensation reaction catalytic domain or a subdomain thereof, which consists of an amino acid sequence having at least 60% identity to the amino acid sequence of SEQ ID NO: 13, 15, 17 or 19, or a complementary sequence thereof;
(iv) the nucleotide sequence of SEQ ID NO: 12, 14, 16 or 18 or a complementary sequence thereof;
(v) a nucleotide sequence encoding a condensation reaction catalytic domain or a subdomain thereof, which can hybridize to a nucleotide sequence complementary to the nucleotide sequence of SEQ ID NO: 12, 14, 16 or 18 under stringent hybridization conditions, or a complementary sequence thereof; and
(vi) a nucleotide sequence encoding a condensation reaction catalytic domain or a subdomain thereof, which has at least 65% identity to the nucleotide sequence of SEQ ID NO: 12, 14, 16 or 18, or a complementary sequence thereof.

The present invention also provides a polynucleotide probe consisting of a nucleotide sequence of at least 15 nucleotides, which can hybridize, under stringent hybridization conditions, to any one of the following nucleotide sequences:
(i) a nucleotide sequence encoding a polyamino acid synthetase consisting of the amino acid sequence of SEQ ID NO: 2 or a complementary sequence thereof;
(ii) a nucleotide sequence encoding a polyamino acid synthetase consisting of an amino acid sequence having deletion, substitution, insertion and/or addition of at least one amino acid residue in the amino acid sequence of SEQ ID NO: 2 or a complementary sequence thereof;
(iii) a nucleotide sequence encoding a polyamino acid synthetase consisting of an amino acid sequence having at least 60% identity to the amino acid sequence of SEQ ID NO: 2 or a complementary sequence thereof;
(iv) the nucleotide sequence of SEQ ID NO: 1 or a complementary sequence thereof;
(v) a nucleotide sequence encoding a polyamino acid synthetase, which can hybridize to a nucleotide sequence complementary to the nucleotide sequence of SEQ ID NO: 1 under stringent hybridization conditions, or a complementary sequence thereof; and
(vi) a nucleotide sequence encoding a polyamino acid synthetase, which has at least 65% identity to the nucleotide sequence of SEQ ID NO: 1, or a complementary sequence thereof.

The present invention also provides a polynucleotide probe consisting of a nucleotide sequence of at least 15 nucleotides, which can hybridize, under stringent hybridization conditions, to any one of the following nucleotide sequences:
(i) a nucleotide sequence encoding a condensation reaction catalytic domain or a subdomain thereof, which consists of the amino acid sequence of SEQ ID NO: 13, 15, 17 or 19, or a complementary sequence thereof;
(ii) a nucleotide sequence encoding a condensation reaction catalytic domain or a subdomain thereof, which consists of an amino acid sequence having deletion, substitution, insertion and/or addition of at least one amino acid residue in the amino acid sequence of SEQ ID NO: 13, 15, 17 or 19, or a complementary sequence thereof;
(iii) a nucleotide sequence encoding a condensation reaction catalytic domain or a subdomain thereof, which consists of an amino acid sequence having at least 60% identity to the amino acid sequence of SEQ ID NO: 13, 15, 17 or 19, or a complementary sequence thereof;
(iv) the nucleotide sequence of SEQ ID NO: 12, 14, 16 or 18 or a complementary sequence thereof;
(v) a nucleotide sequence encoding a condensation reaction catalytic domain or a subdomain thereof, which can hybridize to a nucleotide sequence complementary to the nucleotide sequence of SEQ ID NO: 12, 14, 16 or 18 under stringent hybridization conditions, or a complementary sequence thereof; and (vi) a nucleotide sequence encoding a condensation reaction catalytic domain or a subdomain thereof, which has at least 65% identity to the nucleotide sequence of SEQ ID NO: 12, 14, 16 or 18, or a complementary sequence thereof.

The present invention also provides a method for screening a polynucleotide encoding a polyamino acid synthetase using the above-described primer. Preferably, in the screening method, the above-described probe is further used.

Specifically, the primer or probe of the present invention can be used, for example, for analysis of the presence of a homolog of the polyamino acid synthetase of the present invention in an analyte by means of Northern hybridization or semiquantitative reverse PCR (Sourvinos, G et al., Oncogene, 18, 4968, (1999)) using the above-described primer and/or probe, or for detection of the presence/absence of mutation of a gene encoding the polyamino acid synthetase of the present invention in an analyte or the position of mutation by means of the PCR-SSCP method (Proc. Natl. Acad. Sci. USA., 86, 2766, (1989)) or the like.

The length of the primer or probe is not particularly limited as long as it is enough for the above-described analysis or detection. However, usually, the nucleotide length of the primer is preferably about 10 to 100, more preferably about 15 to 80, even more preferably about 20 to 60, and most preferably about 20 to 40. The nucleotide length of the probe is, for example, about 10 to 1000, about 15 to 1500, preferably about 20 to 1000, more preferably about 30 to 800, even more preferably about 50 to 700, still more preferably about 100 to 500, and most preferably about 200 to 500.

An amplification method using the primer of the present invention may be polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), a transcription-based amplification system (TAS; Kwoh et al., 1989), strand displacement amplification (SDA; Duck, 1990; Walker et al., 1992), amplification using QB replicase (Lizardi et al., 1988; Lomeli et al., 1989), or any of other appropriate methods for amplifying a nucleic acid molecule using primer extension. During amplification, an amplified product can be conveniently labeled using a labeled primer or by taking a labeled nucleotide. Labeling may be performed using any of isotopes (e.g., $^{32}P$ and $^{35}S$) and nonisotopes (e.g., biotin and digoxigenin). Amplification reaction is repeated 20 to 70 times, and preferably 25 to 45 times.

6. Antibody of the Present Invention

The present invention also relates to an antibody, which is prepared using the polyamino acid synthetase of the present invention or a fragment thereof as an antigen, and which specifically binds to the antigen, e.g., a polyclonal antibody or a monoclonal antibody. Specifically, the present invention provides:

an antibody which specifically binds to a polyamino acid synthetase comprising any one of the following amino acid sequences:
(i) the amino acid sequence of SEQ ID NO: 2;
(ii) an amino acid sequence having deletion, substitution, insertion and/or addition of at least one amino acid residue in the amino acid sequence of SEQ ID NO: 2; and
(iii) an amino acid sequence having at least 60% identity to the amino acid sequence of SEQ ID NO: 2.

The present invention also provides an antibody which specifically binds to: a condensation reaction catalytic domain or a subdomain thereof which comprises any one of the following amino acid sequences:
(i) the amino acid sequence of SEQ ID NO: 13, 15, 17 or 19;
(ii) an amino acid sequence having deletion, substitution, insertion and/or addition of at least one amino acid residue in the amino acid sequence of SEQ ID NO: 13, 15, 17 or 19; and
(iii) an amino acid sequence having at least 60% identity to the amino acid sequence of SEQ ID NO: 13, 15, 17 or 19; or a polyamino acid synthetase comprising the domain.

The antibody which specifically binds to the polyamino acid synthetase of the present invention can be produced using the polyamino acid synthetase of the present invention as an antigen according to an antibody (or antiserum) production method known in the art. As an antigen, an extracted natural protein, a recombinant protein, a partial decomposition product of these proteins, or a synthetic peptide based on the amino acid sequence of the polyamino acid synthetase of the present invention can be used. Such an antigen is, for example, a polypeptide consisting of an amino acid sequence of at least 5 contiguous amino acids, and preferably 10 to 15 amino acid residues in the amino acid sequence of SEQ ID NO: 2. The antibody of the present invention can be prepared according to the ordinary method (e.g., Harlow, E. & Lane, D, in Antibodies-Laboratory manual Cold Spring Harbor LaboratoryPress., pp. 53-138 (1988)).

The antibody of the present invention can be used for detection and search of the polyamino acid synthetase of the present invention and other polyamino acid synthetases having sequence homology to the protein. According to the screening method of the present invention, a similar polyamino acid synthetase in terms of the classification can be easily obtained.

The above-described screening method consists of, for example, detecting and searching a protein to which the antibody of the present invention binds using a rough extract from another living organism or tissue thereof containing another polyamino acid synthetase as a sample. Examples of such means for detection include immunoblotting and immunoaffinity chromatography. Further, with respect to a DNA library of another living organism or tissue thereof containing another polyamino acid synthetase, expression cloning (Sambrook, J., Fritsch, E. F., & Maniatis, T., Molecular Cloning—a Laboratory Mannual, second edition. Cold Spring Harbor Laboratory Press. pp. 12.3-12.44 (1989)) is carried out using the antibody of the present invention, thereby directly obtaining a DNA encoding a novel polyamino acid synthetase.

Hereinafter, the present invention will be specifically described by way of illustrative examples, but the present invention is not limited thereto.

EXAMPLES

Example 1

Purification of ε-Poly-L-Lysine Biosynthetic Enzyme from *Streptomyces Albulus* Strain IFO14147 which Produces ε-Poly-L-Lysine and Examination of Enzymatic Properties Thereof (1) Culture of *Streptomyces albulus* Strain IFO14147, which is a ε-Poly-L-Lysine Producing Strain Culture of the strain was performed in a M3G medium (5% glucose, 0.5% yeast extract, 1% ammonium sulfate, 0.08% K2HPO4, 0.136% KH2PO4, 0.05% MgSO4.7H2O, 0.004% ZnSO4.7H2O, 0.003% FeSO4.7H2O (pH 6.8)). 100 ml of preculture solution obtained by aerobically culturing at 30°

C. for 20 hours was added to 2 L of medium, and using a 3 L jar fermenter (Marubishi Bioengineering), culturing was carried out aerobically at 30° C. at 500 rpm with the ventilation volume of 2.5 L/min. As the bacterium grew, pH of the culture solution gradually decreased. Therefore, from the time point at which pH reached 4.2 that is most suitable for ε-poly-L-lysine production, 10% aqueous ammonia was added to the culture solution, thereby maintaining pH of 4.2. After culture for 32 hours, the bacterium was collected from the culture solution by centrifugation. The yield was about 240 g wet weight.

(2) Purification of ε-Poly-L-Lysine Biosynthetic Enzyme from *Streptomyces albulus* Strain IFO14147 which Produces ε-Poly-L-Lysine All the steps for purification were carried out at 4° C. or on the ice. 75 g wet weight of bacterium was suspended in buffer solution A (pH 8.0) consisting of 150 ml of 100 mM tris (hydroxymethyl)aminomethane, 20% (w/v) glycerol, 0.2 M NaCl, 2 mM EDTA and 5 mM DTT, and the bacterium was disintegrated by means of sonication. The treated solution was subjected to centrifugation at 10,000 g for 20 minutes to remove residues, thereby preparing a crude enzyme solution. This was subjected to ultracentrifugation (Beckman Coulter) at 160,000 g for 1 hour, and precipitate was collected as cell membrane fraction. The obtained cell membrane fraction was suspended in buffer solution B (pH 8.0) consisting of 30 ml of 100 mM tris(hydroxymethyl)aminomethane, 20 (w/v) % glycerol, 1.0 M NaCl and 5 mM DTT, and this was subjected to sonication. After that, collection was carried out by ultracentrifugation in the same way to obtain salt-washed cell membrane fraction. The salt-washed cell membrane fraction was suspended in buffer solution C (pH 8.6) consisting of 30 ml of 100 mM tris(hydroxymethyl)aminomethane, 30% (w/v) glycerol, 1% (w/v) NP-40 (IGEPAL CA-630, MP-Biomedicals) and 5 mM DTT, and sonication and ultracentrifugation were carried out in the same way. The obtained supernatant was NP-40 solubilized cell membrane fraction containing ε-poly-L-lysine biosynthetic enzyme.

The NP-40 solubilized cell membrane fraction was adsorbed to a DEAE TOYOPEARL 650M column (2.5×10 cm, Tosoh) equilibrated with buffer solution D (pH 8.6) consisting of 50 mM tris(hydroxymethyl)aminomethane, 30% (w/v) glycerol, 0.4% (w/v) NP-40 and 2 mM DTT. After the column was washed with the same buffer solution, the enzyme was eluted by NaCl concentration gradient method (0 to 0.3 M). The active fraction was collected, and after pH was adjusted to 8.2 using 0.1 M acetic acid solution, it was adsorbed to an AF-Blue TOYOPEARL 650M column (1.5× 6.5 cm, Tosoh) equilibrated with buffer solution D (pH 8.2). After the column was washed with the same buffer solution, the enzyme was eluted by NaCl concentration gradient method (0 to 2 M). The active fraction was collected, and after concentrated by means of ultrafiltration (YM-50, Amicon), it was added to a Sephacryl S-300 HR column (1.5×45 cm, Amersham Biosciences) equilibrated with buffer solution D (pH 8.2) containing 0.2 M NaCl and eluted with the same buffer solution at a flow rate of 0.15 ml/min. By carrying out the above-described operations, 2.9 mg of the purified ε-poly-L-lysine biosynthetic enzyme was successfully prepared. This purified enzyme preparation was homogeneous when subjected to SDS-polyacrylamide electrophoresis. The yield in the purification of ε-poly-L-lysine biosynthetic enzyme is shown in Table 1 below.

TABLE 1

| Step | Total amount (ml) | Total activity (U) | Total protein (mg) | Specific activity (U/mg) | Collection rate (%) | Purification degree (-fold) |
|---|---|---|---|---|---|---|
| Crude enzyme solution | 180 | 105000 | 2580 | 40.8 | 100 | 1.0 |
| Cell membrane fraction | 36 | 74700 | 349 | 214 | 71 | 5.2 |
| Salt-washed membrane fraction | 34 | 73200 | 212 | 345 | 70 | 8.4 |
| NP-40 solubilized fraction | 31 | 67300 | 104 | 647 | 64 | 16 |
| DEAE-TOYOPEARL | 30 | 64000 | 25.2 | 2540 | 61 | 62 |
| Blue-TOYOPEARL | 28 | 27200 | 4.3 | 6400 | 26 | 156 |
| Sephacryl S-300 | 12 | 19600 | 2.9 | 6880 | 19 | 168 |

Results of SDS-PAGE analysis of respective fractions in the purification process of ε-poly-L-lysine biosynthetic enzyme are shown in FIG. 4.

(3) Examination of Enzymatic Properties of ε-Poly-L-Lysine Biosynthetic Enzyme

Examination of enzymatic properties was carried out using the purified enzyme preparation.

The measurement of the ε-poly-L-lysine biosynthesis activity was performed according to the method of Kawai et al. (Biochem Biophys Res Commun. 2003 Nov. 21; 311 (3): 635-40) with some modification. A reaction solution (40 μl), which includes: 1 mM L-lysine containing 92.5 kBq/ml L-[U-14C]lysine (Amersham Biosciences); 5 mM $MgCl_2$; 5 mM ATP; 1 mM DTT; 20% (w/v) glycerol; 0.2% (w/v) NP-40; 100 mM TAPS-NaOH buffer solution (pH 8.5); and the enzyme, was incubated at 30° C. 10 μl of the reaction solution was spotted on a glass fiber filter paper having the diameter of 2.1 cm (Whatman), and it was immediately immersed in an ice-cold sodium solution of 5% (w/v) trichloroacetic acid-0.25% (w/v) tungstic acid. It was allowed to stand for 20 minutes and thereafter mildly shaken for 5 minutes. After the filter was shaken again in the same solution for 5 minutes, it was rinsed with ethanol and then dried. The amount of radioactivity bound to the filter was measured using a liquid scintillation counter (Aloka). The amount of enzyme by which 1 pmol/second of L-lysine is taken into ε-poly-L-lysine under the above-described reaction conditions was defined as 1 unit. Specific activity of a protein is represented by unit per 1 mg of the protein. Quantitation of protein was performed using the Bradford method. A calibration curve was made using bovine serum albumin (Wako Pure Chemical Industries, Ltd.).

The adenylation activity of L-lysine and other amino acids was measured by ATP-PPi exchange reaction. A reaction solution (40 μl), which includes: 1 mM L-lysine or another amino acid; 5 mM MgCl$_2$; 5 mM. ATP; 1 mM DTT; 20% (w/v) glycerol; 0.2% (w/v) NP-40; 0.2 mM sodium diphosphate; 51.8 kBq/ml [32P] sodium diphosphate; 100 mM TAPS-NaOH buffer solution (pH 8.5); and the enzyme, was incubated at 30° C. 1.0 ml of a solution containing 1.2% (w/v) active carbon, 0.1 M sodium diphosphate and 0.35 M perchloric acid was added thereto to terminate the reaction. After the active carbon was washed with pure water, the amount of radioactivity bound to the active carbon was measured using a liquid scintillation counter (Aloka).

Figure 5:
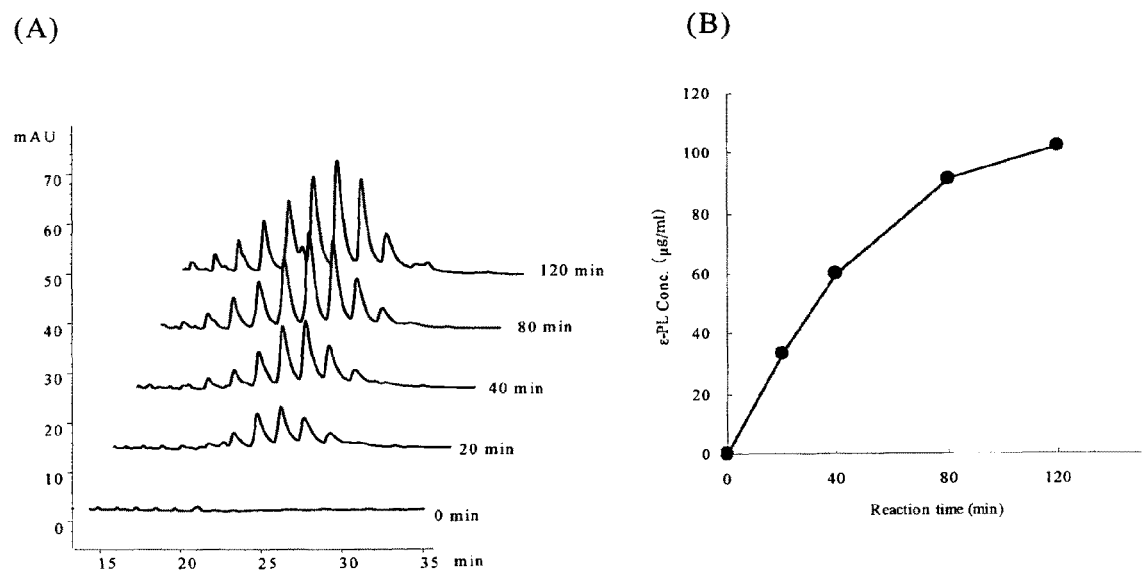
FIG. 5A is a graph showing the results of HPLC analysis of ε-poly-L-lysine in enzymatic reaction solution.
FIG. 5B is a graph showing the concentration of ε-poly-L-lysine in reaction solution obtained by making a calibration curve using the ε-poly-L-lysine standard product and making calculation based on the results in FIG. 5A.

Analysis of the polymerization degree and quantitation of the enzymatically-synthesized ε-poly-L-lysine were carried out by HPLC under the following conditions. A calibration curve was made using ε-poly-L-lysine manufactured by Chisso corporation.
Column: ODS-80Ts (4.6×250 mm, Tosoh)
Solvent A: 10 mM sodium dihydrogen phosphate, 10 mM sodium octane sulfonate, 100 mM sodium perchlorate
Solvent B: Solvent A+60% acetonitrile
Gradient: 42% Solvent B (0 min)→65% Solvent B (45 min)
Flow rate: 0.8 ml/min
Detection: 210 nm Analysis of ATP degradation product which is produced in ε-poly-L-lysine biosynthetic reaction was carried out by HPLC under the following conditions.
Column: ODS-80Ts (4.6×250 mm, Tosoh)
Solvent A: 20 mM sodium dihydrogen phosphate, 5 mM tetrabutylammonium bromide
Solvent B: Solvent A+60% methanol
Gradient: 35% Solvent B (0 min)→100% Solvent B (30 min)
Flow rate: 0.7 ml/min
Detection: 260 nm Analysis of LC-ESI-MS/MS of enzymatically-synthesized ε-poly-L-lysine was carried out under the following conditions.
HPLC apparatus: Agilent 1200 (Agilent)
Column: Develosil Praqueous-AR-5 (2.0×150 mm, Nomura Chemical Co., Ltd.)
Solvent A: 0.1% Heptafluorobutyric acid
Solvent B: 0.1% Heptafluorobutyric acid+acetonitrile
Gradient: 10% Solvent B (0 to 5 min)→45% Solvent B (45 min)
Flow rate: 0.4 ml/min
Detection: 210 nm
Mass Spectroscope: Esquire 4000 (Bruker)
Ionization mode: positive mode Confirmation of binding mode of enzymatically-synthesized ε-poly-L-lysine was carried out using the following method. ε-poly-L-lysine was purified from 15 ml of enzymatic reaction solution (25° C., 16 h) by HPLC under the following conditions (about 0.8 mg), and it was freeze-dried.
Column: ODS-80Ts (4.6×250 mm, Tosoh)
Solvent A: 0.1% trifluoroacetic acid
Solvent B: 0.1% trifluoroacetic acid+acetonitrile
Gradient: 0% Solvent B (0 to 10 min)→30% Solvent B (30 min)
Flow rate: 0.7 ml/min
Detection: 210 nm This was dinitrophenylated (DNP-lated) according to the method of Shima et al. (Agric. Biol. Chem. 1981 45:2503-2508). DNP-fated ε-poly-L-lysine was hydrolyzed in 6N HCl at 100° C. for 20 hours, and it was analyzed by thin-layer chromatography under the following conditions.
Thin-layer plate: Silica gel 60TLC plate (Merck)
Developing solvent: butanol, acetic acid, pyridine, water (4:1:1:2)
Coloring: ninhydrin Firstly, an enzymatic reaction (0.5 ml) was performed using 22 μg of purified enzyme preparation, and the obtained product was analyzed by ESI-LC-MS/MS. ε-poly-L-lysine obtained by fermentation showed a polymerization degree distribution which was 30 mer-centered, whereas the enzymatically-synthesized ε-poly-L-lysine showed a polymerization degree distribution which was 14 or 15 mer-centered. However, any of the retention time in LC, MS spectrum and MS/MS fragmentation pattern thereof corresponded to those of a partial hydrolysate of the ε-poly-L-lysine standard product (FIGS. 5 and 6). Further, in the analysis by thin-layer chromatography, by hydrolyzing the DNP-lated enzymatically-synthesized ε-poly-L-lysine with hydrochloric acid, Nα-2,4-DNP-L-lysine was generated as in the case of the ε-poly-L-lysine standard product. Therefore, it was indicated that the enzymatic reaction product was an isopeptide to which ε-amino group and α-carboxyl group of L-lysine were bound, i.e., ε-poly-L-lysine (FIG. 7), and it was confirmed that this enzyme was a ε-poly-L-lysine biosynthetic enzyme. ε-poly-L-lysine has the following structure:

[Chemical formula 1]

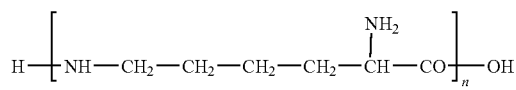

Next, the enzymatic reaction product was analyzed by HPLC, and reaction time-dependent increase of ε-poly-L-lysine was confirmed, but the polymerization degree of ε-poly-L-lysine produced was not dependent on reaction time and showed constant distribution. Further, ATP was converted into AMP as the reaction proceeded, and L-lysine adenylation activity was also confirmed. In view of the above-described matters, it is strongly suggested that in the case of this enzyme, L-lysine is polymerized in a manner same as thiotemplate type non-ribosomal peptide synthetase (NRPS), while in the case of biosynthetic enzyme of γ-polyglutamic acid (Appl Environ Microbiol. 2004 July; 70 (7): 4249-55) or cyanophycin (Appl Environ Microbiol. 2001 May; 67 (5): 2176-82), substrate amino acids are polymerized in a manner same as ligase.

Figure 8:
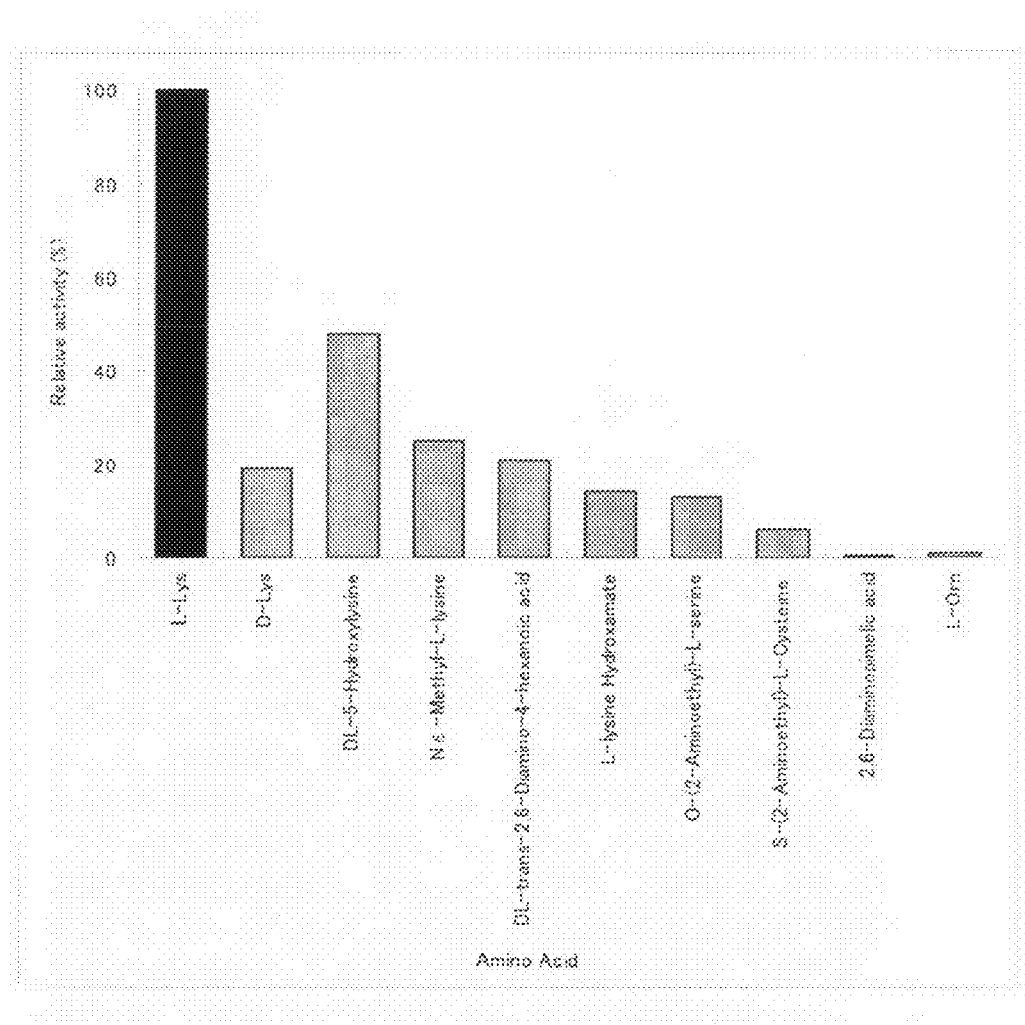
FIG. 8 is a graph showing substrate specificity of the amino acid synthetase of the present invention in an amino acid activation (adenylation) reaction. Relative activity is shown with the activity to L-lysine being regarded as 100%. None of L-Ala, L-Val, L-Leu, L-Ile, L-Phe, L-Pro, L-Trp, L-Met, Gly, L-Ser, L-Thr, L-Cys, L-Gln, L-Asn, L-Tyr, L-Arg, L-His, L-Asp and L-Glu was adenylated.

Moreover, when examining the enzymatic properties of the enzyme in detail, it was revealed that the enzyme has the following properties.
1) Optimum pH of synthesis reaction: pH 8.5
2) Optimum temperature of synthesis reaction: 25 to 30° C.
3) Temperature stability: half life of activity at 30° C., 35° C. and 40° C. were 180 minutes, 80 minutes and 19 minutes, respectively (buffer solution D containing 0.2 M NaCl (pH 8.2))
4) Metal ion requirement: for exhibition of the activity, addition of divalent cation is essential. The maximal activity is shown by addition of 5 mM Mg$^{2+}$ and 5 mM Mn$^{2+}$. Also activated slightly by addition of Ca$^{2+}$.
5) Substrate specificity: other than L-lysine, analogs of L-lysine such as D-lysine and DL-5-hydroxylysine shown in FIG. 8 were adenylated.
6) Nucleotide specificity: ATP-specific. In the case of GTP, UTP and CTP, substrate amino acids are not activated.

7) Molecular weight of subunit: it is calculated as about 130 kDa based on SDS-polyacrylamide electrophoresis under reducing conditions (FIG. 4).

8) Molecular weight: it is calculated as about 270 kDa based on gel filtration chromatography (Sephacryl S-300 HR, Amersham Biosciences).

According to the results in 7) and 8) above, it was inferred that the enzyme is a homodimer.

Example 2

Cloning of ε-Poly-L-Lysine Biosynthetic Enzyme Gene (1) Analysis of Amino Acid Sequence of ε-Poly-L-Lysine Biosynthetic Enzyme The amino acid sequence was analyzed by LC-MS/MS. ε-poly-L-lysine biosynthetic enzyme was fractionated by means of SDS-polyacrylamide electrophoresis, and after stained with CBB-R250, the band of ε-poly-L-lysine biosynthetic enzyme was cut out. To the sample gel piece, Tris buffer solution containing trypsin (pH 8.0) was added to perform in gel digestion at 35° C. for 20 hours. Trypsin-digested peptide solution extracted from the gel piece was subjected to LC-MS/MS analysis. LC-MS/MS analysis was carried out under the following conditions.

HPLC apparatus: MAGIC 2002 nano LC system (Michrom Bioresources)
Column: Magic C18 column (0.1×50 mm, Michrom Bioresources)
Solvent A: 0.1% formic acid+2% acetonitrile
Solvent B: 0.1% formic acid+90% acetonitrile
Gradient: 10% Solvent B (0 to 1 min)→50% Solvent B (21 min)
Flow rate: 250 to 300 nl/min
Mass Spectroscope: Q-T of 2 (Waters Micromass)
Ionization mode: positive mode The obtained MS/MS data was subjected to de novo sequence analysis using MassLynx software (Waters Micromass), and as a result, the amino acid sequences of 3 peptides, i.e., MAGAAWPAPAWQRSR (SEQ ID NO: 3), (I/L)E(I/L)GE(I/L)DAA(I/L)AA(I/L)PGVR (SEQ ID NO: 4) and A(I/L)AGT(I/L)KPGAYPR (SEQ ID NO: 5) were obtained.

(2) Acquisition of ε-Poly-L-Lysine Biosynthetic Enzyme Gene

*Streptomyces albulus* strain IFO14147 was inoculated in 100 ml of medium consisting of 103 g/L of sucrose, 10 g/L of tryptone, 5 g/L of yeast extract and 5 g/L of NaCl, and it was subjected to shaking culture at 30° C. for 24 hours. The bacterium was collected from this culture solution by centrifugation, and chromosomal DNA was prepared according to the ordinary method. Further, based on the determined internal amino acid sequences of the ε-poly-L-lysine biosynthetic enzyme (peptide 1: N-A(I/L)AGT(I/L)KPGAYPR-C (SEQ ID NO: 6); peptide 2; N-MAGAAWPAPAWQRSR-C (SEQ ID NO: 7)), the following 4 types of primers were designed.

(SEQ ID NO: 8)
pr-pp1F; 5'-AC(C/G)(A/C)T(C/G)AAGCC(C/G)GG(C/G)GC(C/G)TACCC-3'

(SEQ ID NO: 9)
pr-pp2R; 5'-CTGCCA(G/C)GC(G/C)GG(G/C)GC(G/C)GGCCA(G/C)GC-3'

(SEQ ID NO: 10)
pr-pp2F; 5'-GC(C/G)TGGCC(C/G)GC(C/G)CC(C/G)GC(C/G)TGGCA-3'

(SEQ ID NO: 11)
pr-pp1R; 5'-GGGTA(G/C)GC(G/C)CC(G/C)GGCTT(G/C)A(T/G)(G/C)GT-3'

When PCR was performed using these primers and chromosomal DNA as templates, in the case of the combination of pr-pp1F/pr-pp2R, a specific amplified fragment of about 500 bp was obtained. This amplified fragment was cloned into a plasmid pGEMT-easy, and the cloned fragment was labeled using an ECL labeling kit (GE Healthcare Bio-Sciences). The labeled gene fragment was used as a probe to perform screening of the cosmid library prepared from the chromosomal DNA of the bacterium (Supercos I, STRATAGENE), thereby further obtaining a 6.0 kb KpnI fragment to which the probe hybridizes. This fragment was subcloned into a plasmid pTSR193 (Reference: Actinomycetologica (2006) Vol. 20, p. 35-41), thereby determining the nucleotide sequence.

Example 3

Enzymatic Production of ε-Poly-L-Lysine

A reaction solution (200 μl) containing 2 mM 5 mM MgCl$_2$, 5 mM ATP, 1 mM DTT, 20% glycerol, 0.2% (w/v) NP-40, 100 mM TAPS-NaOH buffer solution (pH 8.5) and about 10 μg of the purified enzyme preparation was put into a 1.5 ml microtube, and it was incubated at 25° C. for 120 minutes. ε-poly-L-lysine produced in a manner similar to that in Example 1 was quantitated 20, 40, 80 and 120 minutes after the initiation of the reaction. The results are shown in Table 2.

TABLE 2

| Production of ε-poly-L-lysine by enzymatic reaction | |
|---|---|
| Reaction time (min) | Concentration of ε-poly-L-lysine (μg/ml) |
| 20 | 33.1 |
| 40 | 59.7 |
| 80 | 90.8 |
| 120 | 102.1 |

Example 4

Enzymatic Production of Heteropolyamino Acid Constituted by Lysine Analog and L-Lysine A reaction solution (200 μl) containing 2 mM substrate amino acid (L-lysine and analog were mixed in a given ratio), 5 mM MgCl$_2$, 5 mM ATP, 1 mM DTT, 20% glycerol, 0.2% (w/v) NP-40, 100 mM TAPS-NaOH buffer solution (pH 8.5) and about 10 μg of the purified enzyme preparation was put into a 1.5 ml microtube, and it was incubated at 25° C. 4 hours later, polyamino acid produced in a manner similar to that in Example 1 was subjected to ESI-LC-MS analysis.

Figure 9:
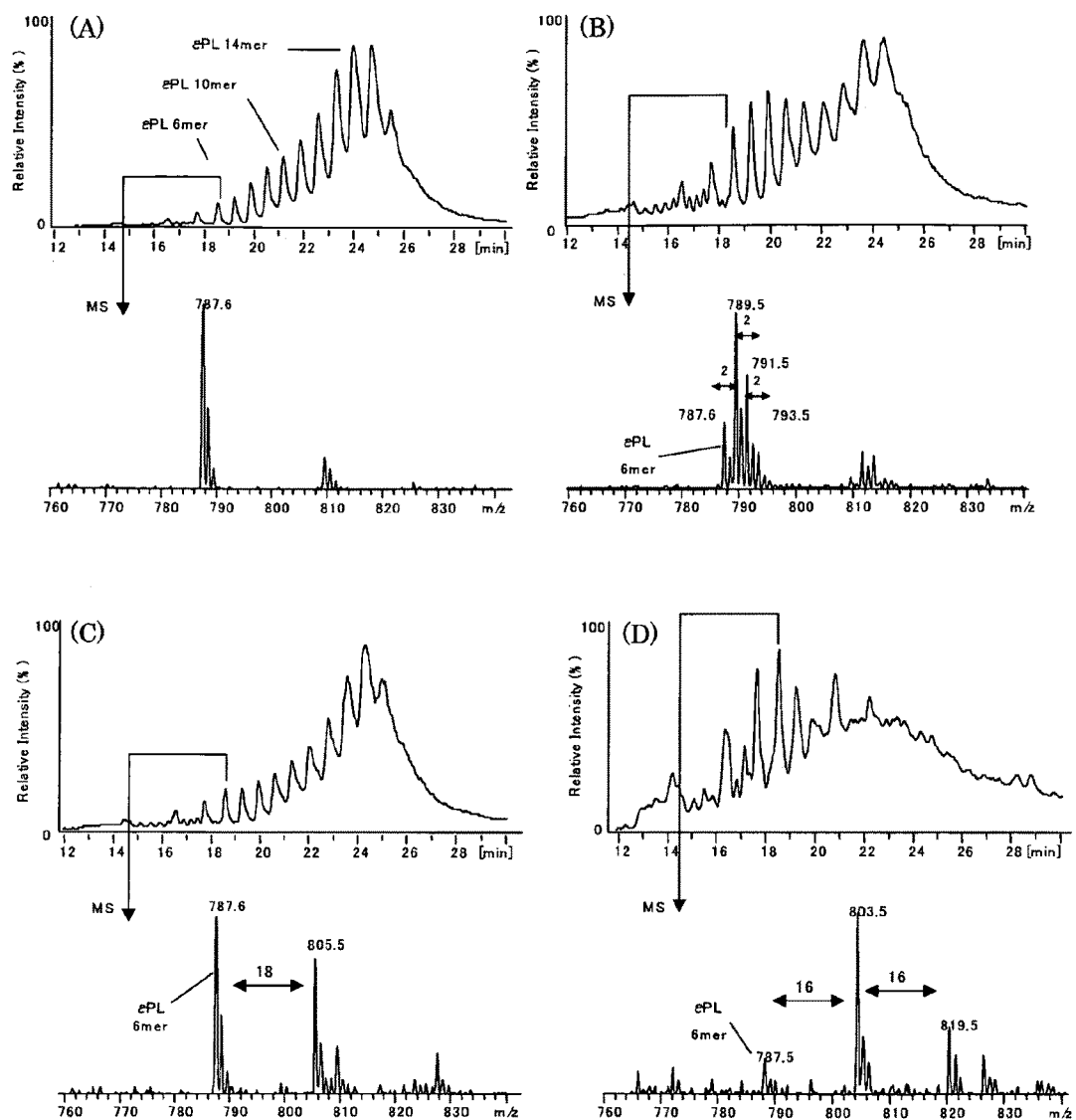
FIG. 9 shows the results of ESI-LC-MS analysis of polyamino acids produced by an enzymatic reaction using a mixture of L-lysine and analog as a substrate. (A) is a graph showing the fraction pattern in LC and the result of mass analysis of a polyamino acid obtained by a reaction using only L-lysine as a substrate (ε-poly-L-lysine). (B) is a graph showing the fraction pattern in LC and the result of mass analysis of a polyamino acid obtained by a reaction using a mixture of 1.8 mM O-(2-aminoethyl)-L-serine and 0.2 mM L-lysine as a substrate. (C) is a graph showing the fraction pattern in LC and the result of mass analysis of a polyamino acid obtained by a reaction using a mixture of 1.8 mM S-(2-aminoethyl)-L-cysteine and 0.2 mM L-lysine as a substrate. (D) is a graph showing the fraction pattern in LC and the result of mass analysis of a polyamino acid obtained by a reaction using a mixture of 1.6 mM DL-5-hydroxylysine and 0.4 mM L-lysine as a substrate.

The results are shown in FIG. 9. When adding an analog which is adenylated by the enzyme such as DL-5-hydroxylysine (FIG. 9D), S-(2-aminoethyl)-L-cysteine (FIG. 9C) and O-(2-aminoethyl)-L-serine (FIG. 9B) as a substrate, heteropolyamino acid in which the analog was taken into the polylysine molecule was obtained at a constant frequency.

Example 5

Microbial Production of Heteropolyamino Acid Constituted by Lysine Analog and L-Lysine Heteropolyamino acid in which an analog is taken into a ε-poly-L-lysine molecule can be enzymatically synthesized by the procedure of Example 4. However, in the case of heteropolyamino acid containing S-(2-aminoethyl)-L-cysteine, it can be more conveniently produced using *Streptomyces albulus* per se, which is a ε-poly-L-lysine producing bacterium.

Figure 10:
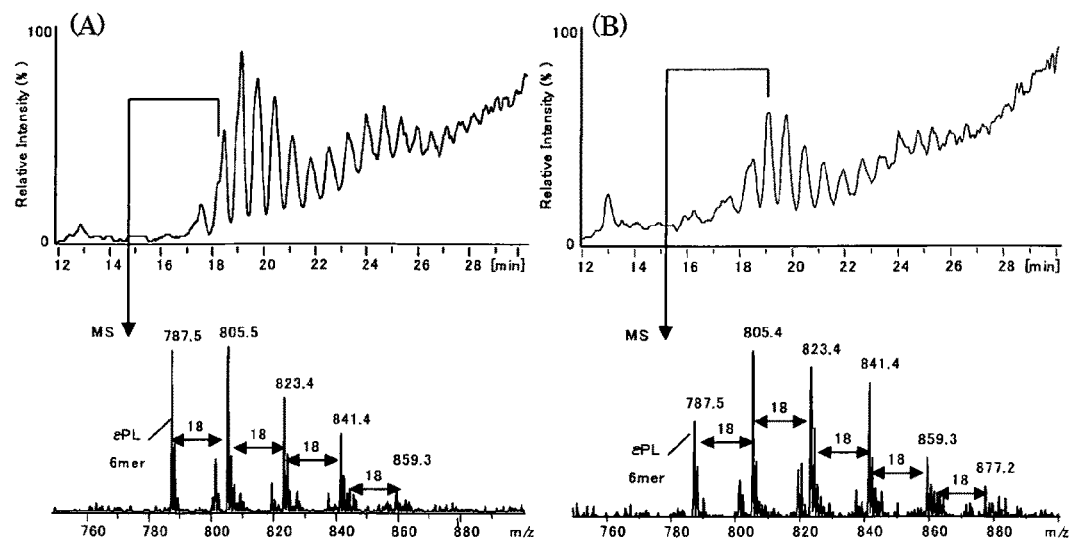
FIG. 10 shows the results of ESI-LC-MS analysis of polyamino acids produced by a reaction of bacterium. (A) is a graph showing the fraction pattern in LC and the result of mass analysis of a polyamino acid obtained from a reaction solution of bacterium containing 1.6 mM L-lysine. (B) is a graph showing the fraction pattern in LC and the result of mass analysis of a polyamino acid obtained from a reaction solution of bacterium containing 0.4 mM L-lysine.

A bacterium of *Streptomyces albulus*, which was obtained by culturing in a M3G medium (Example 1) at 30° C. for 36 hours, was washed with 100 mM citrate buffer solution (pH 4.2) twice. The washed bacterium obtained from 100 ml of culture solution was suspended in a reaction solution for bacterium consisting of 50 ml of 5% glucose, 1% ammonium sulfate, 8 mM S-(2-aminoethyl)-L-cysteine, 16 mM L-threonine (the concentration of each of the amino acids corresponds to a minimum growth inhibitory concentration against the bacterium in a M9 minimum medium, i.e., a minimum concentration to inhibit aspartokinase which is the key enzyme for L-lysine biosynthesis), and 100 mM citrate buffer solution (pH 4.2) containing a given amount of L-lysine, and it was subjected to shaking culture at 30° C. for 48 hours. After the completion of culture, polyamino acid contained in the culture supernatant collected by centrifugation was subjected to LC-MS analysis using the method of Example 1 (paragraph [0091]). As shown in FIG. 10, not only in the case of enzymatic reaction, but also in the case of use of a viable bacterium, heteropolyamino acid in which S-(2-aminoethyl)-L-cysteine is taken into the polylysine molecule was obtained at a constant frequency.

Also regarding analogs other than S-(2-aminoethyl)-L-cysteine, which are adenylated by the ε-poly-L-lysine biosynthetic enzyme, there is a high possibility that heteropolyamino acid can be microbially produced using a reaction solution for bacterium containing an analog in an amount corresponding to the minimum growth inhibitory concentration against the bacterium.

Example 6

Disruption of ε-Poly-L-Lysine Biosynthetic Enzyme Gene

In order to construct a plasmid for disrupting ε-poly-L-lysine biosynthetic enzyme gene, the following 2 types of primers were designed, and PCR was carried out using chromosomal DNA of *Streptomyces albulus* strain IFO14147, which is a ε-poly-L-lysine producing bacterium, as a template.

```
                                       (SEQ ID NO: 20)
e-PL_NRPS_F 5'-GGGGGATCCTCGTCGCCCCTTCTCGAATCG-3'

(SEQ ID NO: 21)
e-PL_NRPS_R 5'-ACCAAGCTTTCACGCGGCCGCACCTCCCTC-3'
```

The amplified PCR product (about 4 kbp) was digested with restriction enzymes BamHI and HindIII and cloned into a plasmid pLAE003 having a neomycin-resistant gene. Into the ε-poly-L-lysine biosynthetic gene of the constructed plasmid, a transposon containing an apramycin-resistant gene [aac(3)IV] was inserted (Reference: Actinomycetologica, 20, 35-41, 2006), thereby constructing a plasmid for disruption (pLAEnrps-apr). pLAEnrps-apr was introduced into *E. coli* S17-1, and in addition, by conjugation with *Streptomyces albulus*, pLAEnrps-apr was introduced into *Streptomyces albulus* (Reference: Journal of Bioscience and Bioengineering, 99, 636-641, 2005). A protoplast of the obtained introduced strain was prepared (Reference: Journal of Bioscience and Bioengineering, 99, 636-641, 2005), and it was applied to a medium for protoplast reproduction (Reference: Journal of Bioscience and Bioengineering, 99, 636-641, 2005). From the reproduced strain, a gene disruption candidate strain showing neomycin sensitivity and apramycin resistance was obtained (FIG. 11A). Chromosomal DNA was prepared from the obtained candidate strain, and after digested with a restriction enzyme KpnI, it was subjected to agarose electrophoresis. After electrophoresis, the agarose gel was transcribed into a nylon membrane, and a strain in which the ε-poly-L-lysine biosynthetic gene had been disrupted was selected by genomic Southern hybridization (CDP-star, GE Healthcare) using the ε-poly-L-lysine biosynthetic gene as a probe. As a result, one strain (PL-nrps::aac(3)IV) was obtained (FIG. 11B). The obtained disrupted strain was cultured in a production medium to confirm the productivity of ε-poly-L-lysine by HPLC (Example 1). It was confirmed that the productivity of ε-poly-L-lysine was lost (FIG. 11C) and that the obtained gene was a ε-poly-L-lysine biosynthetic gene.

Example 7

Acquisition of ε-Poly-L-Lysine Biosynthetic Gene Derived from *Streptomyces Noursei* Strain NBRC15452

It has already been known that not only *Streptomyces albulus* that is a ε-poly-L-lysine producing bacterium, but also a closely-related bacterium, *Streptomyces noursei* produce ε-poly-L-lysine (see Japanese Laid-Open Patent Publication No. 1-187090). Therefore, an attempt was made to obtain a ε-poly-L-lysine biosynthetic gene also from *Streptomyces noursei*.

A ε-poly-L-lysine biosynthetic gene ORF fragment of *Streptomyces albulus* amplified by PCR (see Example 6) was labeled using an ECL labeling kit manufactured by GE Healthcare Bio-Sciences. Using the labeled gene fragment as a probe, a cosmid library from the chromosomal DNA of *Streptomyces noursei* strain NBRC15452 constructed according to Example 1 (paragraphs [0100] to [0102]) (Supercos I, STRATAGENE) was subjected to screening, thereby obtaining a 6.5 kb KpnI fragment to which the probe hybridizes. This fragment was subcloned into a plasmid pGEM7Z (promega), thereby determining the nucleotide sequence (SEQ ID NO: 22). Further, the amino acid sequence corresponding to the nucleotide sequence (SEQ ID NO: 23) was determined.

Regarding this gene, the homology with the already-obtained ε-poly-L-lysine biosynthetic enzyme derived from *Streptomyces albulus* is very high (the nucleotide sequence level: 92.7%, the amino acid sequence level: 93.0%). Moreover, structural characteristics such as domain organization of the gene also correspond to those of the enzyme very well. Therefore, there is a high possibility that the gene encodes the ε-poly-L-lysine biosynthetic enzyme.

INDUSTRIAL APPLICABILITY

The method for enzymatically synthesizing a polyamino acid can save more energy than the microbial fermentation method and the chemical synthesis method, and can suppress undesired side reactions. Therefore, a highly-pure polyamino acid can be produced by the enzymatic synthesis method. Various polymers of amino acids produced according to the present invention can be used as an antimicrobial agent or the like, and can be used for various applications such as toiletry products, cosmetics, feed additives, medicines, agricultural chemicals, food additives, and electronic materials. Moreover, when using the polynucleotide-containing recombinant vector and the transformant of the present invention, application to biosynthesis of various useful polyamino acids can be expected.

The invention claimed is:

1. An isolated polynucleotide comprising any one of the following nucleotide sequences:
   (i) a nucleotide sequence encoding a polyamino acid synthetase consisting of the amino acid sequence of SEQ ID NO: 2;
   (ii) a nucleotide sequence encoding a polyamino acid synthetase consisting of an amino acid sequence having at least 90% identity to the amino acid sequence of SEQ ID NO: 2, wherein said polyamino acid synthetase polymerizes an amino acid in the presence of divalent cations including $Mg^{2+}$ and $Mn^{2+}$ utilizing the amino acid and ATP as its substrate;
   (iii) the nucleotide sequence of SEQ ID NO: 1;
   (iv) a nucleotide sequence encoding a polyamino acid synthetase, which can hybridize to a nucleotide sequence complementary to the nucleotide sequence of SEQ ID NO: 1 under highly stringent hybridization conditions (5 SSC; 5 Denhart solution; 0.5% (w/v) SDS; 50% (w/v) formamide; and 50° C.); and
   (v) a nucleotide sequence encoding a polyamino acid synthetase, which has at least 95% identity to the nucleotide sequence of SEQ ID NO: 1.

2. An isolated polynucleotide comprising:
   (i) a nucleotide sequence encoding a polyamino acid synthetase consisting of the amino acid sequence of SEQ ID NO: 2; or
   (ii) the nucleotide sequence of SEQ ID NO: 1.

3. The isolated polynucleotide according to claim 1, wherein the polyamino acid synthetase is a polylysine synthetase.

4. The isolated polynucleotide according to any one of claims 1 to 3, which is a DNA or RNA.

5. An isolated polynucleotide comprising any one of the following nucleotide sequences:
   (i) a nucleotide sequence encoding a condensation reaction catalytic domain or a subdomain thereof, which consists of the amino acid sequence of SEQ ID NO: 13, 15, 17 or 19;
   (ii) a nucleotide sequence encoding a condensation reaction catalytic domain or a subdomain thereof of a polyamino acid synthetase, wherein said condensation reaction catalytic domain consists of an amino acid sequence having at least 90% identity to the amino acid sequence of SEQ ID NO: 13, 15, 17 or 19, and wherein said polyamino acid synthetase polymerizes an amino acid in the presence of divalent cations including $Mg^{2+}$ and $Mn^{2+}$ utilizing the amino acid and ATP as its substrate;

(iii) the nucleotide sequence of SEQ ID NO: 12, 14, 16 or 18;

(iv) a nucleotide sequence encoding a condensation reaction catalytic domain or a subdomain thereof, which can hybridize to a nucleotide sequence complementary to the nucleotide sequence of SEQ ID NO: 12, 14, 16 or 18 under highly stringent hybridization conditions (5 SSC; 5 Denhart solution; 0.5% (w/v) SDS; 50% (w/v) formamide; and 50° C.); and (v) a nucleotide sequence encoding a condensation reaction catalytic domain or a subdomain thereof, which has at least 95% identity to the nucleotide sequence of SEQ ID NO: 12, 14, 16 or 18.

6. An isolated polynucleotide comprising:
(i) a nucleotide sequence encoding a condensation reaction catalytic domain or a subdomain thereof, which consists of the amino acid sequence of SEQ ID NO: 13, 15, 17 or 19; or
(ii) the nucleotide sequence of SEQ ID NO: 12, 14, 16 or 18.

7. The isolated polynucleotide according to claim 5 or 6, which is a DNA or RNA.

8. A recombinant vector comprising any one of the following nucleotide sequences:
(i) a nucleotide sequence encoding a polyamino acid synthetase consisting of the amino acid sequence of SEQ ID NO: 2;
(ii) a nucleotide sequence encoding a polyamino acid synthetase consisting of an amino acid sequence having at least 90% identity to the amino acid sequence of SEQ ID NO: 2, wherein said polyamino acid synthetase polymerizes an amino acid in the presence of divalent cations including $Mg^{2+}$ and $Mn^{2+}$ utilizing the amino acid and ATP as its substrate;
(iii) the nucleotide sequence of SEQ ID NO: 1;
(iv) a nucleotide sequence encoding a polyamino acid synthetase, which can hybridize to a nucleotide sequence complementary to the nucleotide sequence of SEQ ID NO: 1 under highly stringent hybridization conditions (5 SSC; 5 Denhart solution; 0.5% (w/v) SDS; 50% (w/v) formamide; and 50° C.); and
(v) a nucleotide sequence encoding a polyamino acid synthetase, which has at least 95% identity to the nucleotide sequence of SEQ ID NO: 1.

9. A recombinant vector comprising:
(i) a nucleotide sequence encoding a polyamino acid synthetase consisting of the amino acid sequence of SEQ ID NO: 2; or
(ii) the nucleotide sequence of SEQ ID NO: 1.

10. The recombinant vector according to claim 8, wherein the polyamino acid synthetase is a polylysine synthetase.

11. A recombinant vector comprising any one of the following nucleotide sequences:
(i) a nucleotide sequence encoding a condensation reaction catalytic domain or a subdomain thereof, which consists of the amino acid sequence of SEQ ID NO: 13, 15, 17 or 19;
(ii) a nucleotide sequence encoding a condensation reaction catalytic domain or a subdomain thereof of a polyamino acid synthetase, which consists of an amino acid sequence having at least 90% identity to the amino acid sequence of SEQ ID NO: 13, 15, 17 or 19, wherein said polyamino acid synthetase polymerizes an amino acid in the presence of divalent cations including $Mg^{2+}$ and $Mn^{2+}$ utilizing the amino acid and ATP as its substrate;
(iii) the nucleotide sequence of SEQ ID NO: 12, 14, 16 or 18;
(iv) a nucleotide sequence encoding a condensation reaction catalytic domain or a subdomain thereof, which can hybridize to a nucleotide sequence complementary to the nucleotide sequence of SEQ ID NO: 12, 14, 16 or 18 under highly stringent hybridization conditions (5 SSC; 5 Denhart solution; 0.5% (w/v) SDS; 50% (w/v) formamide; and 50° C.); and
(v) a nucleotide sequence encoding a condensation reaction catalytic domain or a subdomain thereof, which has at least 95% identity to the nucleotide sequence of SEQ ID NO: 12, 14, 16 or 18.

12. A recombinant vector comprising:
(i) a nucleotide sequence encoding a condensation reaction catalytic domain or a subdomain thereof, which consists of the amino acid sequence of SEQ ID NO: 13, 15, 17 or 19; or
(ii) the nucleotide sequence of SEQ ID NO: 12, 14, 16 or 18.

13. A transformant comprising the recombinant vector according to claim 8, 10 or 11.

14. A transformant comprising the recombinant vector according to claim 9 or 12.

15. A method for producing a polyamino acid synthetase comprising transforming a host cell with the recombinant vector according to claim 8, 10 or 11 and culturing the transformed cell.

16. A method for producing a polyamino acid synthetase, comprising performing in vitro transcription/translation of the recombinant vector according to claim 9 or 12.

17. A method for producing a polyamino acid synthetase, comprising culturing the transformant according to claim 14 and isolating a desired protein.

18. A method for producing a polyamino acid synthetase comprising culturing the transformant according to claim 13.

* * * * *

```
                        SEQUENCE LISTING

<160> NUMBER OF SEQ ID NOS: 23

<210> SEQ ID NO 1
<211> LENGTH: 3960
<212> TYPE: DNA
<213> ORGANISM: Streptomyces albulus

<400> SEQUENCE: 1
atgtcgtcgc cccttctcga atcgtccttc gagccgtccg agccagcgcc ccaacaggcc      60
ctgtaccgca ccgccggcaa cccggccccg cggaccctgc tcgacgtgct cgatgccacc     120
gccgccgcac atccccaggc gatcgccctg gacacgggct ccgaggcgct cacctaccgc     180
gacctgtgta tcgagatcga acgccgcgca cggcagctca gggaccgcgg catcggtccc     240
ggcgaccggg tcggagtccg cgtccccctcc gggaccgccg agctgtacct gtccatcctc     300
gccgtcctgc gcagcggagc ggcctacgtg ccggtcgacg ccgacgaccc cgacgagcgg     360
gccgccaccg tcttccgcga ggccgccgtc tgcgccgtcc tcggccccga cggcccgctg     420
cccggcccgg cccggccccct cggcgacccg cgttccgcgg cccccagga cgacgcctgg     480 atcatcttca cctcgggttc gaccggcgcg cccaaggggc tggcggtcag ccaccgctcc     540
gccgccgcct tcgtcgacgc cgaggccgac ctgttctgcc aggaccagcc gttgggcccc     600
ggcgaccggg tgctggccgg gctgtccgtc gccttcgacg cctcctgcga ggagatgtgg     660
ctcgcctggc ggtacggcgc ctgcctggtg cccgcacccc gcgcgctggt ccgggccggc     720
cacgaactcg gccctggct cgtcgagcgc ggcatcaccg tcgtctccac cgtgcccacc     780
ctcgccgcgc tctggccgga cgaggcgatg cgccgggtcc gcctgctgat cgtcggcggc     840
gaatcctgcc cggccgggct cgtcgaccgc ttcgccggac ccggccgcga gatgtggaac     900
acctacggcc cgaccgagac caccgtcgtc gcctgcgccg cccgcctgct gccgggcgag     960
ccggtccgca tcggcctgcc cctgaagggc tggcagctcg ccgtcgtcga ccgcaccggg    1020
cagccggtgc ccttcggcgc cgagggcgaa ctgctgatca gcggcgtcgg cacggcccgc    1080
tacctcgacc ccgccaagga cgccgaacgg ttccggcccg acgacgccct ggggccgcc    1140 cgcgtctacc gcaccggcga cctggtccgg gccgaacccg agggcctgct cttcgtcggc    1200
cgcgccgacg accagatcaa actcggcggc cgccgcatcg agctgggcga gatcgacgcc    1260
gccctggccg ccctgcccgg cgtccgcggg gccgccgcgg ccgtccagac gacgccggcc    1320
ggcacccagg tgctggtcgg ctacgtcgtt cccgagcagc gcaccgccga cggttccagc    1380
ttccagcagg acaaggcccg cgcactgctc caggaacgcc tgcccgcgca gttggtcccg    1440
gtcctcgcgg aggtcgagtc cctgcccacc cggacctccg gcaaggtcga ccgcaaggcg    1500
ctgccctggc cgctgccgtc cgccccggtc gactccgcca ccggcgatcc ggccacggcg    1560
ctggacggca ccgccgcccg gctcgccggg atctgggagg aactcctcgg cgtccggccc    1620 ggccccggaca gcgacttcgt ctccctcggc ggcaccagcc tggtcgccgc ccgcatggcg    1680
tcccagctcc gcatccacca cccggcgt tcggtcgccg acctctaccg ccaccgggtg    1740
ctgcgcgaca tggccgagca cctcgactcg ctggcggcc cggtggacga ggtccgcccg    1800
gtccgccccg tcccgcgccg caccggattc gtccaactcc tcgtccagac cggcctgtac    1860
```

-continued

| | |
|---|---|
| ggcatcgccg gcctgcgcgg actggtcggg ctcgcgctcg cggacaacgt cctcggcctg | 1920 |
| ctcgccccgc aggtctgggc cccgcacacc gcgtggtggc tgatcatcgt cggctgggtg | 1980 |
| gtgctctaca cgcccccgat gcgttgcgcc ctcggcgcac tggccgcccg cgcgctcgcc | 2040 |
| ggcaccatca agcccggcgc ctacccgcgc ggcggcgcca cccacctgcg cctgtggacc | 2100 |
| gccgaacgcg tcgtcgccgc cttcggcgtc ccctccctgc tcggcacccc ctggacgcgg | 2160 |
| ctctacgccc ggagcctggg ctgcgccaca gggcggaacg tggcgctgca caccatgccg | 2220 |
| ccggtcaccg gcctcgccga actcggcgac ggctgcagcg tcgaacccga ggccgacatc | 2280 |
| tccggctggt ggctcgacgg cgacaccctg cacatcggcg cggtccggat cggcgccggc | 2340 |
| gcccgggtcg cccaccgcag catgctgatg cccggcgccg tcgtcggcca gggcgccgaa | 2400 |
| ctcgcctccg gcgcctgcct ggacggagag atccccgacg cgcctcgtg gtccggctcc | 2460 |
| ccggcccgcc cggccggcgc cgccgagcgg atggccggcg ccgcctggcc cgcccccgcc | 2520 |
| tggcagcgct cgcgccgctg gagcgccgcc tacggactga ccctgctggg cctgtcgctg | 2580 |
| ctggccctgc tgtccaccgc gcccgccctg gtcggcgcgt acttcctgct ccgcgacagc | 2640 |
| ggcaccctcg ccacagccgg gcttcgcctg ctgctggccg tcccggtctt cacgctcctg | 2700 |
| accactggct gctccctcct cgtcaccgcc gccgtggtgc gcctcctcgg ccgcggcatc | 2760 |
| acgccgggac tgcaccccgc gagcggtggc gtcgcctggc gcgcctggct ggtcacccgc | 2820 |
| ctcctggacg gcgcccgcgg cagcctcttc ccgctctacg ccagcctcgg caccccgcac | 2880 |
| tggctgcggc tgctcggcgc caaggtcggc cggcacgcgg agatctccac cgtgctgccg | 2940 |
| ctgcccctcc tgctgcacgt cgaggacggc gcgttcctcg ccgacgacac cctggtggcg | 3000 |
| cccttcgaac tccgcggcgg ctggctgcgg ttggggaccg tccggatcgg tcgccgggcc | 3060 |
| ttcgtcggca actccggcat cgtcgacccc ggccacgacg tgcccgatca cagcctggtc | 3120 |
| ggcgtgctct ccaacgcccc cgccgacggc gagcccggct cgtcctggct gggcggccc | 3180 |
| gccatgccgc tgccccgggt ggcgacccag gccgacccgg cgcgcacctt cgcaccgccg | 3240 |
| cgcaggctgg tccgggcccg cgccgccgtc gagctgtgcc gggtgctgcc gctgatgtgc | 3300 |
| ggcctggcgc tcgccgaggg cgtgttcctc accgagcagg acgccttcgc ccagggcggc | 3360 |
| ctcggtctcg ccgcactggt cggcgccccg ctgctgctgg cctcgggcct cgtgcgctg | 3420 |
| ctcgtcacca ccctcgcgaa gtggctgctg gtcggccgct tcacggtgag cgagcacccc | 3480 |
| ctgtggtcgt cgttcgtgtg cgcaacgag ctctacgaca ccttcgtcga atcgctcgcc | 3540 |
| gtgccgtcga tggccggcgc gttcaccggc accccggtcc tgaactggtg gctgcgcacc | 3600 |
| ctcggcgcca agatcgggcg cggggtctgg ttggagagct actggctgcc ggagaccgac | 3660 |
| ctgatcaccg tcgccgacgg cgtcagcgtc aaccgcggct gcgtcctgca gacccacctc | 3720 |
| ttccacgacc ggatcatgcg gctggacacc gtccgcctcg ccgaaggctc ctcgctcggc | 3780 |
| ccgcacggca tcgtgctccc cggcaccgag gtcggggcgc gcgcctcgat cgcgccgtcg | 3840 |
| tccctggtca tgcgcggcga gagcgtcccg gcccacaccc ggtgggccgg caacccgatc | 3900 |
| gccggcgaac gccccgcccg ccccgtcccg gcacgcgcgg agggaggtgc ggccgcgtga | 3960 |

<210> SEQ ID NO 2
<211> LENGTH: 1319
<212> TYPE: PRT
<213> ORGANISM: Streptomyces albulus

<400> SEQUENCE: 2

Met Ser Ser Pro Leu Leu Glu Ser Ser Phe Glu Pro Ser Glu Pro Ala

```
1               5                   10                  15
Pro Gln Gln Ala Leu Tyr Arg Thr Ala Gly Asn Pro Ala Pro Arg Thr
            20                  25                  30

Leu Leu Asp Val Leu Asp Ala Thr Ala Ala His Pro Gln Ala Ile
            35                  40                  45

Ala Leu Asp Thr Gly Ser Glu Ala Leu Thr Tyr Arg Asp Leu Cys Ile
50                  55                  60

Glu Ile Glu Arg Arg Ala Arg Gln Leu Arg Asp Arg Gly Ile Gly Pro
65                  70                  75                  80

Gly Asp Arg Val Gly Val Arg Val Pro Ser Gly Thr Ala Glu Leu Tyr
                85                  90                  95

Leu Ser Ile Leu Ala Val Leu Arg Ser Gly Ala Ala Tyr Val Pro Val
            100                 105                 110

Asp Ala Asp Asp Pro Asp Glu Arg Ala Ala Thr Val Phe Arg Glu Ala
            115                 120                 125

Ala Val Cys Ala Val Leu Gly Pro Asp Gly Pro Leu Pro Gly Pro Ala
130                 135                 140

Arg Pro Leu Gly Asp Pro Arg Ser Ala Gly Pro Gln Asp Asp Ala Trp
145                 150                 155                 160

Ile Ile Phe Thr Ser Gly Ser Thr Gly Ala Pro Lys Gly Val Ala Val
                165                 170                 175

Ser His Arg Ser Ala Ala Ala Phe Val Asp Ala Glu Ala Asp Leu Phe
            180                 185                 190

Cys Gln Asp Gln Pro Leu Gly Pro Gly Asp Arg Val Leu Ala Gly Leu
            195                 200                 205

Ser Val Ala Phe Asp Ala Ser Cys Glu Glu Met Trp Leu Ala Trp Arg
210                 215                 220

Tyr Gly Ala Cys Leu Val Pro Ala Pro Arg Ala Leu Val Arg Ala Gly
225                 230                 235                 240

His Glu Leu Gly Pro Trp Leu Val Glu Arg Gly Ile Thr Val Val Ser
                245                 250                 255

Thr Val Pro Thr Leu Ala Ala Leu Trp Pro Asp Glu Ala Met Arg Arg
            260                 265                 270

Val Arg Leu Leu Ile Val Gly Gly Glu Ser Cys Pro Ala Gly Leu Val
            275                 280                 285

Asp Arg Phe Ala Gly Pro Gly Arg Glu Met Trp Asn Thr Tyr Gly Pro
            290                 295                 300

Thr Glu Thr Thr Val Val Ala Cys Ala Ala Arg Leu Leu Pro Gly Glu
305                 310                 315                 320

Pro Val Arg Ile Gly Leu Pro Leu Lys Gly Trp Gln Leu Ala Val Val
                325                 330                 335

Asp Arg Thr Gly Gln Pro Val Pro Phe Gly Ala Glu Gly Glu Leu Leu
            340                 345                 350

Ile Ser Gly Val Gly Thr Ala Arg Tyr Leu Asp Pro Ala Lys Asp Ala
            355                 360                 365

Glu Arg Phe Arg Pro Asp Asp Ala Leu Gly Ala Ala Arg Val Tyr Arg
            370                 375                 380

Thr Gly Asp Leu Val Arg Ala Glu Pro Glu Gly Leu Leu Phe Val Gly
385                 390                 395                 400

Arg Ala Asp Asp Gln Ile Lys Leu Gly Gly Arg Arg Ile Glu Leu Gly
                405                 410                 415

Glu Ile Asp Ala Ala Leu Ala Ala Leu Pro Gly Val Arg Gly Ala Ala
            420                 425                 430
```

```
Ala Ala Val Gln Thr Thr Pro Ala Gly Thr Gln Val Leu Val Gly Tyr
        435                 440                 445

Val Val Pro Glu Gln Arg Thr Ala Asp Gly Ser Ser Phe Gln Gln Asp
450                 455                 460

Lys Ala Arg Ala Leu Leu Gln Glu Arg Leu Pro Ala Gln Leu Val Pro
465                 470                 475                 480

Val Leu Ala Glu Val Glu Ser Leu Pro Thr Arg Thr Ser Gly Lys Val
                485                 490                 495

Asp Arg Lys Ala Leu Pro Trp Pro Leu Pro Ser Ala Pro Val Asp Ser
                500                 505                 510

Ala Thr Gly Asp Pro Ala Thr Ala Leu Asp Gly Thr Ala Ala Arg Leu
            515                 520                 525

Ala Gly Ile Trp Glu Glu Leu Leu Gly Val Arg Pro Gly Pro Asp Ser
            530                 535                 540

Asp Phe Val Ser Leu Gly Gly Thr Ser Leu Val Ala Ala Arg Met Ala
545                 550                 555                 560

Ser Gln Leu Arg Ile His His Pro Gly Val Ser Val Ala Asp Leu Tyr
                565                 570                 575

Arg His Pro Val Leu Arg Asp Met Ala Glu His Leu Asp Ser Leu Gly
                580                 585                 590

Gly Pro Val Asp Glu Val Arg Pro Val Arg Pro Val Pro Arg Arg Thr
            595                 600                 605

Gly Phe Val Gln Leu Leu Val Gln Thr Gly Leu Tyr Gly Ile Ala Gly
            610                 615                 620

Leu Arg Gly Leu Val Gly Leu Ala Leu Ala Asp Asn Val Leu Gly Leu
625                 630                 635                 640

Leu Ala Pro Gln Val Trp Ala Pro His Thr Ala Trp Trp Leu Ile Ile
                645                 650                 655

Val Gly Trp Val Val Leu Tyr Ser Ala Pro Met Arg Cys Ala Leu Gly
            660                 665                 670

Ala Leu Ala Ala Arg Ala Leu Ala Gly Thr Ile Lys Pro Gly Ala Tyr
            675                 680                 685

Pro Arg Gly Gly Ala Thr His Leu Arg Leu Trp Thr Ala Glu Arg Val
            690                 695                 700

Val Ala Ala Phe Gly Val Pro Ser Leu Leu Gly Thr Pro Trp Thr Arg
705                 710                 715                 720

Leu Tyr Ala Arg Ser Leu Gly Cys Ala Thr Gly Arg Asn Val Ala Leu
                725                 730                 735

His Thr Met Pro Pro Val Thr Gly Leu Ala Glu Leu Gly Asp Gly Cys
            740                 745                 750

Ser Val Glu Pro Glu Ala Asp Ile Ser Gly Trp Trp Leu Asp Gly Asp
            755                 760                 765

Thr Leu His Ile Gly Ala Val Arg Ile Gly Ala Gly Ala Arg Val Ala
        770                 775                 780

His Arg Ser Met Leu Met Pro Gly Ala Val Val Gly Gln Gly Ala Glu
785                 790                 795                 800

Leu Ala Ser Gly Ala Cys Leu Asp Gly Glu Ile Pro Asp Gly Ala Ser
                805                 810                 815

Trp Ser Gly Ser Pro Ala Arg Pro Ala Gly Ala Ala Glu Arg Met Ala
            820                 825                 830

Gly Ala Ala Trp Pro Ala Pro Ala Trp Gln Arg Ser Arg Arg Trp Ser
            835                 840                 845

Ala Ala Tyr Gly Leu Thr Leu Leu Gly Leu Ser Leu Leu Ala Leu Leu
            850                 855                 860
```

Ser Thr Ala Pro Ala Leu Val Gly Ala Tyr Phe Leu Arg Asp Ser
865                 870                 875                 880

Gly Thr Leu Ala Thr Ala Gly Leu Arg Leu Leu Ala Val Pro Val
        885                 890                 895

Phe Thr Leu Leu Thr Thr Gly Cys Ser Leu Leu Val Thr Ala Ala Val
            900                 905                 910

Val Arg Leu Leu Gly Arg Gly Ile Thr Pro Gly Leu His Pro Ala Ser
        915                 920                 925

Gly Gly Val Ala Trp Arg Ala Trp Leu Val Thr Arg Leu Leu Asp Gly
    930                 935                 940

Ala Arg Gly Ser Leu Phe Pro Leu Tyr Ala Ser Leu Gly Thr Pro His
945                 950                 955                 960

Trp Leu Arg Leu Leu Gly Ala Lys Val Gly Arg His Ala Glu Ile Ser
            965                 970                 975

Thr Val Leu Pro Leu Pro Ser Leu Leu His Val Glu Asp Gly Ala Phe
            980                 985                 990

Leu Ala Asp Asp Thr Leu Val Ala Pro Phe Glu Leu Arg Gly Gly Trp
        995                 1000                1005

Leu Arg Leu Gly Thr Val Arg Ile Gly Arg Ala Phe Val Gly
1010                1015                1020

Asn Ser Gly Ile Val Asp Pro Gly His Asp Val Pro Asp His Ser
1025                1030                1035

Leu Val Gly Val Leu Ser Asn Ala Pro Ala Asp Gly Glu Pro Gly
1040                1045                1050

Ser Ser Trp Leu Gly Arg Pro Ala Met Pro Leu Pro Arg Val Ala
1055                1060                1065

Thr Gln Ala Asp Pro Ala Arg Thr Phe Ala Pro Arg Arg Leu
1070                1075                1080

Val Arg Ala Arg Ala Ala Val Glu Leu Cys Arg Val Leu Pro Leu
1085                1090                1095

Met Cys Gly Leu Ala Leu Ala Glu Gly Val Phe Leu Thr Glu Gln
1100                1105                1110

Asp Ala Phe Ala Gln Gly Gly Leu Gly Leu Ala Ala Leu Val Gly
1115                1120                1125

Ala Pro Leu Leu Leu Ala Ser Gly Leu Val Ala Leu Leu Val Thr
1130                1135                1140

Thr Leu Ala Lys Trp Leu Leu Val Gly Arg Phe Thr Val Ser Glu
1145                1150                1155

His Pro Leu Trp Ser Ser Phe Val Trp Arg Asn Glu Leu Tyr Asp
1160                1165                1170

Thr Phe Val Glu Ser Leu Ala Val Pro Ser Met Ala Gly Ala Phe
1175                1180                1185

Thr Gly Thr Pro Val Leu Asn Trp Trp Leu Arg Thr Leu Gly Ala
1190                1195                1200

Lys Ile Gly Arg Gly Val Trp Leu Glu Ser Tyr Trp Leu Pro Glu
1205                1210                1215

Thr Asp Leu Ile Thr Val Ala Asp Gly Val Ser Val Asn Arg Gly
1220                1225                1230

Cys Val Leu Gln Thr His Leu Phe His Asp Arg Ile Met Arg Leu
1235                1240                1245

Asp Thr Val Arg Leu Ala Glu Gly Ser Ser Leu Gly Pro His Gly
1250                1255                1260

Ile Val Leu Pro Gly Thr Glu Val Gly Ala Arg Ala Ser Ile Ala

```
                      1265                1270                1275

Pro  Ser   Ser  Leu  Val  Met  Arg  Gly  Glu  Ser  Val  Pro  Ala  His  Thr
          1280                1285                1290

Arg  Trp  Ala  Gly  Asn  Pro  Ile  Ala  Gly  Glu  Arg  Pro  Ala  Arg  Pro
     1295                1300                1305

Val  Pro  Ala  Arg  Ala  Glu  Gly  Gly  Ala  Ala  Ala
    1310                1315

<210> SEQ ID NO 3
<211> LENGTH: 15
<212> TYPE: PRT
<213> ORGANISM: Artificial sequence
<220> FEATURE:
<223> OTHER INFORMATION: Synthetic construct; fragment-1

<400> SEQUENCE: 3

Met Gly Ala Ala Trp Pro Ala Pro Ala Trp Gln Arg Ser Arg
1               5                   10                  15

<210> SEQ ID NO 4
<211> LENGTH: 17
<212> TYPE: PRT
<213> ORGANISM: Artificial sequence
<220> FEATURE:
<223> OTHER INFORMATION: Synthetic construct; fragment-2
<220> FEATURE:
<221> NAME/KEY: misc_feature
<222> LOCATION: (1)..(1)
<223> OTHER INFORMATION: Xaa can be "Ile" or "Leu"
<220> FEATURE:
<221> NAME/KEY: misc_feature
<222> LOCATION: (3)..(3)
<223> OTHER INFORMATION: Xaa can be "Ile" or "Leu"
<220> FEATURE:
<221> NAME/KEY: misc_feature
<222> LOCATION: (6)..(6)
<223> OTHER INFORMATION: Xaa can be "Ile" or "Leu"
<220> FEATURE:
<221> NAME/KEY: misc_feature
<222> LOCATION: (10)..(10)
<223> OTHER INFORMATION: Xaa can be "Ile" or "Leu"
<220> FEATURE:
<221> NAME/KEY: misc_feature
<222> LOCATION: (13)..(13)
<223> OTHER INFORMATION: Xaa can be "Ile" or "Leu"

<400> SEQUENCE: 4

Xaa Glu Xaa Gly Glu Xaa Asp Ala Ala Xaa Ala Ala Xaa Pro Gly Val
1               5                   10                  15

Arg

<210> SEQ ID NO 5
<211> LENGTH: 13
<212> TYPE: PRT
<213> ORGANISM: Artificial sequence
<220> FEATURE:
<223> OTHER INFORMATION: Synthetic construct; fragment-3
<220> FEATURE:
<221> NAME/KEY: misc_feature
<222> LOCATION: (2)..(2)
<223> OTHER INFORMATION: Xaa can be "Ile" or "Leu"
<220> FEATURE:
<221> NAME/KEY: misc_feature
<222> LOCATION: (6)..(6)
<223> OTHER INFORMATION: Xaa can be "Ile" or "Leu"

<400> SEQUENCE: 5

Ala Xaa Ala Gly Thr Xaa Lys Pro Gly Ala Tyr Pro Arg
1               5                   10
```

```
<210> SEQ ID NO 6
<211> LENGTH: 13
<212> TYPE: PRT
<213> ORGANISM: Artificial sequence
<220> FEATURE:
<223> OTHER INFORMATION: Synthetic construct; peptide-1
<220> FEATURE:
<221> NAME/KEY: misc_feature
<222> LOCATION: (2)..(2)
<223> OTHER INFORMATION: Xaa can be "Ile" or "Leu"
<220> FEATURE:
<221> NAME/KEY: misc_feature
<222> LOCATION: (6)..(6)
<223> OTHER INFORMATION: Xaa can be "Ile" or "Leu"

<400> SEQUENCE: 6

Ala Xaa Ala Gly Thr Xaa Lys Pro Gly Ala Tyr Pro Arg
1               5                   10

<210> SEQ ID NO 7
<211> LENGTH: 15
<212> TYPE: PRT
<213> ORGANISM: Artificial sequence
<220> FEATURE:
<223> OTHER INFORMATION: Synthetic construct; peptide-2

<400> SEQUENCE: 7

Met Ala Gly Ala Ala Trp Pro Ala Pro Ala Trp Gln Arg Ser Arg
1               5                   10                  15

<210> SEQ ID NO 8
<211> LENGTH: 23
<212> TYPE: DNA
<213> ORGANISM: Artificial sequence
<220> FEATURE:
<223> OTHER INFORMATION: Synthetic construct; pr-pp1F primer

<400> SEQUENCE: 8
acsmtsaagc csggsgcsta ccc                                          23

<210> SEQ ID NO 9
<211> LENGTH: 24
<212> TYPE: DNA
<213> ORGANISM: Artificial sequence
<220> FEATURE:
<223> OTHER INFORMATION: Synthetic construct; pr-pp2R

<400> SEQUENCE: 9
ctgccasgcs ggsgcsggcc asgc                                         24

<210> SEQ ID NO 10
<211> LENGTH: 23
<212> TYPE: DNA
<213> ORGANISM: Artificial sequence
<220> FEATURE:
<223> OTHER INFORMATION: Synthetic construct; pr-pp2F

<400> SEQUENCE: 10
gcstggccsg csccsgcstg gca                                          23

<210> SEQ ID NO 11
<211> LENGTH: 23
<212> TYPE: DNA
<213> ORGANISM: Artificial sequence
<220> FEATURE:
<223> OTHER INFORMATION: Synthetic construct; pr-pp1R

<400> SEQUENCE: 11
```
gggtasgcsc csggcttsaw sgt                                                23

<210> SEQ ID NO 12
<211> LENGTH: 2127
<212> TYPE: DNA
<213> ORGANISM: Streptomyces albulus

<400> SEQUENCE: 12

| | | | | | |
|---|---|---|---|---|---|
| gtccaactcc | tcgtccagac | cggcctgtac | ggcatcgccg | gcctgcgcgg | actggtcggg | 60 |
| ctcgcgctcg | cggacaacgt | cctcggcctg | ctcgccccgc | aggtctgggc | cccgcacacc | 120 |
| gcgtggtggc | tgatcatcgt | cggctgggtg | gtgctctaca | gcgccccgat | gcgttgcgcc | 180 |
| ctcggcgcac | tggccgcccg | cgcgctcgcc | ggcaccatca | agcccggcgc | ctacccgcgc | 240 |
| ggcggcgcca | cccacctgcg | cctgtggacc | gccgaacgcg | tcgtcgccgc | cttcggcgtc | 300 |
| ccctccctgc | tcggcacccc | ctgggcgcgg | ctctacgccc | ggagcctggg | ctgcgccaca | 360 |
| gggcggaacg | tggcgctgca | caccatgccg | ccggtcaccg | gctcgccga | actcggcgac | 420 |
| ggctgcagcg | tcgaacccga | ggccgacatc | tccggctggt | ggctcgacgg | cgacaccctg | 480 |
| cacatcggcg | cggtccggat | cggcgccggc | gcccgggtcg | cccaccgcag | catgctgatg | 540 |
| cccggcgccg | tcgtcggcca | gggcgccgaa | ctcgcctccg | gcgcctgcct | ggacggagag | 600 |
| atccccgacg | gcgcctcgtg | gtccggctcc | ccggcccgcc | cggccggcgc | cgccgagcgg | 660 |
| atggccggcg | ccgcctggcc | cgccccgcc | tggcagcgct | cgcgccgctg | gagcgccgcc | 720 |
| tacggactga | ccctgctggg | cctgccgctg | ctggccctgc | tgtccaccgc | gcccgccctg | 780 |
| gtcggcgcgt | acttcctgct | ccgcgacagc | ggcaccctcg | ccacagccgg | gcttcgcctg | 840 |
| ctgctggccg | tcccggtctt | cacgctcctg | accactggct | gctccctcct | cgtcaccgcc | 900 |
| gccgtggtgc | gcctcctcgg | ccgcggcatc | acgccggac | tgcaccccgc | gagcggtggc | 960 |
| gtcgcctggc | gcgcctggct | ggtcaccgc | ctcctggacg | gcgcccgcgg | cagcctcttc | 1020 |
| ccgctctacg | ccagcctcgg | cacccgcac | tggctgcggc | tgctcggcgc | caaggtcggc | 1080 |
| cggcacgcgg | agatctccac | cgtgctgccg | ctgccctccc | tgctgcacgt | cgaggacggc | 1140 |
| gcgttcctcg | ccgacgacac | cctggtggcg | cccttcgaac | tccgcggcgg | ctggctgcgg | 1200 |
| ttggggaccg | tccggatcgg | tcgccgggcc | ttcgtcggca | actccggcat | cgtcgacccc | 1260 |
| ggccacgacg | tgcccgatca | cagcctggtc | ggcgtgctct | ccaacgcccc | cgccgacggc | 1320 |
| gagcccggct | cgtcctggct | gggccggccc | gccatgccgc | tgccccgggt | ggcgacccag | 1380 |
| gccgacccgg | cgcgcacctt | cgcaccgccg | cgcaggctgg | tccgggcccg | cgccgccgtc | 1440 |
| gagctgtgcc | gggtgctgcc | gctgatgtgc | ggcctggcgc | tcgccgaggg | cgtgttcctc | 1500 |
| accgagcagg | acgccttcgc | ccagggcggc | ctcggtctcg | ccgcactggt | cggcgccccg | 1560 |
| ctgctgctgg | cctcgggcct | cgtggcgctg | ctcgtcacca | ccctcgcgaa | gtggctgctg | 1620 |
| gtcggccgct | tcacggtgag | cgagcacccc | ctgtggtcgt | cgttcgtgtg | gcgcaacgag | 1680 |
| ctctacgaca | ccttcgtcga | atcgctcgcc | gtgccgtcga | tggccggcgc | gttcaccggc | 1740 |
| accccggtcc | tgaactggtg | gctgcgcacc | ctcgcgccca | agatcgggcg | cggggtctgg | 1800 |
| ttggagagct | actggctgcc | ggagaccgac | ctgatcaccg | tcgccgacgg | cgtcagcgtc | 1860 |
| aaccgcggct | gcgtcctgca | gacccacctc | ttccacgacc | ggatcatgcg | gctggacacc | 1920 |
| gtccgcctcg | ccgaaggctc | ctcgctcggc | ccgcacggca | tcgtgctccc | cggcaccgag | 1980 |
| gtcggggcgc | gcgcctcgat | cgcgccgtcg | tccctggtca | tgcgcggcga | gagcgtcccg | 2040 |
| gcccacaccc | ggtgggccgg | caacccgatc | gccggcgaac | gccccgcccg | ccccgtcccg | 2100 | gcacgcgcgg agggaggtgc ggccgcg					2127

<210> SEQ ID NO 13
<211> LENGTH: 709
<212> TYPE: PRT
<213> ORGANISM: Streptomyces albulus

<400> SEQUENCE: 13

Val Gln Leu Leu Val Gln Thr Gly Leu Tyr Gly Ile Ala Gly Leu Arg
1               5                   10                  15

Gly Leu Val Gly Leu Ala Leu Ala Asp Asn Val Leu Gly Leu Leu Ala
            20                  25                  30

Pro Gln Val Trp Ala Pro His Thr Ala Trp Trp Leu Ile Ile Val Gly
        35                  40                  45

Trp Val Val Leu Tyr Ser Ala Pro Met Arg Cys Ala Leu Gly Ala Leu
    50                  55                  60

Ala Ala Arg Ala Leu Ala Gly Thr Ile Lys Pro Gly Ala Tyr Pro Arg
65                  70                  75                  80

Gly Gly Ala Thr His Leu Arg Leu Trp Thr Ala Glu Arg Val Val Ala
                85                  90                  95

Ala Phe Gly Val Pro Ser Leu Leu Thr Pro Trp Ala Arg Leu Tyr
            100                 105                 110

Ala Arg Ser Leu Gly Cys Ala Thr Gly Arg Asn Val Ala Leu His Thr
        115                 120                 125

Met Pro Pro Val Thr Gly Leu Ala Glu Leu Gly Asp Gly Cys Ser Val
130                 135                 140

Glu Pro Glu Ala Asp Ile Ser Gly Trp Trp Leu Asp Gly Asp Thr Leu
145                 150                 155                 160

His Ile Gly Ala Val Arg Ile Gly Ala Gly Ala Arg Val Ala His Arg
                165                 170                 175

Ser Met Leu Met Pro Gly Ala Val Val Gly Gln Gly Ala Glu Leu Ala
            180                 185                 190

Ser Gly Ala Cys Leu Asp Gly Glu Ile Pro Asp Gly Ala Ser Trp Ser
        195                 200                 205

Gly Ser Pro Ala Arg Pro Ala Gly Ala Ala Glu Arg Met Ala Gly Ala
    210                 215                 220

Ala Trp Pro Ala Pro Ala Trp Gln Arg Ser Arg Arg Trp Ser Ala Ala
225                 230                 235                 240

Tyr Gly Leu Thr Leu Leu Gly Leu Pro Leu Leu Ala Leu Leu Ser Thr
                245                 250                 255

Ala Pro Ala Leu Val Gly Ala Tyr Phe Leu Leu Arg Asp Ser Gly Thr
            260                 265                 270

Leu Ala Thr Ala Gly Leu Arg Leu Leu Leu Ala Val Pro Val Phe Thr
        275                 280                 285

Leu Leu Thr Thr Gly Cys Ser Leu Leu Val Thr Ala Ala Val Val Arg
    290                 295                 300

Leu Leu Gly Arg Gly Ile Thr Pro Gly Leu His Pro Ala Ser Gly Gly
305                 310                 315                 320

Val Ala Trp Arg Ala Trp Leu Val Thr Arg Leu Leu Asp Gly Ala Arg
                325                 330                 335

Gly Ser Leu Phe Pro Leu Tyr Ala Ser Leu Gly Thr Pro His Trp Leu
            340                 345                 350

Arg Leu Leu Gly Ala Lys Val Gly Arg His Ala Glu Ile Ser Thr Val
        355                 360                 365

Leu Pro Leu Pro Ser Leu Leu His Val Glu Asp Gly Ala Phe Leu Ala

```
              370             375             380
Asp Asp Thr Leu Val Ala Pro Phe Glu Leu Arg Gly Gly Trp Leu Arg
385                     390                 395                 400

Leu Gly Thr Val Arg Ile Gly Arg Arg Ala Phe Val Gly Asn Ser Gly
                405                 410                 415

Ile Val Asp Pro Gly His Asp Val Pro Asp His Ser Leu Val Gly Val
                420                 425                 430

Leu Ser Asn Ala Pro Ala Asp Gly Glu Pro Gly Ser Ser Trp Leu Gly
                435                 440                 445

Arg Pro Ala Met Pro Leu Pro Arg Val Ala Thr Gln Ala Asp Pro Ala
450                 455                 460

Arg Thr Phe Ala Pro Arg Arg Leu Val Arg Ala Arg Ala Val
465                 470                 475                 480

Glu Leu Cys Arg Val Leu Pro Leu Met Cys Gly Leu Ala Leu Ala Glu
                485                 490                 495

Gly Val Phe Leu Thr Glu Gln Asp Ala Phe Ala Gln Gly Gly Leu Gly
                500                 505                 510

Leu Ala Ala Leu Val Gly Ala Pro Leu Leu Ala Ser Gly Leu Val
                515                 520                 525

Ala Leu Leu Val Thr Thr Leu Ala Lys Trp Leu Leu Val Gly Arg Phe
530                 535                 540

Thr Val Ser Glu His Pro Leu Trp Ser Ser Phe Val Trp Arg Asn Glu
545                 550                 555                 560

Leu Tyr Asp Thr Phe Val Glu Ser Leu Ala Val Pro Ser Met Ala Gly
                565                 570                 575

Ala Phe Thr Gly Thr Pro Val Leu Asn Trp Trp Leu Arg Thr Leu Gly
                580                 585                 590

Ala Lys Ile Gly Arg Gly Val Trp Leu Glu Ser Tyr Trp Leu Pro Glu
                595                 600                 605

Thr Asp Leu Ile Thr Val Ala Asp Gly Val Ser Val Asn Arg Gly Cys
                610                 615                 620

Val Leu Gln Thr His Leu Phe His Asp Arg Ile Met Arg Leu Asp Thr
625                 630                 635                 640

Val Arg Leu Ala Glu Gly Ser Ser Leu Gly Pro His Gly Ile Val Leu
                645                 650                 655

Pro Gly Thr Glu Val Gly Ala Arg Ala Ser Ile Ala Pro Ser Ser Leu
                660                 665                 670

Val Met Arg Gly Glu Ser Val Pro Ala His Thr Arg Trp Ala Gly Asn
                675                 680                 685

Pro Ile Ala Gly Glu Arg Pro Ala Arg Pro Val Pro Ala Arg Ala Glu
                690                 695                 700

Gly Gly Ala Ala Ala
705

<210> SEQ ID NO 14
<211> LENGTH: 516
<212> TYPE: DNA
<213> ORGANISM: Streptomyces albulus

<400> SEQUENCE: 14
gcccgcgcgc tcgccggcac catcaagccc ggcgcctacc cgcgcggcgg cgccacccac    60
ctgcgcctgt ggaccgccga acgcgtcgtc gccgccttcg gcgtcccctc cctgctcggc   120
accccctggg cgcggctcta cgccggagc ctgggctgcg ccacagggcg gaacgtggcg   180
ctgcacacca tgccgccggt caccggcctc gccgaactcg gcgacggctg cagcgtcgaa   240
```

```
cccgaggccg acatctccgg ctggtggctc gacggcgaca ccctgcacat cggcgcggtc    300
cggatcggcg ccggcgcccg ggtcgcccac cgcagcatgc tgatgcccgg cgccgtcgtc    360
ggccagggcg ccgaactcgc ctccggcgcc tgcctggacg gagagatccc cgacggcgcc    420
tcgtggtccg gctccccggc cgcccggcc ggcgccgccg agcggatggc cggcgccgcc    480
tggcccgccc cgcctggca gcgctcgcgc cgctgg                              516
```

```
<210> SEQ ID NO 15
<211> LENGTH: 172
<212> TYPE: PRT
<213> ORGANISM: Streptomyces albulus

<400> SEQUENCE: 15

Ala Arg Ala Leu Ala Gly Thr Ile Lys Pro Gly Ala Tyr Pro Arg Gly
1               5                   10                  15

Gly Ala Thr His Leu Arg Leu Trp Thr Ala Glu Arg Val Val Ala Ala
            20                  25                  30

Phe Gly Val Pro Ser Leu Leu Gly Thr Pro Trp Ala Arg Leu Tyr Ala
        35                  40                  45

Arg Ser Leu Gly Cys Ala Thr Gly Arg Asn Val Ala Leu His Thr Met
    50                  55                  60

Pro Pro Val Thr Gly Leu Ala Glu Leu Gly Asp Gly Cys Ser Val Glu
65                  70                  75                  80

Pro Glu Ala Asp Ile Ser Gly Trp Trp Leu Asp Gly Asp Thr Leu His
                85                  90                  95

Ile Gly Ala Val Arg Ile Gly Ala Gly Ala Arg Val Ala His Arg Ser
            100                 105                 110

Met Leu Met Pro Gly Ala Val Val Gly Gln Gly Ala Glu Leu Ala Ser
        115                 120                 125

Gly Ala Cys Leu Asp Gly Glu Ile Pro Asp Gly Ala Ser Trp Ser Gly
    130                 135                 140

Ser Pro Ala Arg Pro Ala Gly Ala Ala Glu Arg Met Ala Gly Ala Ala
145                 150                 155                 160

Trp Pro Ala Pro Ala Trp Gln Arg Ser Arg Arg Trp
                165                 170
```

```
<210> SEQ ID NO 16
<211> LENGTH: 510
<212> TYPE: DNA
<213> ORGANISM: Streptomyces albulus

<400> SEQUENCE: 16
cgcctcctcg gccgcggcat cacgccggga ctgcaccccg cgagcggtgg cgtcgcctgg     60
cgcgcctggc tggtcacccg cctcctggac ggcgcccgcg gcagcctctt cccgctctac    120
gccagcctcg gcaccccgca ctggctgcgg ctgctcggcg ccaaggtcgg ccggcacgcg    180
gagatctcca ccgtgctgcc gctgccctcc ctgctgcacg tcgaggacgg cgcgttcctc    240
gccgacgaca ccctggtggc gcccttcgaa ctccgcggcg gctggctgcg gttggggacc    300
gtccggatcg gtcgccgggc cttcgtcggc aactccggca tcgtcgaccc cggccacgac    360
gtgcccgatc acagcctggt cggcgtgctc tccaacgccc ccgccgacgg cgagcccggc    420
tcgtcctggc tgggccggcc cgccatgccg ctgcccgggt ggcgacccca ggccgacccg    480
gcgcgcacct tcgcaccgcc gcgcaggctg                                    510
```

```
<210> SEQ ID NO 17
```

```
<211> LENGTH: 170
<212> TYPE: PRT
<213> ORGANISM: Streptomyces albulus

<400> SEQUENCE: 17

Arg Leu Leu Gly Arg Gly Ile Thr Pro Gly Leu His Pro Ala Ser Gly
1               5                   10                  15

Gly Val Ala Trp Arg Ala Trp Leu Val Thr Arg Leu Leu Asp Gly Ala
            20                  25                  30

Arg Gly Ser Leu Phe Pro Leu Tyr Ala Ser Leu Gly Thr Pro His Trp
        35                  40                  45

Leu Arg Leu Leu Gly Ala Lys Val Gly Arg His Ala Glu Ile Ser Thr
    50                  55                  60

Val Leu Pro Leu Pro Ser Leu Leu His Val Glu Asp Gly Ala Phe Leu
65                  70                  75                  80

Ala Asp Asp Thr Leu Val Ala Pro Phe Glu Leu Arg Gly Gly Trp Leu
                85                  90                  95

Arg Leu Gly Thr Val Arg Ile Gly Arg Arg Ala Phe Val Gly Asn Ser
            100                 105                 110

Gly Ile Val Asp Pro Gly His Asp Val Pro Asp His Ser Leu Val Gly
        115                 120                 125

Val Leu Ser Asn Ala Pro Ala Asp Gly Glu Pro Gly Ser Ser Trp Leu
    130                 135                 140

Gly Arg Pro Ala Met Pro Leu Pro Arg Val Ala Thr Gln Ala Asp Pro
145                 150                 155                 160

Ala Arg Thr Phe Ala Pro Pro Arg Arg Leu
                165                 170

<210> SEQ ID NO 18
<211> LENGTH: 459
<212> TYPE: DNA
<213> ORGANISM: Streptomyces albulus

<400> SEQUENCE: 18
aagtggctgc tggtcggccg cttcacggtg agcgagcacc ccctgtggtc gtcgttcgtg      60
tggcgcaacg agctctacga caccttcgtc gaatcgctcg ccgtgccgtc gatggccggc     120
gcgttcaccg gcaccccggt cctgaactgg tggctgcgca cctcggcgc caagatcggg      180 cgcggggtct ggttggagag ctactggctg ccggagaccg acctgatcac cgtcgccgac     240
ggcgtcagcg tcaaccgcgg ctgcgtcctg cagacccacc tcttccacga ccggatcatg     300
cggctggaca ccgtccgcct cgccgaaggc tcctcgctcg gcccgcacgg catcgtgctc     360
cccggcaccg aggtcggggc gcgcgcctcg atcgcgccgt cgtccctggt catgcgcggc     420
gagagcgtcc cggcccacac ccggtgggcc ggcaacccg                            459

<210> SEQ ID NO 19
<211> LENGTH: 153
<212> TYPE: PRT
<213> ORGANISM: Streptomyces albulus

<400> SEQUENCE: 19

Lys Trp Leu Leu Val Gly Arg Phe Thr Val Ser Glu His Pro Leu Trp
1               5                   10                  15

Ser Ser Phe Val Trp Arg Asn Glu Leu Tyr Asp Thr Phe Val Glu Ser
            20                  25                  30

Leu Ala Val Pro Ser Met Ala Gly Ala Phe Thr Gly Thr Pro Val Leu
        35                  40                  45
```

```
Asn Trp Trp Leu Arg Thr Leu Gly Ala Lys Ile Gly Arg Gly Val Trp
 50                  55                  60

Leu Glu Ser Tyr Trp Leu Pro Glu Thr Asp Leu Ile Thr Val Ala Asp
 65                  70                  75                  80

Gly Val Ser Val Asn Arg Gly Cys Val Leu Gln Thr His Leu Phe His
                 85                  90                  95

Asp Arg Ile Met Arg Leu Asp Thr Val Arg Leu Ala Glu Gly Ser Ser
                100                 105                 110

Leu Gly Pro His Gly Ile Val Leu Pro Gly Thr Glu Val Gly Ala Arg
            115                 120                 125

Ala Ser Ile Ala Pro Ser Ser Leu Val Met Arg Gly Glu Ser Val Pro
    130                 135                 140

Ala His Thr Arg Trp Ala Gly Asn Pro
145                 150

<210> SEQ ID NO 20
<211> LENGTH: 30
<212> TYPE: DNA
<213> ORGANISM: Artificial sequence
<220> FEATURE:
<223> OTHER INFORMATION: Synthetic construct; e-PL_NRPS_F primer

<400> SEQUENCE: 20
gggggatcct cgtcgcccct tctcgaatcg                                       30

<210> SEQ ID NO 21
<211> LENGTH: 30
<212> TYPE: DNA
<213> ORGANISM: Artificial sequence
<220> FEATURE:
<223> OTHER INFORMATION: Synthetic construct; e-PL_NRPS_R primer

<400> SEQUENCE: 21
accaagcttt cacgcggccg cacctccctc                                       30

<210> SEQ ID NO 22
<211> LENGTH: 3961
<212> TYPE: DNA
<213> ORGANISM: Streptomyces noursei

<400> SEQUENCE: 22
atgtcgtcgc cccttctcga atcgtccttc gagccgtcag agccactgcc cgcacgggcc      60
gtttaccgca ccgccggcac cccggccccg cggaccctgc tcgacgtgct cgacgccacc     120
gcagccgcac accccaggc gatcgccctg acacgggcg ccgaggtgat cacctaccgc       180
gacctgtgca gcgagaccga acgtcgtgca cggcagctca gggacctcgg aatcggtccc     240
ggcgaccggg tcggagtccg cgtgccctcc ggaaccgccg agctgtacct ctcgatcctc     300
gccgtcctgc gcagcggagc ggcgtacgta ccggtcgatg ccgacgaccc cgacgagcgg     360
gccgccaccg tcttccggga ggccgccgtc tgcgccgtcc tcggtccggc cgcccagccg     420
cccgccctgg cccggcccgc cggggcgcca cgtcccccgg gcctccagga cgacgcctgg     480
atcatcttca catcgggttc gaccggcgcg cccaagggcg tcgcggtcag ccaccgctcc     540
gccgccgcct tcgtcgacgc cgaggccgtc ctgttctgcc aggaccgccc gctgggcccc     600
ggcgaccggg tactggccgg actgtccgtc gccttcgacg cctcctgcga ggagatgtgg     660
ctcgcctggc ggcacggcgc ctgcctggtg ccgcccccc gctcgctggt ccgcgccggc     720
cacgaactcg gccgtggct ggtcgagcgg ggcatcaccg tggtctccac cgtgcccacc     780
ctcgccgcgc tctggcccga cgaggcgatg cgccgggtcc ggctgctgat cgtcggcggc     840
```

```
gagtcctgcc ccgccgggct cgtcgaccgc ttcgccggac ccggccggga gatgtggaac    900
acctacggcc cgaccgaggc caccgtcgtc gcctgtgccg cccgcctccg gccgggccag    960
ccggtccgca tcggcctgcc cctggagggc tggcagctgg ccgtcgtgga ccggccggc    1020 cggccggtgc cctacggcgc cgagggcgag ttgctcatca gcggcgtcgg caccgcccgc   1080
tacctcgacc cggtcaagga cgccgagcgc ttcggcccg acgacgtcct ggacaccgcc    1140
cgcgcctacc gcaccggcga cctggtccgc gccgaacccg agggcctgct cttcgtcggc   1200
cgcgccgacg accagatcaa actcggcggt cgacgcatcg agttgggcga gatcgacgcc   1260
gcgctggccg ccctgccgg cgtcctcggc gccgccgcgg ccgtccagac cacccggcc     1320 ggcacccagg tcctggtcgg ctacgtcgtc cccgagcagc gcaccaccga cggctccagc   1380
ttccagcagg acaaggcccg cgcgctgctc caggaacggc tgccggcgca gctcgtaccc   1440
gtcctcgcgg aggtcgagag cctgcccacc cggacgtccg gcaaggtcga ccgcaaggcg   1500
ctgccctggc cgctgccgac cgccccggtc gacggtgcgg ccggcgcccc ggccccggcg   1560
ctgcacggca ccgccgcccg cctggccggc atctgggagg aactcctcgg cgtccggccc   1620
ggcccggaca gcgacttcgt ctccctcggc ggcaccagcc tggtcgccgc ccggatggcc   1680
tcccagctcc gcgcccacca ccccggcgtc tcggtcgccg acctctaccg ccacccggtg   1740
ctgcgcgaca tggccgtgca cctcgactcg ctgggcggcc cggtggacga ggtccgcccg   1800
gtccgccccg tcccgcgccg cgccggccgtc gtccaactcc tcgtccagac cggcctgtac   1860
ggcatcgccg gcctgcgcgg actggtcggg ctcgcgctcg ccgacaacat cctcggctgg   1920
ctcgccccgc aggtctgggc cccgcacacc gcctggtggc tgatcatcgt cggctgggtg   1980
gtgctctaca gcgcccgat gcgctgcgcc ctcggcgccc tcgccgcccg gatgctcgcc   2040
ggctcgatcc ggcccggcgc ctatccgcgc ggcggcgcca cccatctgcg cctgtggacc   2100
gccgaacgcg tggtcgccgc cttcggcgtc ccctcgctgc tcggtacgcc ctgggcgcgg   2160
ctgtacgccc ggaccctggg ctgcaccacc gggcggaacg tggcgctgca caccatgccg   2220
ccggtcaccg gcctcgccga actcggcgac ggctgcagca tcgaacccga ggccgacctc   2280
tccggctggt ggctcgacgg cgacaccctg cacatcggcg ccgtccggat cggcgccggc   2340
gcccgggtcg cccaccgcag catgctgatg cccggcgccg tcgtcggaca gggcgccgaa   2400
ctcaccgccg gcgcctgcct ggacggcgag atccccgacg gcgcctgctg gtccggctcc   2460
ccggcccgcc cggccggcgc cgccgagcgg atggccggcg ccgcgtggcc cgccccgcgc   2520
tggcggcgtt cgctcggctg gagcgccgcc tacggtctct ccctgctggg cctgccgctg   2580
ctggcgctgc tgtccaccgc cccggcactg gtcggcgcgt acttcctgct ccgcgacagc   2640
ggcaccctcg ccaccgcggc ggtccgcctg ctgctggccg tccggtcttt cacgctcgtc   2700
accaccggct cctcgatcct ggtgaccgcc gccgtggtgc ggctcctcgg ccgcggcatc   2760
acgccgggcg tgcacccggc gagcggcggc gtcgcctggc gcgcctggct ggtgacccgc   2820 ctcctgacg gcgcccgcgg cagcctcttc ccgctctacg ccagcctcgg caccccgcac   2880
tggctgcggc tgctcggcgc caaggtcggc aagcacgcgc agatctccac cgtgctgccg   2940
ctgccctcgc tgctgcacgt cgaggacggc gccttcctgg ccgacgacac cctggtcgcc   3000
cccttcgaac tccgcggcgg atggctgcgg ttggggaccg tccggatcgg ccgccggggc   3060
ttcgtcggca actccggcat cgtcgacccc ggccacgacg tccccgacca cagcctggtc   3120
ggcgtgctct ccaacgcacc cgccgacggc gagcccggga tgtcgtggct gggtcggccc   3180
gcgatgccgc tgccccgggt ggcggcccag gccgatccgg cgcgtacctt cgcgccgccg   3240
```

```
cgcaagctgg tcctggcccg cgccgccgtc gaactgtgcc gggtgctgcc cctgatgtgc   3300
ggagtggccc tcgccgaggg cgtgttcctc accgagcagg acgtcttcgc cagcggcgg   3360 ctcggcctcg cggcgctggt cggcgccccg ctgctgctgc tctcgggcct ggtggcgctg   3420
ctcgtcacga cccggcgaa gtggacgctg gtcggccggt tcaccgccgg cgagcacccg   3480
ctgtggtcgc ccttcgtctg cgcaacgag ctctacgaca ccttcgtcga gtcgctcgcc   3540
gtgccgtcga tggccggcgc cttcaccggc accccggtcc tcaactggtg gctgcgcacc   3600
ctcggcgcca agatcggccg cggcgtctgg ctggagagct actggctgcc ggagaccgac   3660
ctgatcaccc tcgccgacgg cgtcagcgtc aaccgcggct gcgtgctgca gacccacctg   3720
ttccacgacc ggatcatgcg cctggacacc gtccggctcg ccgagggctc ttcgctcggc   3780
ccgcacggca tcgtgctccc cggcaccgac gtcggcgcgc gcgcctcgat cgcaccgtcc   3840
tccctggtca tgcgcggcga gagcgtgccc gcgcacaccc gctgggccgg caacccgatc   3900
gccggcgaac gcccgacccg tcccgccgcg cgctcgcgg agggtggtgc tgccgcgtga   3960
c                                                                  3961
```

<210> SEQ ID NO 23  
<211> LENGTH: 1319  
<212> TYPE: PRT  
<213> ORGANISM: Streptomyces noursei

<400> SEQUENCE: 23

```
Met Ser Ser Pro Leu Leu Glu Ser Ser Phe Glu Pro Ser Glu Pro Leu
1               5                   10                  15

Pro Ala Arg Ala Val Tyr Arg Thr Ala Gly Thr Pro Ala Pro Arg Thr
                20                  25                  30

Leu Leu Asp Val Leu Asp Ala Thr Ala Ala Ala His Pro Gln Ala Ile
            35                  40                  45

Ala Leu Asp Thr Gly Ala Glu Val Ile Thr Tyr Arg Asp Leu Cys Ser
        50                  55                  60

Glu Thr Glu Arg Arg Ala Arg Gln Leu Arg Asp Leu Gly Ile Gly Pro
65                  70                  75                  80

Gly Asp Arg Val Gly Val Arg Val Pro Ser Gly Thr Ala Glu Leu Tyr
                85                  90                  95

Leu Ser Ile Leu Ala Val Leu Arg Ser Gly Ala Ala Tyr Val Pro Val
            100                 105                 110

Asp Ala Asp Asp Pro Asp Glu Arg Ala Ala Thr Val Phe Arg Glu Ala
        115                 120                 125

Ala Val Cys Ala Val Leu Gly Pro Ala Ala Gln Pro Pro Ala Leu Ala
    130                 135                 140

Arg Pro Ala Gly Ala Pro Arg Pro Pro Gly Leu Gln Asp Asp Ala Trp
145                 150                 155                 160

Ile Ile Phe Thr Ser Gly Ser Thr Gly Ala Pro Lys Gly Val Ala Val
                165                 170                 175

Ser His Arg Ser Ala Ala Ala Phe Val Asp Ala Glu Ala Val Leu Phe
            180                 185                 190

Cys Gln Asp Arg Pro Leu Gly Pro Gly Asp Arg Val Leu Ala Gly Leu
        195                 200                 205

Ser Val Ala Phe Asp Ala Ser Cys Glu Glu Met Trp Leu Ala Trp Arg
    210                 215                 220

His Gly Ala Cys Leu Val Pro Ala Pro Arg Ser Leu Val Arg Ala Gly
225                 230                 235                 240
```

-continued

His Glu Leu Gly Pro Trp Leu Val Glu Arg Gly Ile Thr Val Val Ser
                245                 250                 255

Thr Val Pro Thr Leu Ala Ala Leu Trp Pro Asp Glu Ala Met Arg Arg
            260                 265                 270

Val Arg Leu Leu Ile Val Gly Gly Glu Ser Cys Pro Ala Gly Leu Val
        275                 280                 285

Asp Arg Phe Ala Gly Pro Gly Arg Glu Met Trp Asn Thr Tyr Gly Pro
    290                 295                 300

Thr Glu Ala Thr Val Val Ala Cys Ala Ala Arg Leu Arg Pro Gly Gln
305                 310                 315                 320

Pro Val Arg Ile Gly Leu Pro Leu Glu Gly Trp Gln Leu Ala Val Val
                325                 330                 335

Asp Arg Ala Gly Arg Pro Val Pro Tyr Gly Ala Glu Gly Glu Leu Leu
            340                 345                 350

Ile Ser Gly Val Gly Thr Ala Arg Tyr Leu Asp Pro Val Lys Asp Ala
        355                 360                 365

Glu Arg Phe Arg Pro Asp Asp Val Leu Asp Thr Ala Arg Ala Tyr Arg
    370                 375                 380

Thr Gly Asp Leu Val Arg Ala Glu Pro Glu Gly Leu Leu Phe Val Gly
385                 390                 395                 400

Arg Ala Asp Asp Gln Ile Lys Leu Gly Gly Arg Arg Ile Glu Leu Gly
                405                 410                 415

Glu Ile Asp Ala Ala Leu Ala Ala Leu Pro Gly Val Leu Gly Ala Ala
            420                 425                 430

Ala Ala Val Gln Thr Thr Pro Ala Gly Thr Gln Val Leu Val Gly Tyr
        435                 440                 445

Val Val Pro Glu Gln Arg Thr Thr Asp Gly Ser Ser Phe Gln Gln Asp
    450                 455                 460

Lys Ala Arg Ala Leu Leu Gln Glu Arg Leu Pro Ala Gln Leu Val Pro
465                 470                 475                 480

Val Leu Ala Glu Val Glu Ser Leu Pro Thr Arg Thr Ser Gly Lys Val
                485                 490                 495

Asp Arg Lys Ala Leu Pro Trp Pro Leu Pro Thr Ala Pro Val Asp Gly
            500                 505                 510

Ala Ala Gly Ala Pro Ala Pro Ala Leu His Gly Thr Ala Ala Arg Leu
        515                 520                 525

Ala Gly Ile Trp Glu Glu Leu Leu Gly Val Arg Pro Gly Pro Asp Ser
    530                 535                 540

Asp Phe Val Ser Leu Gly Gly Thr Ser Leu Val Ala Ala Arg Met Ala
545                 550                 555                 560

Ser Gln Leu Arg Ala His His Pro Gly Val Ser Val Ala Asp Leu Tyr
                565                 570                 575

Arg His Pro Val Leu Arg Asp Met Ala Val His Leu Asp Ser Leu Gly
            580                 585                 590

Gly Pro Val Asp Glu Val Arg Pro Val Arg Pro Val Pro Arg Arg Ala
        595                 600                 605

Gly Val Val Gln Leu Leu Val Gln Thr Gly Leu Tyr Gly Ile Ala Gly
    610                 615                 620

Leu Arg Gly Leu Val Gly Leu Ala Leu Ala Asp Asn Ile Leu Gly Trp
625                 630                 635                 640

Leu Ala Pro Gln Val Trp Ala Pro His Thr Ala Trp Trp Leu Ile Ile
                645                 650                 655

Val Gly Trp Val Val Leu Tyr Ser Ala Pro Met Arg Cys Ala Leu Gly
            660                 665                 670

```
Ala Leu Ala Ala Arg Met Leu Ala Gly Ser Ile Arg Pro Gly Ala Tyr
            675                 680                 685
Pro Arg Gly Gly Ala Thr His Leu Arg Leu Trp Thr Ala Glu Arg Val
690                 695                 700
Val Ala Ala Phe Gly Val Pro Ser Leu Leu Gly Thr Pro Trp Ala Arg
705                 710                 715                 720
Leu Tyr Ala Arg Thr Leu Gly Cys Thr Thr Gly Arg Asn Val Ala Leu
                725                 730                 735
His Thr Met Pro Pro Val Thr Gly Leu Ala Glu Leu Gly Asp Gly Cys
            740                 745                 750
Ser Ile Glu Pro Glu Ala Asp Leu Ser Gly Trp Trp Leu Asp Gly Asp
        755                 760                 765
Thr Leu His Ile Gly Ala Val Arg Ile Gly Ala Gly Ala Arg Val Ala
    770                 775                 780
His Arg Ser Met Leu Met Pro Gly Ala Val Val Gly Gln Gly Ala Glu
785                 790                 795                 800
Leu Thr Ala Gly Ala Cys Leu Asp Gly Glu Ile Pro Asp Gly Ala Cys
                805                 810                 815
Trp Ser Gly Ser Pro Ala Arg Pro Ala Gly Ala Ala Glu Arg Met Ala
            820                 825                 830
Gly Ala Ala Trp Pro Ala Pro Arg Trp Arg Arg Ser Leu Gly Trp Ser
        835                 840                 845
Ala Ala Tyr Gly Leu Ser Leu Leu Gly Leu Pro Leu Leu Ala Leu Leu
    850                 855                 860
Ser Thr Ala Pro Ala Leu Val Gly Ala Tyr Phe Leu Leu Arg Asp Ser
865                 870                 875                 880
Gly Thr Leu Ala Thr Ala Ala Val Arg Leu Leu Leu Ala Val Pro Val
                885                 890                 895
Phe Thr Leu Val Thr Thr Gly Ser Ser Ile Leu Val Thr Ala Ala Val
            900                 905                 910
Val Arg Leu Leu Gly Arg Gly Ile Thr Pro Gly Val His Pro Ala Ser
        915                 920                 925
Gly Gly Val Ala Trp Arg Ala Trp Leu Val Thr Arg Leu Leu Asp Gly
    930                 935                 940
Ala Arg Gly Ser Leu Phe Pro Leu Tyr Ala Ser Leu Gly Thr Pro His
945                 950                 955                 960
Trp Leu Arg Leu Leu Gly Ala Lys Val Gly Lys His Ala Glu Ile Ser
                965                 970                 975
Thr Val Leu Pro Leu Pro Ser Leu Leu His Val Glu Gly Ala Phe
            980                 985                 990
Leu Ala Asp Asp Thr Leu Val Ala Pro Phe Glu Leu Arg Gly Gly Trp
        995                 1000                1005
Leu Arg Leu Gly Thr Val Arg Ile Gly Arg Arg Ala Phe Val Gly
    1010                1015                1020
Asn Ser Gly Ile Val Asp Pro Gly His Asp Val Pro Asp His Ser
1025                1030                1035
Leu Val Gly Val Leu Ser Asn Ala Pro Ala Asp Gly Glu Pro Gly
            1040                1045                1050
Met Ser Trp Leu Gly Arg Pro Ala Met Pro Leu Pro Arg Val Ala
        1055                1060                1065
```

-continued

```
Ala Gln Ala Asp Pro Ala Arg Thr Phe Ala Pro Pro Arg Lys Leu
    1070            1075            1080

Val Leu Ala Arg Ala Ala Val Glu Leu Cys Arg Val Leu Pro Leu
    1085            1090            1095

Met Cys Gly Val Ala Leu Ala Glu Gly Val Phe Leu Thr Glu Gln
    1100            1105            1110

Asp Val Phe Ala Ser Gly Gly Leu Gly Leu Ala Ala Leu Val Gly
    1115            1120            1125

Ala Pro Leu Leu Leu Leu Ser Gly Leu Val Ala Leu Leu Val Thr
    1130            1135            1140

Thr Leu Ala Lys Trp Thr Leu Val Gly Arg Phe Thr Ala Gly Glu
    1145            1150            1155

His Pro Leu Trp Ser Pro Phe Val Trp Arg Asn Glu Leu Tyr Asp
    1160            1165            1170

Thr Phe Val Glu Ser Leu Ala Val Pro Ser Met Ala Gly Ala Phe
    1175            1180            1185

Thr Gly Thr Pro Val Leu Asn Trp Trp Leu Arg Thr Leu Gly Ala
    1190            1195            1200

Lys Ile Gly Arg Gly Val Trp Leu Glu Ser Tyr Trp Leu Pro Glu
    1205            1210            1215

Thr Asp Leu Ile Thr Leu Ala Asp Gly Val Ser Val Asn Arg Gly
    1220            1225            1230

Cys Val Leu Gln Thr His Leu Phe His Asp Arg Ile Met Arg Leu
    1235            1240            1245

Asp Thr Val Arg Leu Ala Glu Gly Ser Ser Leu Gly Pro His Gly
    1250            1255            1260

Ile Val Leu Pro Gly Thr Asp Val Gly Ala Arg Ala Ser Ile Ala
    1265            1270            1275

Pro Ser Ser Leu Val Met Arg Gly Glu Ser Val Pro Ala His Thr
    1280            1285            1290

Arg Trp Ala Gly Asn Pro Ile Ala Gly Glu Arg Pro Thr Arg Pro
    1295            1300            1305

Ala Ala Ala Leu Ala Glu Gly Gly Ala Ala Ala
    1310            1315
```